US011331094B2

(12) United States Patent
Graul et al.

(10) Patent No.: US 11,331,094 B2
(45) Date of Patent: May 17, 2022

(54) METHOD AND APPARATUS FOR ATTACHING TISSUE TO BONE

(71) Applicant: Stryker Corporation, Kalamazoo, MI (US)

(72) Inventors: Jeremy Graul, Elk Grove, CA (US); Brett Page, Sunnyvale, CA (US); J. Brook Burley, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 200 days.

(21) Appl. No.: 16/379,150

(22) Filed: Apr. 9, 2019

(65) Prior Publication Data
US 2019/0231342 A1 Aug. 1, 2019

Related U.S. Application Data

(63) Continuation of application No. 14/258,837, filed on Apr. 22, 2014, now Pat. No. 10,292,694.
(Continued)

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0414* (2013.01);
(Continued)

(58) Field of Classification Search
CPC .......... A61B 17/0401; A61B 17/06166; A61B 2017/0414; A61B 2017/0446;
(Continued)

(56) References Cited

U.S. PATENT DOCUMENTS

| 749,624 A | 1/1904 | McCullough |
| 919,138 A | 4/1909 | Drake et al. |

(Continued)

FOREIGN PATENT DOCUMENTS

| CA | 2713309 A1 | 2/2011 |
| DE | 3131496 A1 | 2/1983 |

(Continued)

OTHER PUBLICATIONS

International Search Report for PCT/US2014/035018 dated Sep. 30, 2014.

(Continued)

*Primary Examiner* — Wade Miles
*Assistant Examiner* — Kankindi Rwego
(74) *Attorney, Agent, or Firm* — Lerner, David, Littenberg, Krumholz & Mentlik, LLP

(57) ABSTRACT

In one embodiment of the present disclosure, an apparatus for securing a first object to a second object, including a deformable anchor body, a working suture connected to the anchor body, the working suture including a pre-formed knot, and a repair suture connected to the first object, wherein, with the anchor body connected to the second object and at least one of the anchor body and the working suture connected to the repair suture, the anchor body is adapted to secure within the second object and the working suture and repair suture are adapted to secure to the anchor body to secure the first object to the second object.

17 Claims, 40 Drawing Sheets

Related U.S. Application Data

(60) Provisional application No. 61/881,007, filed on Sep. 23, 2013, provisional application No. 61/814,403, filed on Apr. 22, 2013.

(52) U.S. Cl.
CPC ............... *A61B 2017/0446* (2013.01); *A61B 2017/0454* (2013.01); *A61B 2017/0458* (2013.01); *A61B 2017/0464* (2013.01); *A61B 2017/0496* (2013.01); *A61B 2017/06176* (2013.01)

(58) Field of Classification Search
CPC .... A61B 2017/0454; A61B 2017/0458; A61B 2017/0464; A61B 2017/0475; A61B 2017/0477; A61B 2017/0496; A61B 2017/06176; A61F 2/0811; A61F 2002/0817; A61F 2002/0823; A61F 2002/0835
USPC ........................................................ 606/228
See application file for complete search history.

(56) References Cited

U.S. PATENT DOCUMENTS

| | | |
|---|---|---|
| 1,308,798 A | 7/1919 | Masland |
| 1,624,530 A | 4/1927 | Caruso |
| 2,073,903 A | 3/1937 | O'Neil |
| 2,250,434 A | 7/1941 | Dugaw |
| 2,267,925 A | 12/1941 | Johnston |
| 2,382,019 A | 8/1945 | Miller |
| 2,416,260 A | 2/1947 | Karle |
| 2,461,947 A | 2/1949 | Weber |
| 2,494,229 A | 1/1950 | Collison |
| 2,515,365 A | 7/1950 | Zublin |
| 2,547,571 A | 4/1951 | Ettinger |
| 2,579,192 A | 12/1951 | Kohl |
| 2,773,672 A | 12/1956 | Holmes et al. |
| 2,808,055 A | 10/1957 | Thayer |
| 2,808,632 A | 10/1957 | Cline |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,566,739 A | 3/1971 | Lebar |
| 3,580,256 A | 5/1971 | Wilkinson et al. |
| 3,608,095 A | 9/1971 | Barry |
| 3,659,597 A | 5/1972 | Wolfers |
| 3,708,883 A | 1/1973 | Flander |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 3,981,051 A | 9/1976 | Brumlik |
| 4,212,569 A | 7/1980 | Andersson et al. |
| 4,265,231 A | 5/1981 | Scheller, Jr. et al. |
| 4,328,839 A | 5/1982 | Lyons et al. |
| 4,408,938 A | 10/1983 | Maguire |
| 4,483,562 A | 11/1984 | Schoolman |
| 4,484,570 A | 11/1984 | Sutter et al. |
| 4,489,446 A | 12/1984 | Reed |
| 4,492,226 A | 1/1985 | Belykh et al. |
| 4,541,423 A | 9/1985 | Barber |
| 4,590,928 A | 5/1986 | Hunt et al. |
| 4,594,033 A | 6/1986 | Peetz et al. |
| 4,605,347 A | 8/1986 | Jodock et al. |
| 4,605,414 A | 8/1986 | Czajka |
| 4,608,972 A | 9/1986 | Small |
| 4,611,515 A | 9/1986 | Marbourg, Jr. |
| 4,632,100 A | 12/1986 | Somers et al. |
| 4,635,738 A | 1/1987 | Schillinger et al. |
| 4,646,738 A | 3/1987 | Trott |
| 4,706,659 A | 11/1987 | Matthews et al. |
| 4,708,132 A | 11/1987 | Silvestrini |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,778,468 A | 10/1988 | Hunt et al. |
| 4,779,616 A | 10/1988 | Johnson |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,870,957 A | 10/1989 | Goble et al. |
| 4,871,289 A | 10/1989 | Choiniere |
| 4,872,451 A | 10/1989 | Moore et al. |
| 4,927,421 A | 5/1990 | Goble et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,046,513 A | 9/1991 | Gatturna et al. |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,165,494 A | 11/1992 | Barr |
| 5,176,682 A | 1/1993 | Chow |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| 5,207,679 A | 5/1993 | Li |
| 5,209,753 A | 5/1993 | Biedermann et al. |
| RE34,293 E | 6/1993 | Goble et al. |
| 5,224,946 A | 7/1993 | Hayhurst et al. |
| 5,226,426 A | 7/1993 | Yoon |
| 5,234,435 A | 8/1993 | Seagrave, Jr. |
| 5,236,445 A | 8/1993 | Hayhurst et al. |
| 5,259,846 A | 11/1993 | Granger et al. |
| 5,268,001 A | 12/1993 | Nicholson et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,330,442 A | 7/1994 | Green et al. |
| 5,330,468 A | 7/1994 | Burkhart |
| 5,336,240 A | 8/1994 | Metzler et al. |
| 5,342,376 A | 8/1994 | Ruff |
| 5,350,383 A | 9/1994 | Schmieding et al. |
| RE34,762 E | 10/1994 | Goble et al. |
| 5,354,298 A | 10/1994 | Lee et al. |
| 5,364,407 A | 11/1994 | Poll |
| 5,374,269 A | 12/1994 | Rosenberg |
| 5,380,334 A | 1/1995 | Torrie et al. |
| 5,383,905 A | 1/1995 | Golds et al. |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,352 A | 4/1995 | Weston |
| 5,405,359 A | 4/1995 | Pierce |
| 5,409,494 A | 4/1995 | Morgan |
| 5,411,523 A | 5/1995 | Goble |
| 5,417,691 A | 5/1995 | Hayhurst |

(56) References Cited

U.S. PATENT DOCUMENTS

| | | |
|---|---|---|
| 5,417,712 A | 5/1995 | Whittaker et al. |
| 5,423,824 A | 6/1995 | Akerfeldt et al. |
| 5,423,860 A | 6/1995 | Lizardi et al. |
| 5,437,630 A | 8/1995 | Daniel et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,464,427 A | 11/1995 | Curtis et al. |
| 5,466,243 A | 11/1995 | Schmieding et al. |
| 5,472,452 A | 12/1995 | Trott |
| 5,480,403 A | 1/1996 | Lee et al. |
| 5,486,197 A | 1/1996 | Le et al. |
| 5,488,761 A | 2/1996 | Leone |
| 5,489,210 A | 2/1996 | Hanosh |
| 5,496,348 A | 3/1996 | Bonutti |
| 5,499,991 A | 3/1996 | Garman et al. |
| 5,501,683 A | 3/1996 | Trott |
| 5,501,692 A | 3/1996 | Riza |
| 5,501,695 A | 3/1996 | Anspach, Jr. et al. |
| 5,505,736 A | 4/1996 | Reimels et al. |
| 5,514,159 A | 5/1996 | Matula et al. |
| 5,520,693 A | 5/1996 | McGuire et al. |
| 5,520,700 A | 5/1996 | Beyar et al. |
| 5,522,844 A | 6/1996 | Johnson |
| 5,522,845 A | 6/1996 | Wenstrom, Jr. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,545,180 A | 8/1996 | Le et al. |
| 5,548,862 A | 8/1996 | Curtis |
| 5,562,683 A | 10/1996 | Chan |
| 5,562,687 A | 10/1996 | Chan |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,571,139 A | 11/1996 | Jenkins, Jr. |
| 5,573,542 A | 11/1996 | Stevens |
| 5,575,819 A | 11/1996 | Amis |
| 5,584,617 A | 12/1996 | Houser |
| 5,584,695 A | 12/1996 | Lal Sachdeva et al. |
| 5,584,835 A | 12/1996 | Greenfield |
| 5,601,550 A | 2/1997 | Esser |
| 5,601,557 A | 2/1997 | Hayhurst |
| 5,601,558 A | 2/1997 | Torrie et al. |
| 5,601,561 A | 2/1997 | Terry et al. |
| 5,611,515 A | 3/1997 | Benderev et al. |
| 5,618,314 A | 4/1997 | Harwin et al. |
| 5,630,824 A | 5/1997 | Hart |
| 5,632,748 A | 5/1997 | Beck, Jr. et al. |
| 5,643,292 A | 7/1997 | Hart |
| 5,643,321 A | 7/1997 | McDevitt |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,289 A | 8/1997 | Boucher et al. |
| 5,658,313 A | 8/1997 | Thal |
| 5,662,658 A | 9/1997 | Wenstrom, Jr. |
| 5,664,914 A | 9/1997 | Taniguchi |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,671,695 A | 9/1997 | Schroeder |
| 5,674,279 A | 10/1997 | Wright et al. |
| 5,681,315 A | 10/1997 | Szabo |
| 5,681,320 A | 10/1997 | McGuire |
| 5,681,333 A | 10/1997 | Burkhart et al. |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,649 A | 11/1997 | Li |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,702,215 A | 12/1997 | Li |
| 5,702,397 A | 12/1997 | Goble et al. |
| 5,702,422 A | 12/1997 | Stone |
| 5,707,374 A | 1/1998 | Schmidt |
| 5,707,395 A | 1/1998 | Li |
| 5,709,708 A | 1/1998 | Thal |
| 5,713,905 A | 2/1998 | Goble et al. |
| 5,716,368 A | 2/1998 | de la Torre et al. |
| 5,716,397 A | 2/1998 | Myers |
| 5,718,717 A | 2/1998 | Bonutti |
| 5,720,765 A | 2/1998 | Thal |
| 5,725,529 A | 3/1998 | Nicholson et al. |
| 5,725,530 A | 3/1998 | Popken |
| 5,725,541 A | 3/1998 | Anspach, III et al. |
| 5,725,557 A | 3/1998 | Gatturna et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,741,300 A | 4/1998 | Li |
| 5,746,752 A | 5/1998 | Burkhart |
| 5,746,753 A | 5/1998 | Sullivan et al. |
| 5,749,899 A | 5/1998 | Bardin et al. |
| 5,755,724 A | 5/1998 | Yoon |
| 5,755,728 A | 5/1998 | Maki |
| 5,755,731 A | 5/1998 | Grinberg |
| 5,759,185 A | 6/1998 | Grinberg |
| 5,766,221 A | 6/1998 | Benderev et al. |
| 5,782,862 A | 7/1998 | Bonutti |
| 5,782,863 A | 7/1998 | Bartlett |
| 5,782,864 A | 7/1998 | Lizardi |
| 5,782,866 A | 7/1998 | Wenstrom, Jr. |
| 5,788,699 A | 8/1998 | Bobst et al. |
| 5,791,899 A | 8/1998 | Sachdeva et al. |
| 5,797,918 A | 8/1998 | McGuire et al. |
| 5,797,963 A | 8/1998 | McDevitt |
| 5,810,825 A | 9/1998 | Huebner |
| 5,814,056 A | 9/1998 | Prosst et al. |
| 5,814,071 A | 9/1998 | McDevitt et al. |
| 5,814,072 A | 9/1998 | Bonutti |
| 5,814,073 A | 9/1998 | Bonutti |
| 5,820,464 A | 10/1998 | Parlato |
| 5,836,953 A | 11/1998 | Yoon |
| 5,843,127 A | 12/1998 | Li |
| 5,845,645 A | 12/1998 | Bonutti |
| 5,849,004 A | 12/1998 | Bramlet |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,895,179 A | 4/1999 | Gschwend et al. |
| 5,897,574 A | 4/1999 | Bonutti |
| 5,906,624 A | 5/1999 | Wenstrom, Jr. |
| 5,906,626 A | 5/1999 | Carrillo |
| 5,908,423 A | 6/1999 | Kashuba et al. |
| 5,910,148 A | 6/1999 | Reimels et al. |
| 5,911,721 A | 6/1999 | Nicholson et al. |
| 5,921,986 A | 7/1999 | Bonutti |
| 5,928,244 A | 7/1999 | Tovey et al. |
| 5,935,129 A | 8/1999 | McDevitt et al. |
| 5,935,134 A | 8/1999 | Pedlick et al. |
| 5,935,149 A | 8/1999 | Ek |
| 5,941,139 A | 8/1999 | Vodehnal |
| 5,941,883 A | 8/1999 | Sklar |
| 5,947,659 A | 9/1999 | Mays |
| 5,948,000 A | 9/1999 | Larsen et al. |

(56) References Cited

U.S. PATENT DOCUMENTS

| | | |
|---|---|---|
| 5,948,001 A | 9/1999 | Larsen |
| 5,948,002 A | 9/1999 | Bonutti |
| 5,951,559 A | 9/1999 | Burkhart |
| 5,954,747 A | 9/1999 | Clark |
| 5,957,953 A | 9/1999 | DiPoto et al. |
| 5,961,538 A | 10/1999 | Pedlick et al. |
| 5,968,044 A | 10/1999 | Nicholson et al. |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,993,459 A | 11/1999 | Larsen et al. |
| 5,997,541 A | 12/1999 | Schenk |
| 6,007,566 A | 12/1999 | Wenstrom, Jr. |
| 6,007,567 A | 12/1999 | Bonutti |
| 6,010,514 A | 1/2000 | Burney et al. |
| 6,010,515 A | 1/2000 | Swain et al. |
| 6,010,525 A | 1/2000 | Bonutti et al. |
| 6,019,767 A | 2/2000 | Howell |
| 6,022,360 A | 2/2000 | Reimels et al. |
| 6,024,758 A | 2/2000 | Thal |
| 6,030,406 A | 2/2000 | Davis et al. |
| 6,041,485 A | 3/2000 | Pedlick et al. |
| 6,045,573 A | 4/2000 | Wenstrom, Jr. et al. |
| 6,045,574 A | 4/2000 | Thal |
| 6,053,922 A | 4/2000 | Krause et al. |
| 6,056,772 A | 5/2000 | Bonutti |
| 6,068,642 A | 5/2000 | Johnson et al. |
| 6,077,277 A | 6/2000 | Mollenauer et al. |
| 6,077,292 A | 6/2000 | Bonutti |
| 6,083,244 A | 7/2000 | Lubbers et al. |
| 6,083,522 A | 7/2000 | Chu et al. |
| 6,086,608 A | 7/2000 | Ek et al. |
| 6,099,538 A | 8/2000 | Moses et al. |
| 6,099,547 A | 8/2000 | Gellman et al. |
| 6,117,144 A | 9/2000 | Nobles et al. |
| 6,120,511 A | 9/2000 | Chan |
| 6,143,017 A | 11/2000 | Thal |
| 6,146,385 A | 11/2000 | Torrie et al. |
| 6,149,669 A | 11/2000 | Li |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,200,329 B1 | 3/2001 | Fung et al. |
| 6,210,415 B1 | 4/2001 | Bester |
| 6,221,107 B1 | 4/2001 | Steiner et al. |
| 6,224,608 B1 | 5/2001 | Ciccolella et al. |
| 6,231,592 B1 | 5/2001 | Bonutti et al. |
| 6,241,732 B1 | 6/2001 | Overaker et al. |
| 6,245,081 B1 | 6/2001 | Bowman et al. |
| 6,245,082 B1 | 6/2001 | Gellman et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,296,659 B1 | 10/2001 | Foerster |
| 6,306,138 B1 | 10/2001 | Clark et al. |
| 6,306,159 B1 | 10/2001 | Schwartz et al. |
| 6,312,438 B1 | 11/2001 | Adams |
| 6,312,448 B1 | 11/2001 | Bonutti |
| 6,319,252 B1 | 11/2001 | McDevitt et al. |
| 6,319,269 B1 | 11/2001 | Li |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,402,781 B1 | 6/2002 | Langberg et al. |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,474,425 B1 | 11/2002 | Truax et al. |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,506,190 B1 | 1/2003 | Walshe |
| 6,508,830 B2 | 1/2003 | Steiner |
| 6,511,498 B1 | 1/2003 | Fumex |
| 6,517,578 B2 | 2/2003 | Hein |
| 6,517,579 B1 | 2/2003 | Paulos et al. |
| 6,520,980 B1 | 2/2003 | Foerster |
| 6,524,316 B1 | 2/2003 | Nicholson et al. |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,547,800 B2 | 4/2003 | Foerster et al. |
| 6,547,807 B2 | 4/2003 | Chan et al. |
| 6,558,386 B1 | 5/2003 | Cragg |
| 6,558,390 B2 | 5/2003 | Cragg |
| 6,562,071 B2 | 5/2003 | Jarvinen |
| 6,569,187 B1 | 5/2003 | Bonutti et al. |
| 6,572,635 B1 | 6/2003 | Bonutti |
| 6,575,976 B2 | 6/2003 | Grafton |
| 6,575,979 B1 | 6/2003 | Cragg |
| 6,575,987 B2 | 6/2003 | Gellman et al. |
| 6,582,453 B1 | 6/2003 | Tran et al. |
| 6,585,730 B1 | 7/2003 | Foerster |
| 6,599,310 B2 | 7/2003 | Leung et al. |
| 6,610,080 B2 | 8/2003 | Morgan |
| 6,620,166 B1 | 9/2003 | Wenstrom, Jr. et al. |
| 6,629,984 B1 | 10/2003 | Chan |
| 6,635,073 B2 | 10/2003 | Bonutti |
| 6,638,279 B2 | 10/2003 | Bonutti |
| 6,638,283 B2 | 10/2003 | Thal |
| 6,641,596 B1 | 11/2003 | Lizardi |
| 6,641,597 B2 | 11/2003 | Burkhart et al. |
| 6,652,450 B2 | 11/2003 | Neisz et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,692,516 B2 | 2/2004 | West, Jr. et al. |
| 6,712,822 B2 | 3/2004 | Re et al. |
| 6,716,234 B2 | 4/2004 | Grafton et al. |
| 6,730,092 B2 | 5/2004 | Songer |
| 6,733,506 B1 | 5/2004 | McDevitt et al. |
| 6,740,090 B1 | 5/2004 | Cragg et al. |
| 6,746,451 B2 | 6/2004 | Middleton et al. |
| 6,746,457 B2 | 6/2004 | Dana et al. |
| 6,752,814 B2 | 6/2004 | Gellman et al. |
| 6,770,073 B2 | 8/2004 | McDevitt et al. |
| 6,770,076 B2 | 8/2004 | Foerster |
| 6,773,450 B2 | 8/2004 | Leung et al. |
| 6,780,188 B2 | 8/2004 | Clark et al. |
| 6,780,198 B1 | 8/2004 | Gregoire et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,814,741 B2 | 11/2004 | Bowman et al. |
| 6,824,552 B2 | 11/2004 | Robison et al. |
| 6,830,570 B1 | 12/2004 | Frey et al. |
| 6,848,152 B2 | 2/2005 | Genova et al. |
| 6,855,157 B2 | 2/2005 | Foerster et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |

(56) References Cited

U.S. PATENT DOCUMENTS

| | | |
|---|---|---|
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,932,834 B2 | 8/2005 | Lizardi et al. |
| 6,936,052 B2 | 8/2005 | Gellman et al. |
| 6,942,666 B2 | 9/2005 | Overaker et al. |
| 6,955,683 B2 | 10/2005 | Bonutti |
| 6,960,214 B2 | 11/2005 | Burkinshaw |
| 6,984,241 B2 | 1/2006 | Lubbers et al. |
| 6,986,781 B2 | 1/2006 | Smith |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,029,490 B2 | 4/2006 | Grafton et al. |
| 7,033,380 B2 | 4/2006 | Schwartz et al. |
| 7,037,324 B2 | 5/2006 | Martinek |
| 7,041,107 B2 | 5/2006 | Pohjonen et al. |
| 7,041,120 B2 | 5/2006 | Li et al. |
| 7,048,754 B2 | 5/2006 | Martin et al. |
| 7,048,755 B2 | 5/2006 | Bonutti et al. |
| 7,056,331 B2 | 6/2006 | Kaplan et al. |
| 7,060,073 B2 | 6/2006 | Frey et al. |
| 7,067,132 B2 | 6/2006 | Grabstein et al. |
| 7,074,203 B1 | 7/2006 | Johanson et al. |
| 7,077,863 B2 | 7/2006 | Schmieding et al. |
| 7,081,126 B2 | 7/2006 | McDevitt et al. |
| 7,083,638 B2 | 8/2006 | Foerster |
| 7,087,058 B2 | 8/2006 | Cragg |
| 7,087,073 B2 | 8/2006 | Bonutti |
| 7,090,690 B2 | 8/2006 | Foerster et al. |
| 7,144,415 B2 | 12/2006 | Del Rio et al. |
| 7,160,314 B2 | 1/2007 | Sgro et al. |
| 7,204,839 B2 | 4/2007 | Dreyfuss et al. |
| 7,217,279 B2 | 5/2007 | Reese |
| 7,217,290 B2 | 5/2007 | Bonutti |
| 7,225,512 B2 | 6/2007 | Genova et al. |
| 7,226,469 B2 | 6/2007 | Benavitz et al. |
| 7,235,091 B2 | 6/2007 | Thornes |
| 7,235,100 B2 | 6/2007 | Martinek |
| 7,241,297 B2 | 7/2007 | Shaolian et al. |
| 7,258,692 B2 | 8/2007 | Thelen et al. |
| 7,261,016 B2 | 8/2007 | Miller |
| 7,285,124 B2 | 10/2007 | Foerster |
| 7,309,338 B2 | 12/2007 | Cragg |
| 7,309,346 B2 | 12/2007 | Martinek |
| 7,326,215 B2 | 2/2008 | Myers et al. |
| 7,329,272 B2 | 2/2008 | Burkhart et al. |
| 7,331,263 B2 | 2/2008 | Erickson et al. |
| 7,371,253 B2 | 5/2008 | Leung et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,507,200 B2 | 3/2009 | Okada |
| 7,517,357 B2 | 4/2009 | Abrams et al. |
| 7,520,898 B2 | 4/2009 | Re et al. |
| 7,556,640 B2 | 7/2009 | Foerster |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,624,487 B2 | 12/2009 | Trull et al. |
| 7,637,926 B2 | 12/2009 | Foerster et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,662,171 B2 | 2/2010 | West, Jr. et al. |
| 7,666,189 B2 | 2/2010 | Gerber et al. |
| 7,674,274 B2 | 3/2010 | Foerster et al. |
| 7,674,276 B2 | 3/2010 | Stone et al. |
| 7,678,134 B2 | 3/2010 | Schmieding et al. |
| 7,682,374 B2 | 3/2010 | Foerster et al. |
| 7,695,494 B2 | 4/2010 | Foerster |
| 7,704,262 B2 | 4/2010 | Bellafiore et al. |
| 7,713,286 B2 | 5/2010 | Singhatat |
| 7,749,250 B2 | 7/2010 | Stone et al. |
| 7,776,049 B1 | 8/2010 | Curran et al. |
| 7,780,701 B1 | 8/2010 | Meridew et al. |
| 7,794,484 B2 | 9/2010 | Stone et al. |
| 7,803,173 B2 | 9/2010 | Burkhart et al. |
| 7,828,820 B2 | 11/2010 | Stone et al. |
| 7,837,710 B2 | 11/2010 | Lombardo et al. |
| 7,842,050 B2 | 11/2010 | Diduch et al. |
| 7,846,167 B2 | 12/2010 | Garcia et al. |
| 7,857,829 B2 | 12/2010 | Kaplan et al. |
| 7,857,830 B2 | 12/2010 | Stone et al. |
| 7,867,264 B2 | 1/2011 | McDevitt et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,892,256 B2 | 2/2011 | Grafton et al. |
| 7,896,907 B2 | 3/2011 | McDevitt et al. |
| 7,901,431 B2 | 3/2011 | Shumas |
| 7,905,903 B2 | 3/2011 | Stone et al. |
| 7,905,904 B2 | 3/2011 | Stone et al. |
| 7,909,547 B2 | 3/2011 | Jordan et al. |
| 7,909,851 B2 | 3/2011 | Stone et al. |
| 7,913,365 B2 | 3/2011 | Genova et al. |
| 7,914,539 B2 | 3/2011 | Stone et al. |
| 7,918,874 B2 | 4/2011 | Siegal |
| 7,938,847 B2 | 5/2011 | Fanton et al. |
| 7,959,650 B2 | 6/2011 | Kaiser et al. |
| 7,963,967 B1 | 6/2011 | Woods |
| 7,963,972 B2 | 6/2011 | Foerster et al. |
| 7,976,565 B1 | 7/2011 | Meridew |
| 7,981,117 B2 | 7/2011 | Newton et al. |
| 7,981,140 B2 | 7/2011 | Burkhart |
| 7,993,369 B2 | 8/2011 | Dreyfuss |
| 7,996,967 B2 | 8/2011 | Genova et al. |
| 7,996,968 B2 | 8/2011 | Genova et al. |
| 8,002,733 B2 | 8/2011 | Kraft et al. |
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,029,537 B2 | 10/2011 | West, Jr. et al. |
| 8,032,996 B2 | 10/2011 | Trull et al. |
| 8,043,253 B2 | 10/2011 | Kraft et al. |
| 8,057,500 B2 | 11/2011 | Mitusina |
| 8,057,524 B2 | 11/2011 | Meridew |
| 8,066,718 B2 | 11/2011 | Weisel et al. |
| 8,070,750 B2 | 12/2011 | Wenstrom, Jr. et al. |
| 8,075,572 B2 | 12/2011 | Stefanchik et al. |
| 8,083,770 B2 | 12/2011 | Ruff et al. |
| RE43,143 E | 1/2012 | Hayhurst |
| 8,088,130 B2 | 1/2012 | Kaiser et al. |
| 8,100,940 B2 | 1/2012 | Leung et al. |
| 8,100,942 B1 | 1/2012 | Green et al. |
| 8,109,700 B2 | 2/2012 | Jordan et al. |
| 8,109,969 B1 | 2/2012 | Green et al. |
| 8,114,088 B2 | 2/2012 | Miller |
| 8,118,834 B1 | 2/2012 | Goraltchouk et al. |
| 8,118,835 B2 | 2/2012 | Weisel et al. |
| 8,118,836 B2 | 2/2012 | Denham et al. |
| 8,123,750 B2 | 2/2012 | Norton et al. |
| 8,128,640 B2 | 3/2012 | Harris et al. |
| 8,128,641 B2 | 3/2012 | Wardle |
| 8,128,658 B2 | 3/2012 | Kaiser et al. |
| 8,128,669 B2 | 3/2012 | Bonutti |

(56) References Cited

U.S. PATENT DOCUMENTS

| | | |
|---|---|---|
| 8,133,231 B2 | 3/2012 | Martinek et al. |
| 8,133,258 B2 | 3/2012 | Foerster et al. |
| 8,137,381 B2 | 3/2012 | Foerster et al. |
| 8,137,382 B2 | 3/2012 | Denham et al. |
| 8,137,383 B2 | 3/2012 | West, Jr. et al. |
| 8,147,514 B2 | 4/2012 | Bonutti |
| 8,162,978 B2 | 4/2012 | Lombardo et al. |
| 8,162,997 B2 | 4/2012 | Struhl |
| 8,172,846 B2 | 5/2012 | Brunnett et al. |
| 8,216,273 B1 | 7/2012 | Goraltchouk et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,246,652 B2 | 8/2012 | Ruff |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,298,291 B2 | 10/2012 | Ewers et al. |
| 8,303,604 B2 | 11/2012 | Stone et al. |
| 8,312,942 B2 | 11/2012 | Ho et al. |
| 8,317,825 B2 | 11/2012 | Stone |
| 8,337,525 B2 | 12/2012 | Stone et al. |
| 8,343,187 B2 | 1/2013 | Lamson et al. |
| 8,361,113 B2 | 1/2013 | Stone et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,252 B2 | 4/2013 | Lombardo et al. |
| 8,409,253 B2 | 4/2013 | Stone et al. |
| 8,435,264 B2 | 5/2013 | Sojka et al. |
| 8,439,976 B2 | 5/2013 | Albertorio et al. |
| 8,444,672 B2 | 5/2013 | Foerster |
| 8,444,674 B2 | 5/2013 | Kaplan |
| 8,454,704 B2 | 6/2013 | Frushell et al. |
| 8,460,338 B2 | 6/2013 | Goraltchouk et al. |
| 8,460,340 B2 | 6/2013 | Sojka et al. |
| 8,460,379 B2 | 6/2013 | Albertorio et al. |
| 8,469,998 B2 | 6/2013 | Sojka et al. |
| 8,491,600 B2 | 7/2013 | McDevitt et al. |
| 8,512,340 B2 | 8/2013 | Easley et al. |
| 8,518,087 B2 | 8/2013 | Lopez et al. |
| 8,523,902 B2 | 9/2013 | Heaven et al. |
| 8,545,535 B2 | 10/2013 | Hirotsuka et al. |
| 8,545,536 B2 | 10/2013 | Mayer et al. |
| 8,556,911 B2 | 10/2013 | Mehta et al. |
| 8,562,645 B2 | 10/2013 | Stone et al. |
| 8,591,578 B2 | 11/2013 | Albertorio et al. |
| 8,597,333 B2 | 12/2013 | Morgenstern Lopez et al. |
| 8,613,756 B2 | 12/2013 | Lizardi et al. |
| 8,623,051 B2 | 1/2014 | Bojarski et al. |
| 8,632,568 B2 | 1/2014 | Miller et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,834,543 B2 | 9/2014 | McDevitt et al. |
| 8,936,620 B2 | 1/2015 | Kaiser et al. |
| 8,986,345 B2 | 3/2015 | Denham et al. |
| 9,072,530 B2 | 7/2015 | Mehta et al. |
| 9,370,350 B2 | 6/2016 | Norton |
| 9,445,803 B2 | 9/2016 | Marchand et al. |
| 9,451,938 B2 | 9/2016 | Overes et al. |
| 2001/0002436 A1 | 5/2001 | Bowman et al. |
| 2001/0027320 A1 | 10/2001 | Sasso |
| 2001/0049529 A1 | 12/2001 | Cachia et al. |
| 2002/0019635 A1 | 2/2002 | Wenstrom et al. |
| 2002/0040241 A1 | 4/2002 | Jarvinen |
| 2002/0052649 A1 | 5/2002 | Greenhalgh |
| 2002/0087166 A1 | 7/2002 | Brock et al. |
| 2002/0115999 A1 | 8/2002 | McDevitt et al. |
| 2002/0147456 A1 | 10/2002 | Diduch et al. |
| 2002/0183758 A1 | 12/2002 | Middleton et al. |
| 2002/0188301 A1 | 12/2002 | Dallara et al. |
| 2003/0004545 A1 | 1/2003 | Burkhart et al. |
| 2003/0032961 A1 | 2/2003 | Pelo et al. |
| 2003/0065361 A1 | 4/2003 | Dreyfuss |
| 2003/0139752 A1 | 7/2003 | Pasricha et al. |
| 2003/0176919 A1 | 9/2003 | Schmieding |
| 2003/0195563 A1 | 10/2003 | Foerster |
| 2003/0195564 A1 | 10/2003 | Tran et al. |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0049194 A1 | 3/2004 | Harvie et al. |
| 2004/0060409 A1 | 4/2004 | Leung et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0093031 A1 | 5/2004 | Burkhart et al. |
| 2004/0138706 A1 | 7/2004 | Abrams et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0220573 A1 | 11/2004 | McDevitt et al. |
| 2004/0220593 A1 | 11/2004 | Greenhalgh |
| 2004/0249393 A1 | 12/2004 | Weisel et al. |
| 2004/0260300 A1 | 12/2004 | Gorensek et al. |
| 2004/0267277 A1 | 12/2004 | Zannis et al. |
| 2004/0267317 A1 | 12/2004 | Higgins et al. |
| 2005/0004644 A1 | 1/2005 | Kelsch et al. |
| 2005/0015153 A1 | 1/2005 | Goble et al. |
| 2005/0033362 A1 | 2/2005 | Grafton |
| 2005/0038427 A1 | 2/2005 | Perriello et al. |
| 2005/0049592 A1 | 3/2005 | Keith et al. |
| 2005/0049681 A1 | 3/2005 | Greenhalgh et al. |
| 2005/0070906 A1 | 3/2005 | Clark et al. |
| 2005/0075668 A1 | 4/2005 | Lizardi |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0147478 A1 | 7/2005 | Greenberg |
| 2005/0149122 A1 | 7/2005 | McDevitt et al. |
| 2005/0171569 A1 | 8/2005 | Girard et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0245932 A1 | 11/2005 | Fanton et al. |
| 2005/0251159 A1 | 11/2005 | Ewers et al. |
| 2005/0251208 A1 | 11/2005 | Elmer et al. |
| 2005/0261604 A1 | 11/2005 | Stephens et al. |
| 2005/0277986 A1 | 12/2005 | Foerster et al. |
| 2005/0283156 A1 | 12/2005 | Schmieding et al. |
| 2005/0283171 A1 | 12/2005 | Bellafiore et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0004410 A1 | 1/2006 | Nobis et al. |
| 2006/0015108 A1 | 1/2006 | Bonutti |
| 2006/0015110 A1 | 1/2006 | Pepper |
| 2006/0030884 A1 | 2/2006 | Yeung et al. |
| 2006/0052788 A1 | 3/2006 | Thelen et al. |
| 2006/0074434 A1 | 4/2006 | Wenstrom et al. |
| 2006/0079904 A1 | 4/2006 | Thal |
| 2006/0081553 A1 | 4/2006 | Patterson et al. |
| 2006/0100631 A1 | 5/2006 | Sullivan et al. |
| 2006/0106423 A1 | 5/2006 | Weisel et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0217762 A1 | 9/2006 | Maahs et al. |
| 2006/0235413 A1 | 10/2006 | Denham et al. |
| 2006/0241675 A1 | 10/2006 | Johnson et al. |
| 2006/0247641 A1 | 11/2006 | Re et al. |

(56) References Cited

U.S. PATENT DOCUMENTS

| | | |
|---|---|---|
| 2006/0247642 A1 | 11/2006 | Stone et al. |
| 2006/0265010 A1 | 11/2006 | Paraschac et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293689 A1 | 12/2006 | Miller et al. |
| 2007/0005068 A1 | 1/2007 | Sklar |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0060922 A1 | 3/2007 | Dreyfuss |
| 2007/0093840 A1 | 4/2007 | Pacelli et al. |
| 2007/0093858 A1 | 4/2007 | Gambale et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0167950 A1 | 7/2007 | Tauro et al. |
| 2007/0185532 A1 | 8/2007 | Stone et al. |
| 2007/0191853 A1 | 8/2007 | Stone |
| 2007/0203498 A1 | 8/2007 | Gerber et al. |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0270889 A1 | 11/2007 | Conlon et al. |
| 2007/0270907 A1 | 11/2007 | Stokes et al. |
| 2007/0276392 A1 | 11/2007 | Beyar et al. |
| 2007/0288023 A1 | 12/2007 | Pellegrino et al. |
| 2007/0288027 A1 | 12/2007 | Grafton et al. |
| 2007/0288031 A1 | 12/2007 | Dreyfuss et al. |
| 2007/0293879 A1 | 12/2007 | Baker et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1 | 3/2008 | Stone et al. |
| 2008/0071282 A1 | 3/2008 | Assell et al. |
| 2008/0082127 A1 | 4/2008 | Stone et al. |
| 2008/0082128 A1 | 4/2008 | Stone |
| 2008/0086138 A1 | 4/2008 | Stone et al. |
| 2008/0103528 A1 | 5/2008 | Zirps et al. |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1 | 6/2008 | Stone et al. |
| 2008/0140093 A1 | 6/2008 | Stone et al. |
| 2008/0140116 A1 | 6/2008 | Bonutti |
| 2008/0140123 A1 | 6/2008 | Ferree |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0275453 A1 | 11/2008 | Lafosse et al. |
| 2008/0275469 A1 | 11/2008 | Fanton et al. |
| 2008/0294177 A1 | 11/2008 | To et al. |
| 2008/0306483 A1 | 12/2008 | Tannarone |
| 2008/0306510 A1 | 12/2008 | Stchur |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018554 A1 | 1/2009 | Thorne et al. |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0082807 A1 | 3/2009 | Miller et al. |
| 2009/0099554 A1 | 4/2009 | Forster et al. |
| 2009/0099598 A1 | 4/2009 | McDevitt et al. |
| 2009/0105775 A1 | 4/2009 | Mitchell et al. |
| 2009/0112214 A1 | 4/2009 | Philippon et al. |
| 2009/0112270 A1 | 4/2009 | Lunn et al. |
| 2009/0112770 A1 | 4/2009 | Schmidt et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0143819 A1 | 6/2009 | D'Agostino |
| 2009/0149858 A1 | 6/2009 | Fanelli et al. |
| 2009/0157081 A1 | 6/2009 | Homan et al. |
| 2009/0157124 A1 | 6/2009 | Ferragamo et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0192545 A1 | 7/2009 | Workman |
| 2009/0194446 A1 | 8/2009 | Miller et al. |
| 2009/0198258 A1 | 8/2009 | Workman |
| 2009/0210047 A1 | 8/2009 | Amplatz et al. |
| 2009/0216238 A1 | 8/2009 | Stark |
| 2009/0216243 A1 | 8/2009 | Re |
| 2009/0221922 A1 | 9/2009 | Lee et al. |
| 2009/0222013 A1 | 9/2009 | Graf et al. |
| 2009/0222041 A1 | 9/2009 | Foerster |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0240335 A1 | 9/2009 | Arcenio et al. |
| 2009/0248029 A1 | 10/2009 | Paulos |
| 2009/0248068 A1 | 10/2009 | Lombardo et al. |
| 2009/0265002 A1 | 10/2009 | Re et al. |
| 2009/0292321 A1 | 11/2009 | Collette |
| 2009/0299386 A1 | 12/2009 | Meridew |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0312794 A1 | 12/2009 | Nason et al. |
| 2009/0318961 A1 | 12/2009 | Stone et al. |
| 2009/0326538 A1 | 12/2009 | Sennett et al. |
| 2010/0004683 A1 | 1/2010 | Hoof et al. |
| 2010/0023056 A1 | 1/2010 | Johansson et al. |
| 2010/0049196 A1 | 2/2010 | Re |
| 2010/0049202 A1 | 2/2010 | Re |
| 2010/0049203 A1 | 2/2010 | Re |
| 2010/0049213 A1 | 2/2010 | Serina et al. |
| 2010/0057045 A1 | 3/2010 | Albritton, IV et al. |
| 2010/0063542 A1 | 3/2010 | van der Burg et al. |
| 2010/0069925 A1 | 3/2010 | Friedman et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0094314 A1 | 4/2010 | Hernlund et al. |
| 2010/0094355 A1 | 4/2010 | Trenhaile |
| 2010/0094425 A1 | 4/2010 | Bentley et al. |
| 2010/0100127 A1 | 4/2010 | Trenhaile |
| 2010/0114162 A1 | 5/2010 | Bojarski et al. |
| 2010/0121332 A1 | 5/2010 | Crainich et al. |
| 2010/0121333 A1 | 5/2010 | Crainich et al. |
| 2010/0121348 A1 | 5/2010 | van der Burg et al. |
| 2010/0121349 A1 | 5/2010 | Meier et al. |
| 2010/0137679 A1 | 6/2010 | Lashinski et al. |
| 2010/0145341 A1 | 6/2010 | Ranck et al. |
| 2010/0145384 A1 | 6/2010 | Stone et al. |

(56) References Cited

U.S. PATENT DOCUMENTS

| | | |
|---|---|---|
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0191283 A1 | 7/2010 | Foerster et al. |
| 2010/0198258 A1 | 8/2010 | Heaven et al. |
| 2010/0211075 A1 | 8/2010 | Stone |
| 2010/0222812 A1 | 9/2010 | Stone et al. |
| 2010/0222881 A1 | 9/2010 | Prewett et al. |
| 2010/0234947 A1 | 9/2010 | Ben Rubi et al. |
| 2010/0241121 A1 | 9/2010 | Logan et al. |
| 2010/0249786 A1 | 9/2010 | Schmieding et al. |
| 2010/0251861 A1 | 10/2010 | Sixto, Jr. et al. |
| 2010/0262146 A1 | 10/2010 | Tulkis |
| 2010/0262184 A1 | 10/2010 | Dreyfuss |
| 2010/0268275 A1 | 10/2010 | Stone et al. |
| 2010/0286694 A1 | 11/2010 | Rio et al. |
| 2010/0292713 A1 | 11/2010 | Cohn et al. |
| 2010/0292731 A1 | 11/2010 | Sittings et al. |
| 2010/0292732 A1 | 11/2010 | Hirotsuka et al. |
| 2010/0292792 A1 | 11/2010 | Stone et al. |
| 2010/0298878 A1 | 11/2010 | Leung et al. |
| 2010/0298879 A1 | 11/2010 | Leung et al. |
| 2010/0305576 A1 | 12/2010 | Ferguson et al. |
| 2010/0305709 A1 | 12/2010 | Metzger et al. |
| 2010/0318122 A1 | 12/2010 | Leung et al. |
| 2011/0009902 A1 | 1/2011 | Leung et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0046682 A1 | 2/2011 | Stephan et al. |
| 2011/0054526 A1 | 3/2011 | Stone et al. |
| 2011/0071545 A1 | 3/2011 | Pamichev et al. |
| 2011/0071549 A1 | 3/2011 | Caborn et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0093010 A1 | 4/2011 | Genova et al. |
| 2011/0098727 A1 | 4/2011 | Kaiser et al. |
| 2011/0098728 A1 | 4/2011 | McDevitt et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0152929 A1 | 6/2011 | McDevitt et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224726 A1 | 9/2011 | Lombardo et al. |
| 2011/0224799 A1 | 9/2011 | Stone |
| 2011/0238113 A1 | 9/2011 | Fanton et al. |
| 2011/0264138 A1 | 10/2011 | Avelar et al. |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0276090 A1 | 11/2011 | Berndt et al. |
| 2011/0295279 A1 | 12/2011 | Stone et al. |
| 2011/0301621 A1 | 12/2011 | Oren et al. |
| 2011/0301622 A1 | 12/2011 | Oren et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053629 A1 | 3/2012 | Reiser et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0130424 A1 | 5/2012 | Sengun et al. |
| 2012/0136388 A1 | 5/2012 | Odermatt et al. |
| 2012/0143221 A1 | 6/2012 | Weisel et al. |
| 2012/0150203 A1 | 6/2012 | Brady et al. |
| 2012/0150223 A1 | 6/2012 | Manos et al. |
| 2012/0150297 A1 | 6/2012 | Denham et al. |
| 2012/0150301 A1 | 6/2012 | Gamache et al. |
| 2012/0160050 A1 | 6/2012 | Nishio et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203231 A1 | 8/2012 | Long |
| 2012/0203288 A1 | 8/2012 | Lange et al. |
| 2012/0209325 A1 | 8/2012 | Gagliano et al. |
| 2012/0239085 A1 | 9/2012 | Schlotterback et al. |
| 2012/0239086 A1 | 9/2012 | Reznik et al. |
| 2012/0245585 A1 | 9/2012 | Kaiser et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0006276 A1 | 1/2013 | Lantz et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0103083 A1 | 4/2013 | Baird |
| 2013/0103084 A1 | 4/2013 | Pamichev et al. |
| 2013/0110165 A1 | 5/2013 | Burkhart et al. |
| 2013/0116730 A1 | 5/2013 | Denham et al. |
| 2013/0131722 A1 | 5/2013 | Marchand et al. |
| 2013/0138152 A1 | 5/2013 | Stone et al. |
| 2013/0144334 A1 | 6/2013 | Bouduban et al. |
| 2013/0144338 A1 | 6/2013 | Stone et al. |
| 2013/0158596 A1 | 6/2013 | Miller et al. |
| 2013/0158601 A1 | 6/2013 | Stone et al. |
| 2013/0165972 A1 | 6/2013 | Sullivan |
| 2013/0178898 A1 | 7/2013 | Arnett et al. |
| 2013/0184748 A1 | 7/2013 | Sojka et al. |
| 2013/0190818 A1 | 7/2013 | Norton |
| 2013/0190819 A1 | 7/2013 | Norton |
| 2013/0204298 A1 | 8/2013 | Graul et al. |
| 2013/0237997 A1 | 9/2013 | Arai et al. |
| 2013/0238025 A1 | 9/2013 | Howard et al. |
| 2013/0245700 A1 | 9/2013 | Choinski |
| 2013/0267998 A1 | 10/2013 | Vijay et al. |
| 2013/0268000 A1 | 10/2013 | Harner et al. |

(56) References Cited

U.S. PATENT DOCUMENTS

| | | |
|---|---|---|
| 2013/0296893 A1 | 11/2013 | Dean et al. |
| 2013/0296931 A1 | 11/2013 | Sengun |
| 2013/0296934 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0081322 A1 | 3/2014 | Sengun et al. |
| 2014/0135835 A1 | 5/2014 | Stone et al. |
| 2014/0163679 A1 | 6/2014 | Re et al. |
| 2014/0188163 A1 | 7/2014 | Sengun |
| 2014/0257382 A1 | 9/2014 | McCartney |
| 2014/0277121 A1 | 9/2014 | Pilgeram et al. |
| 2014/0316460 A1 | 10/2014 | Graul et al. |

FOREIGN PATENT DOCUMENTS

| | | |
|---|---|---|
| DE | 8903079 U1 | 5/1989 |
| DE | 4231101 A1 | 3/1994 |
| DE | 4243715 A1 | 7/1994 |
| DE | 19503504 A1 | 3/1996 |
| EP | 153831 A2 | 9/1985 |
| EP | 0232049 A1 | 8/1987 |
| EP | 0241240 A2 | 10/1987 |
| EP | 251583 | 1/1988 |
| EP | 253526 A1 | 1/1988 |
| EP | 0270704 A1 | 6/1988 |
| EP | 0318426 B1 | 2/1991 |
| EP | 0440371 A1 | 8/1991 |
| EP | 0574707 A1 | 12/1993 |
| EP | 0611551 A1 | 8/1994 |
| EP | 0673624 A2 | 9/1995 |
| EP | 1016377 A3 | 3/2001 |
| EP | 1155776 A2 | 11/2001 |
| EP | 1174584 A2 | 1/2002 |
| EP | 0834281 B1 | 3/2003 |
| EP | 1369089 A2 | 12/2003 |
| EP | 1398455 A2 | 3/2004 |
| EP | 1825817 A1 | 8/2007 |
| EP | 1568327 B1 | 11/2009 |
| EP | 2277457 A1 | 1/2011 |
| EP | 2286742 A1 | 2/2011 |
| EP | 2335603 | 6/2011 |
| EP | 2544607 A1 | 1/2013 |
| EP | 2548519 A2 | 1/2013 |
| EP | 2596755 A2 | 5/2013 |
| EP | 2662030 A1 | 11/2013 |
| EP | 2662032 A1 | 11/2013 |
| EP | 1762187 B1 | 10/2014 |
| FR | 1166884 A | 11/1958 |
| FR | 2606996 A1 | 5/1988 |
| FR | 2676638 A1 | 11/1992 |
| GB | 2093353 A | 9/1982 |
| WO | 9204874 A1 | 4/1992 |
| WO | 95011631 A1 | 5/1995 |
| WO | 9515726 A1 | 6/1995 |
| WO | 9628100 A1 | 9/1996 |
| WO | 9703615 | 2/1997 |
| WO | 9704908 A1 | 2/1997 |
| WO | 9722301 A1 | 6/1997 |
| WO | 9730649 | 8/1997 |
| WO | 98038938 A1 | 9/1998 |
| WO | 0024327 A2 | 5/2000 |
| WO | 0044291 A1 | 8/2000 |
| WO | 0128457 A1 | 4/2001 |
| WO | 0160268 A1 | 8/2001 |
| WO | 03007861 A1 | 1/2003 |
| WO | 03086221 A1 | 10/2003 |
| WO | 03092514 A1 | 11/2003 |
| WO | 2004092531 A2 | 10/2004 |
| WO | 2007/010389 A1 | 1/2007 |
| WO | 2008063915 A2 | 5/2008 |
| WO | 2008128075 A1 | 10/2008 |
| WO | 2009105880 A1 | 9/2009 |
| WO | 11060022 A2 | 5/2011 |
| WO | 2011112371 A1 | 9/2011 |
| WO | 2012034131 | 3/2012 |
| WO | 2012134999 A1 | 10/2012 |
| WO | 2012158583 A1 | 11/2012 |
| WO | 2013006820 A1 | 1/2013 |
| WO | 2014107729 A2 | 7/2014 |

OTHER PUBLICATIONS

Biomet 1 Sports Medicine: Micromax Flex Suture Anchor, (2008).
Burkinshaw, U.S. Appl. No. 60/418,545, filed Oct. 15, 2002.
Canadian Office Action for Application No. 2,811,838 dated May 22, 2014.
Canadian Office Action for Application No. 2,812,775 dated Aug. 23, 2013.
Canadian Office Action for Application No. 2768020 dated Jan. 21, 2014.
Canadian Office Action for Application No. 2773849 dated Aug. 5, 2013.
Canadian Office Action for Application No. 2811838 dated Feb. 24, 2015.
Charles McCartney, U.S. Appl. No. 13/792,982, filed Mar. 11, 2013, titled "Filamentary Fixation Device and Assembly and Method of Assembly, Manufacture and Use".
Chen et al., European Cells and Materials, vol. 16, Supp. 4, p. 7, 2008.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, Apr. 2011, 10 pages.
European Examination Report for Application No. EP14157129.9 dated Jul. 28, 2017.
European Search Report for Application No. 13178933.1 dated Sep. 25, 2015.
European Search Report, EP 10173568, dated Nov. 30, 2010.
Extended European Search Report for Application No. EP14157877 dated Jul. 4, 2016.
HHS Tube, Fort Wayne Metals Research Products Corp., 2009, 2 pages.
Insall et al., The Journal of Bone and Joint Surgery, vol. 49B, No. 2, pp. 211-228, May 1967.
International Search Report and Written Opinion for Application No. PCT/US2012/024303 dated May 24, 2012.
International Search Report PCT/US2010/042264, dated Sep. 30, 2010.
Marchand et al., U.S. Appl. No. 13/303,849, filed Nov. 23, 2011, titled "Filamentary Suture Anchor".
Partial European Search Report for U.S. Appl. No. 13/162,591 dated Aug. 14, 2015.
Partial European Search Report for Application No. EP14151822 dated May 16, 2014.
Partial European Search Report for Appln No. EP12193507 dated Jun. 30, 2017.
Partial International Search Report for Application No. PCT/US2014/069087 dated Mar. 12, 2015.
Perthes, Uber Operationen bel habitueller Schulterluxaton, Deutsch Zeitschrift fur Chirurgie, vol. 85, 1906, pp. 199-227 (English translation provided.).
Pilgeram, Kyle Craig, U.S. Appl. No. 13/588,586, filed Aug. 17, 2012, titled "Soft Tissue Fixation Devices and Methods".
Pilgeram, Kyle Craig, U.S. Appl. No. 13/588,592, filed Aug. 17, 2012, titled "Surgical Instruments and Methods of Use".
Pilgeram, Kyle Craig, U.S. Appl. No. 13/783,804, filed Mar. 4, 2013, titled "Knotless Filamentary Fixation Devices, Assemblies and Systems and Methods of Assembly and Use".
Pilgeram, Kyle Craig, U.S. Appl. No. 61/679,336, filed Aug. 3, 2012, titled "Soft Tissue Fixation Device and Methods".
U.S. Appl. No. 12/682,324, filed Sep. 7, 2010.
U.S. Appl. No. 13/070,692, filed Mar. 24, 2011.
U.S. Appl. No. 13/182,851, filed Jul. 14, 2011.
U.S. Appl. No. 13/799,773, filed Mar. 13, 2013.

(56) References Cited

OTHER PUBLICATIONS

Australian Examination Report for Application No. 2013202699 dated Feb. 21, 2014.
Boccaccini, et al., "Composite Surgical Sutures with Bioactive Glass Coating", J Biomed Mater Res Part B: Appl Biomater 67B, pp. 618-626, 2003.
Bretcanu, et al., "Bioactivity of degradable polymer sutures coated with bioactive glass", Journal of Materials Science: Materials in Medicine, vol. 15, 2004, pp. 893-899.
ConMed: Linvatec: Shoulder Restoration System Y-Knot 1 3mm All Suture Anchor, Copyright 2011 Linvatec Corporation, a subsidiary of ConMed Corporation—CBR 3057 (4 pages).
Extended European Search Report for Application No. EP 12164104 dated Jul. 11, 2012.
Extended European Search Report for Application No. EP14157129 dated Oct. 9, 2014.
Extended European Search Report for Application No. EP14159656 dated Jun. 6, 2014.
International Search Report and Written Opinion for Application No. PCT/US2014/021231 dated Jun. 25, 2014.
International Search Report and Written Opinion for Application No. PCT/US2014/069087 dated Jun. 17, 2015.
Long et al., U.S. Appl. No. 13/368,730, filed Feb. 8, 2012, titled "Flexible Microdrilling Nstrumentation, Kits and Methods".
Medtronic, The VISAO High-Speed Otologic Drill Catalog, 2007, 12 pages.
Perthes, German Surgery Periodical, vol. 85, Commermorative Publication, pp. 2-18, 1906.
Stamboulis, et al., "Mechanical properties of biodegradable polymer sutures coated with bioactive glass", Journal of Materials Science: Materials in Medicine, vol. 13, 2002, pp. 843-848.
Steiner et al., U.S. Appl. No. 13/085,882, filed Apr. 13, 2011, titled "Flexible ACL Instrumentation, Kit and Method".
Sugaya et al., Journal of Bone and Joint Surgery, vol. 85-A, No. 5, pp. 878-884, May 2003.

CAM-TYPE FEMOROACETABULAR IMPINGEMENT (FAI)
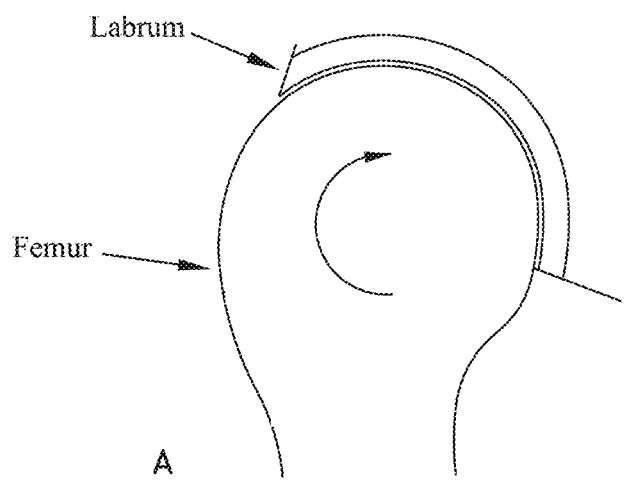
CAM INJURY TO THE LABRUM
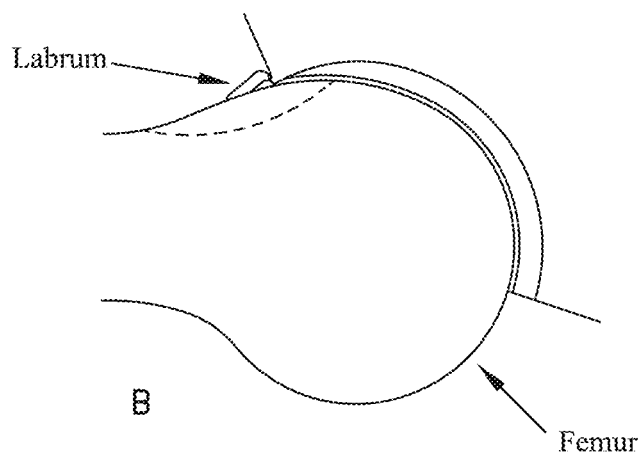
FIG. 13

PINCER-TYPE FEMOROACETABULAR IMPINGEMENT (FAI)
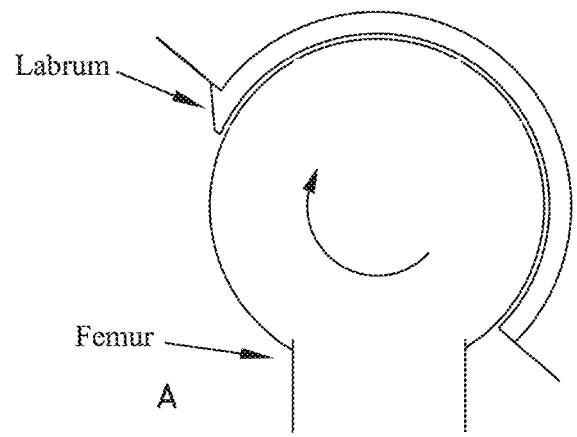
PINCER INJURY TO THE LABRUM
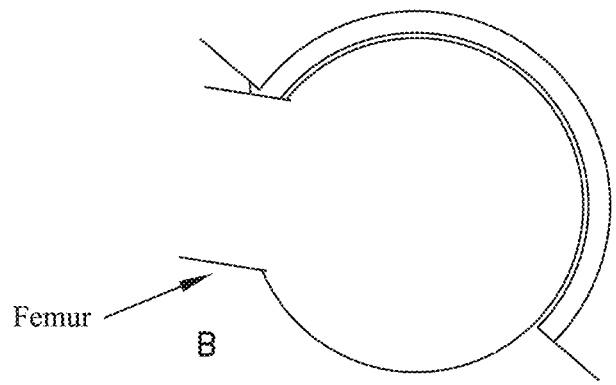
FIG. 14

PRE-DEPLOYMENT CONSTRUCTION

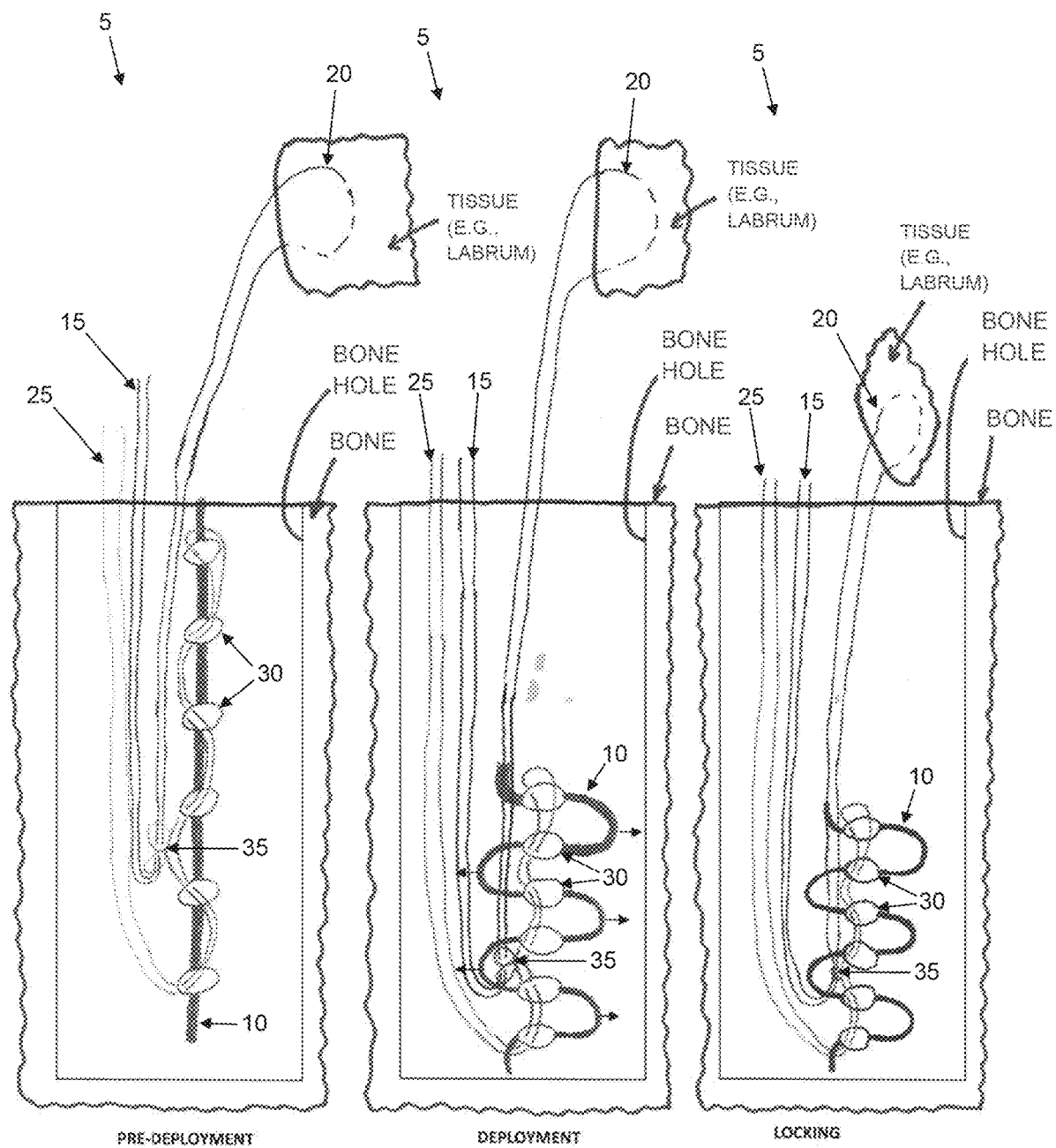

POST-DEPLOYMENT

PRE-DEPLOYMENT

POST-DEPLOYMENT

PRE-DEPLOYMENT

POST-DEPLOYMENT

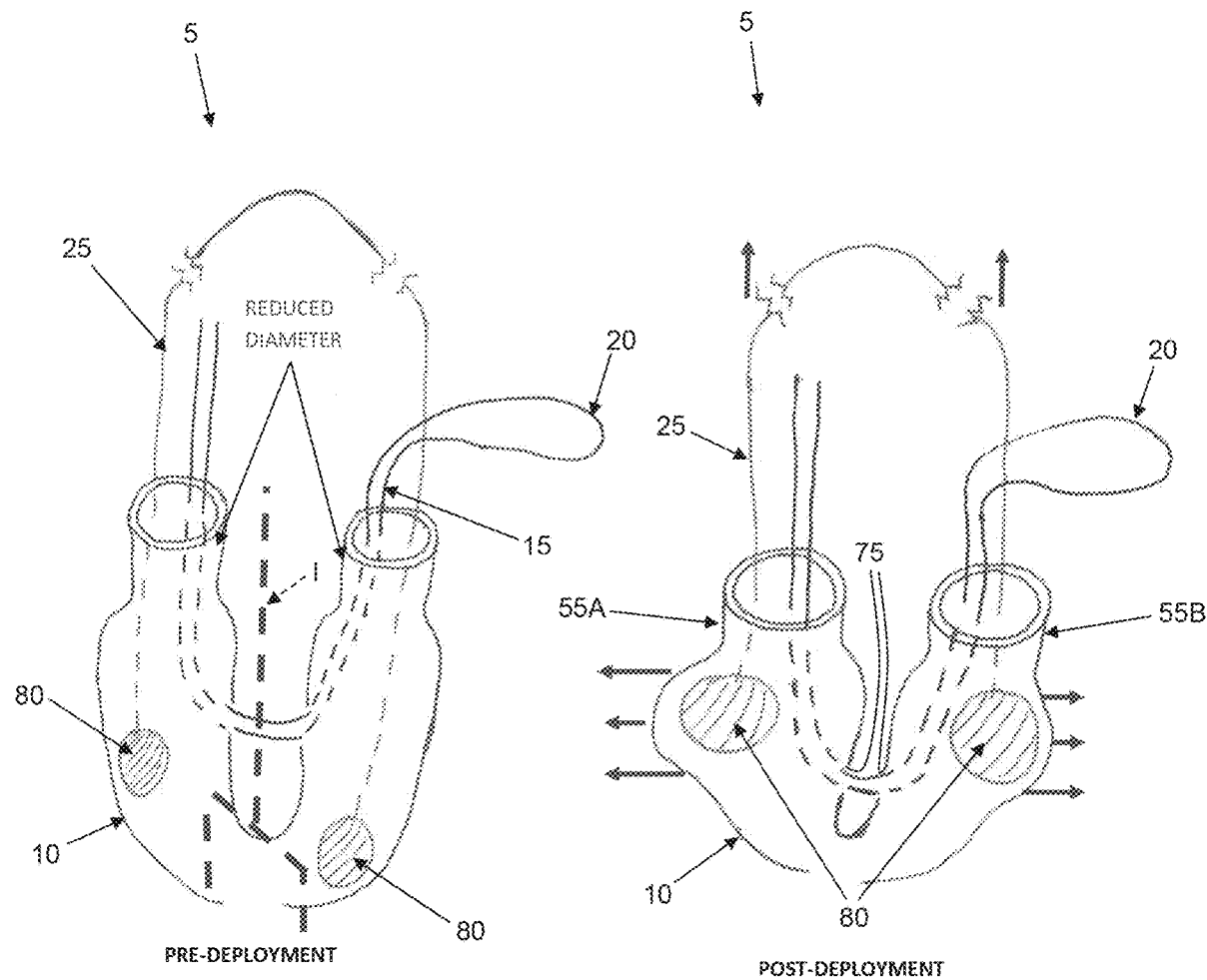
FIG. 37 · FIG. 38

Pre-Deployment

Pre-Deployment

Post-Deployment

Pre-Deployment

Post-Deployment

METHOD AND APPARATUS FOR ATTACHING TISSUE TO BONE

CROSS-REFERENCE TO RELATED APPLICATIONS

This application is a continuation of U.S. application Ser. No. 14/258,837, filed on Apr. 22, 2014, which claims the benefit of U.S. Provisional Application No. 61/814,403, filed on Apr. 22, 2013, which claims the benefit of U.S. Provisional Application No. 61/881,007, filed on Sep. 23, 2013, the disclosures of which are incorporated herein by reference.

FIELD OF THE INVENTION

This invention relates to surgical methods and apparatus in general, and more particularly to surgical methods and apparatus for treating a hip joint and other anatomy.

BACKGROUND OF THE INVENTION

The Hip Joint In General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy Of The Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating relation.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies Of The Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of labral injuries can be very painful for the patient and, if left untreated, can lead to substantial deterioration of the hip joint.

The General Trend Toward Treating Joint Pathologies Using Minimally-Invasive, And Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment For Pathologies Of The Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and hence less common in practice. Consequently, many patients are forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Re-attaching The Labrum Of The Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted when the labrum has been damaged but is still sufficiently healthy and capable of repair. The repair can occur with a labrum which is still attached to the acetabulum or after the labrum has been deliberately detached from the acetabulum (e.g., so as to allow for acetabular rim trimming to treat a pathology such as a pincer-type femoroacetabular impingement) and needs to be subsequently re-attached. See, for example, FIG. 16, which shows a normal labrum which has its base securely attached to the acetabulum, and FIG. 17, which shows a portion of the labrum (in this case the tip) detached from the acetabulum. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically repairing (e.g., re-attaching) the labrum are somewhat problematic. The present invention is intended to improve upon the current approaches for labrum repair (as well as to improve upon the current approaches for other anatomical repairs).

More particularly, current approaches for arthroscopically repairing the labrum typically use apparatus originally designed for use in re-attaching ligaments to bone. For example, one such approach utilizes a screw-type anchor, with two lengths of suture extending therefrom, and involves deploying the anchor in the acetabulum above the labrum re-attachment site. After the anchor has been deployed, one length of suture is passed either through the detached labrum or, alternatively, around the detached labrum. Then that length of suture is tied to the other length of suture so as to secure the labrum against the acetabular rim. See FIG. 18.

Unfortunately, suture anchors of the sort described above are traditionally used for re-attaching ligaments to bone and, as a result, tend to be relatively large, since they must carry the substantial pull-out forces normally associated with ligament reconstruction. However, this large anchor size is generally unnecessary for labrumre-attachment, since the labrum is not subjected to substantial forces, and the large anchor size typically causes unnecessary trauma to the patient.

Furthermore, the large size of traditional suture anchors can be problematic when the anchors are used for labrum re-attachment, since the suture anchors generally require a substantial bone mass for secure anchoring, and such a large bone mass is generally available only a substantial distance up the acetabular shelf. In addition, the large size of the suture anchors generally makes it necessary to set the suture anchor a substantial distance from the articulating surfaces of the joint, in order to ensure that the distal tip of the suture anchor does not inadvertently break through the acetabular shelf and contact the articulating surfaces of the joint. However, labral re-attachment utilizing a suture anchor set high up into the acetabular shelf creates a suture path, and hence a labral draw force, which is not directly aligned with the portion of the acetabular rim where the labrum is to be re-attached. As a result, an "indirect" draw force (also known as "eversion") is typically applied to the labrum, i.e., the labrum is drawn around the rim of the acetabulum rather than directly into the acetabulum. See FIG. 18. This can sometimes result in a problematic labral re-attachment and, ultimately, can lead to a loss of the suction seal between the labrum and femoral head, which is a desired outcome of the labral re-attachment procedure. Using suture anchors of a smaller size allows the suture anchor to be set closer to the rim of the acetabulum, which can help reduce this effect. See FIG. 19.

In addition to the foregoing, suture anchors of the sort described above typically require that a knot be tied at the surgical site in order to secure the labrum to the acetabulum. This can be time-consuming and inconvenient to effect due to the nature of the minimally-invasive, "keyhole" surgery. More particularly, and as noted above, the suture anchor typically has a suture connected thereto so that two lengths of suture extend from the suture anchor and are available to secure the labrum to the acetabulum (which receives the suture anchor). One or both of the two lengths of suture are passed through or around the labrum and then knotted to one another so as to secure the labrum to the acetabulum. However, it can be time-consuming and inconvenient to form the knot at the surgical site, given the limited access to the surgical site and the restricted work space at the surgical site.

Accordingly, a new approach is needed for arthroscopically re-attaching the labrum to the acetabulum.

It would also be desirable to provide a new approach for attaching other tissue to bone, and/or for attaching another object to bone, and/or for attaching an object to tissue other than bone (e.g., cartilage, etc.).

BRIEF SUMMARY OF THE INVENTION

The present invention provides a novel method and apparatus for re-attaching the labrum to the acetabulum.

Among other things, the present invention provides a novel suture anchor system which may be used to re-attach the labrum to the acetabulum, and/or to attach other tissue to bone.

In one preferred form of the present invention, there is provided a suture anchor system wherein a loop of suture is passed through the labrum (or other tissue) and its two free ends are slidably connected to (e.g., slidably threaded through) the body of the suture anchor. After the body of the suture anchor is advanced into the acetabulum (or other bone) and the loop of suture is tensioned so as to hold the labrum (or other tissue) in place against the acetabulum (or other bone), the body of the suture anchor is reconfigured so as to lock the suture anchor to the bone and to lock the loop of suture to the body of the suture anchor and hence secure the labrum (or other tissue) to the acetabulum (or other bone). Significantly, the present invention allows the loop of suture to be locked to the body of the suture anchor without requiring a knot to be tied at the surgical site during the procedure.

The present invention also provides a new approach for attaching other tissue to bone, and/or for attaching another object to bone, and/or for attaching an object to tissue other than bone (e.g., cartilage, etc.).

In one form of the present invention, there is provided apparatus for securing a first object to a second object, said apparatus comprising:

an anchor body which is longitudinally and laterally deformable; and a working suture which is connected to said anchor body;

said anchor body and said working suture being configured such that, when at least one of said anchor body and said working suture receives a repair suture which is connected to the first object, and said anchor body is thereafter disposed in a hole in the second object, applying tension to said working suture secures said anchor body to the second object and secures said repair suture to said anchor body without requiring that a knot be tied after said anchor body is disposed in the hole in the second object.

In another form of the present invention, there is provided a method for securing a first object to a second object, said method comprising:

providing apparatus comprising:
  an anchor body which is longitudinally and laterally deformable; and
  a working suture which is connected to said anchor body;
  said anchor body and said working suture being configured such that, when at least one of said anchor body and said working suture receives a repair suture which is connected to the first object, and said anchor body is thereafter disposed in a hole in the second object, applying tension to said working suture secures said anchor body to the second object and secures said repair suture to said anchor body without requiring that a knot be tied after said anchor body is disposed in the hole in the second object;

passing the repair suture through the first object
passing the repair suture through at least one of said anchor body and said working suture;
disposing said anchor body in a hole in the second object; and
applying tension to said working suture to secure said anchor body to the second object and secure said repair suture to said anchor body without requiring that a knot be tied after said anchor body is disposed in the hole in the second object.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (i.e., cam-type FAI);
FIG. 14 is a schematic view showing pincer-type femoroacetabular impingement (i.e., pincer-type FAI);
FIGS. 20-26 show one preferred suture anchor system formed in accordance with the present invention;
FIGS. 37 and 38 show another preferred suture anchor system formed in accordance with the present invention.

DETAILED DESCRIPTION OF THE PREFERRED EMBODIMENTS

Figure 1A:
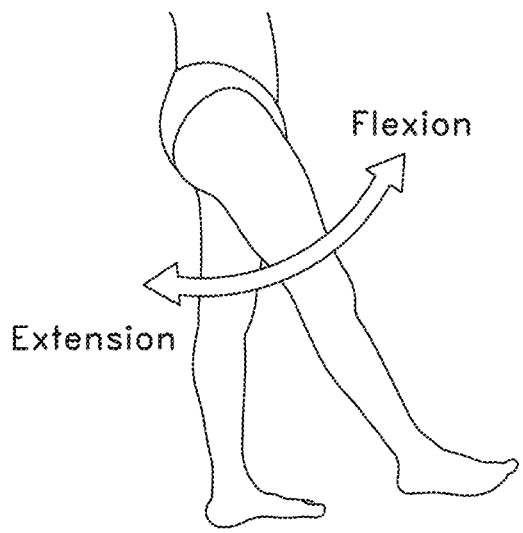
FIGS. 1A-1D are schematic views showing various aspects of hip motion.
Figure 1B:
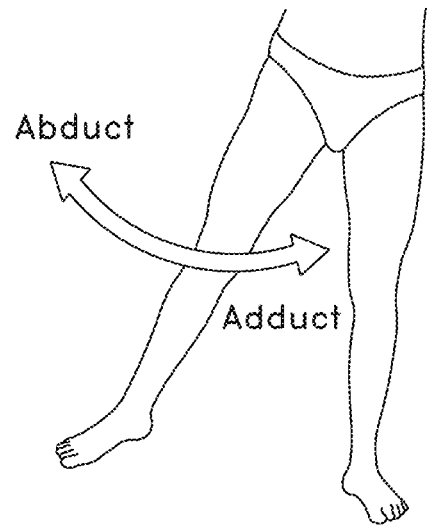
Figure 1C:
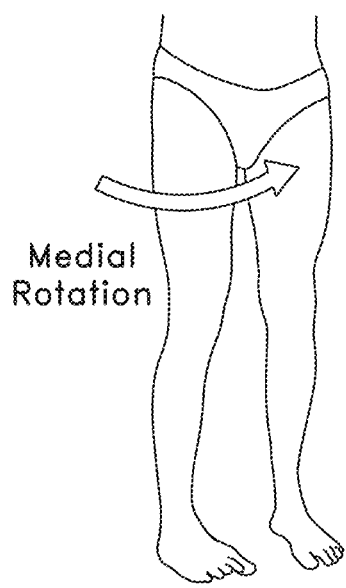
Figure 1D:
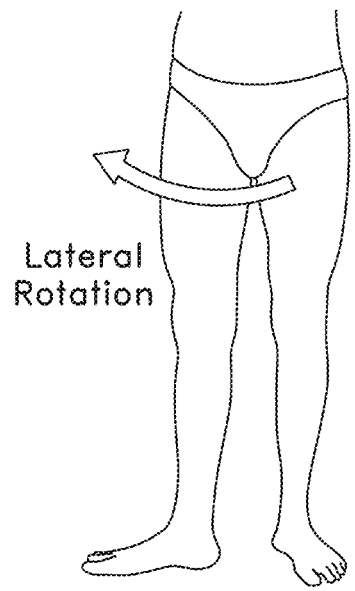
Figure 2:
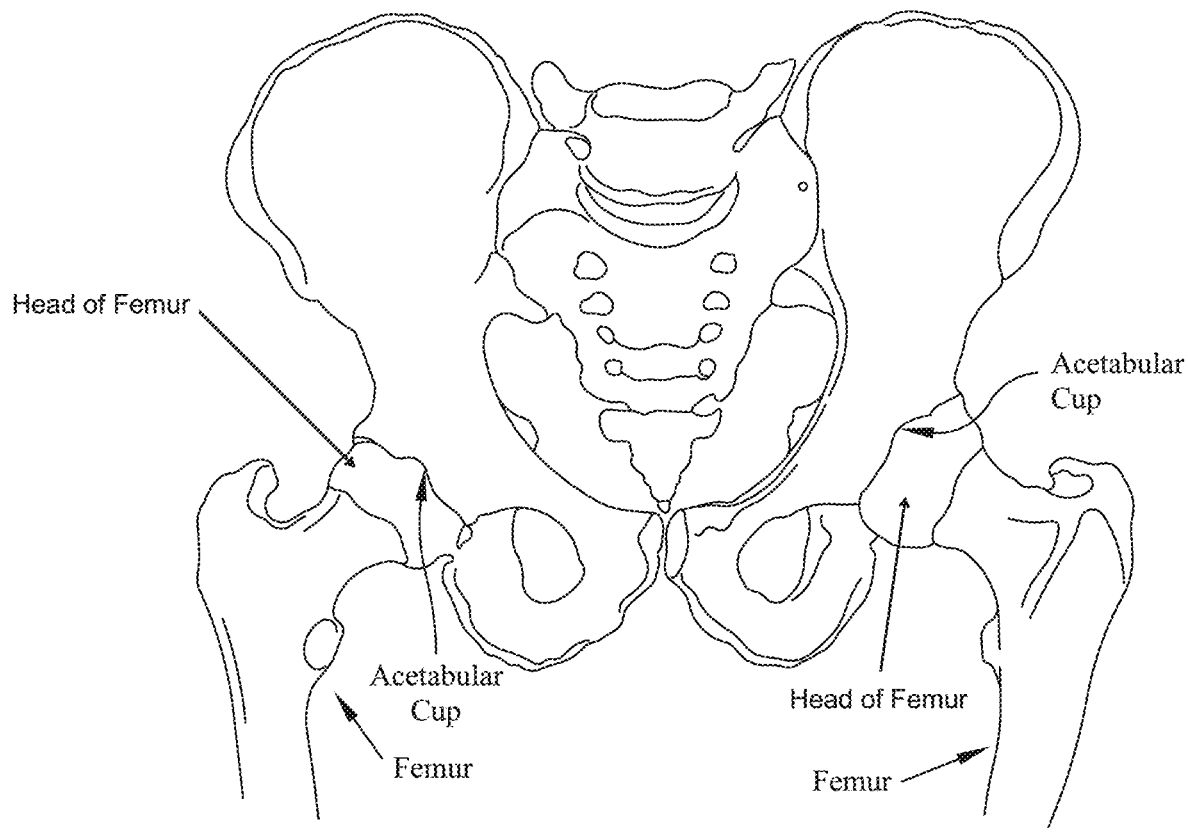
FIG. 2 is a schematic view showing bone structures in the region of the hip joint.
Figure 3:
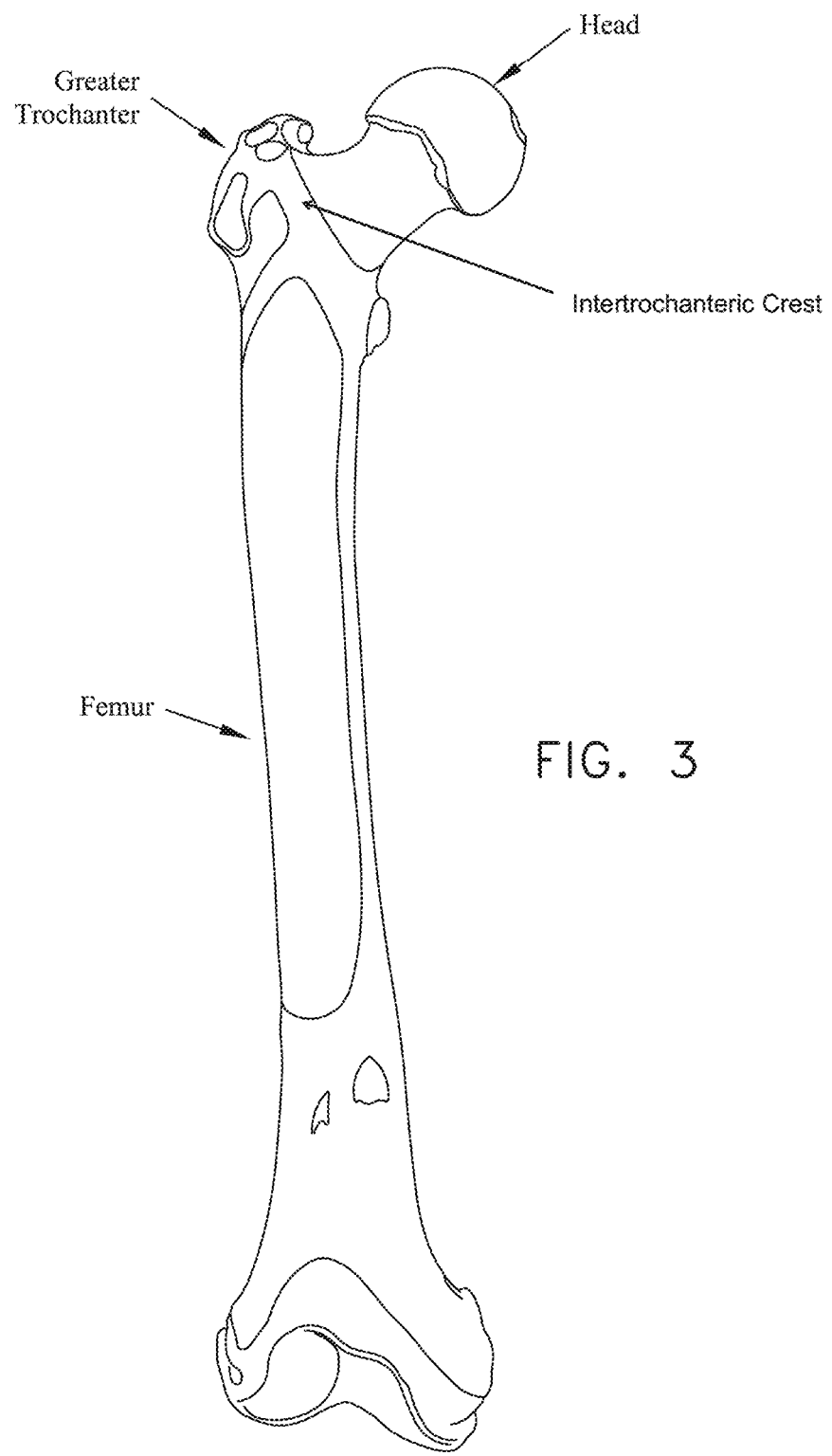
FIG. 3 is a schematic anterior view of the femur.
Figure 4:
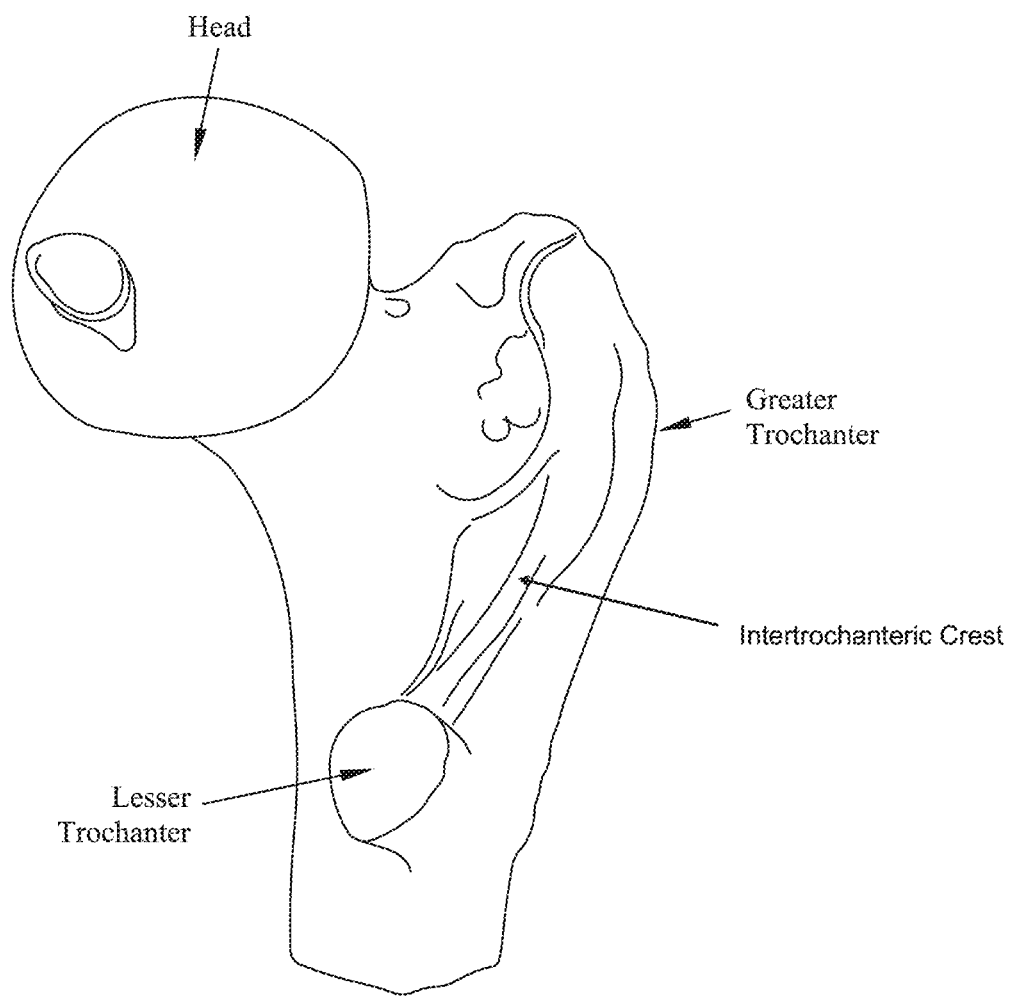
FIG. 4 is a schematic posterior view of the top end of the femur.
Figure 5:
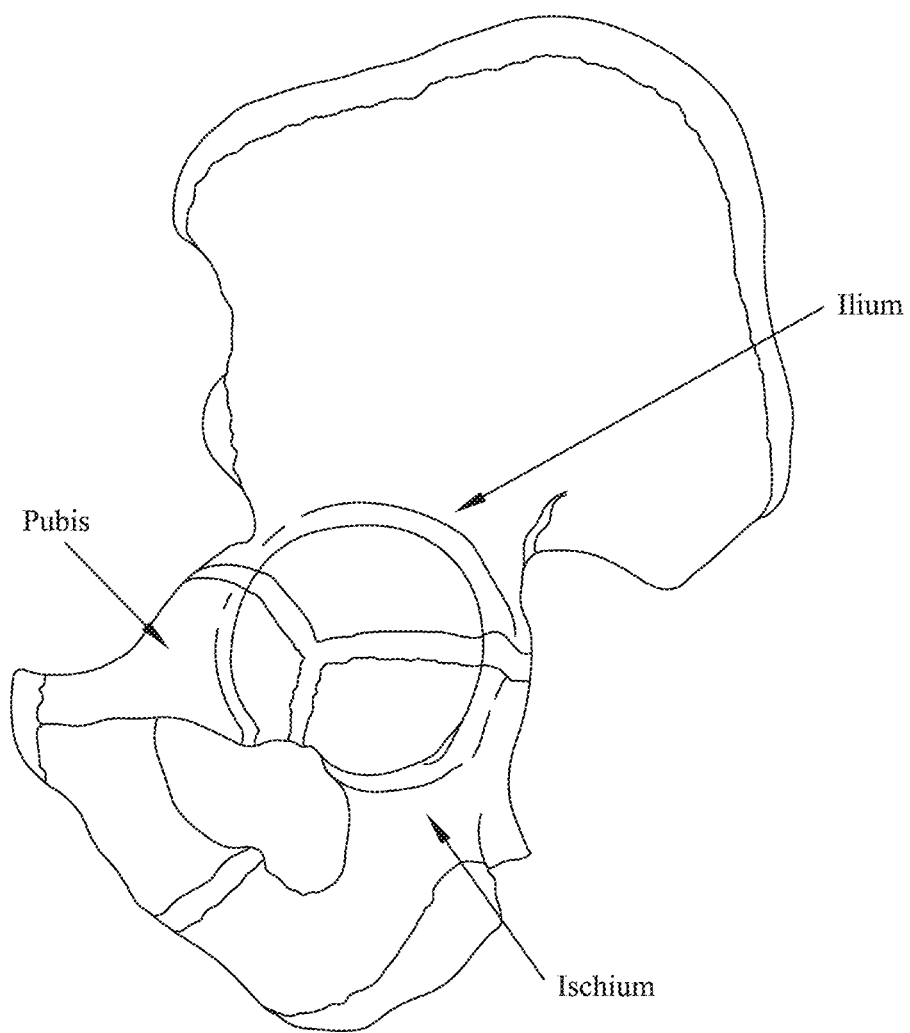
FIG. 5 is a schematic view of the pelvis.
Figure 6:
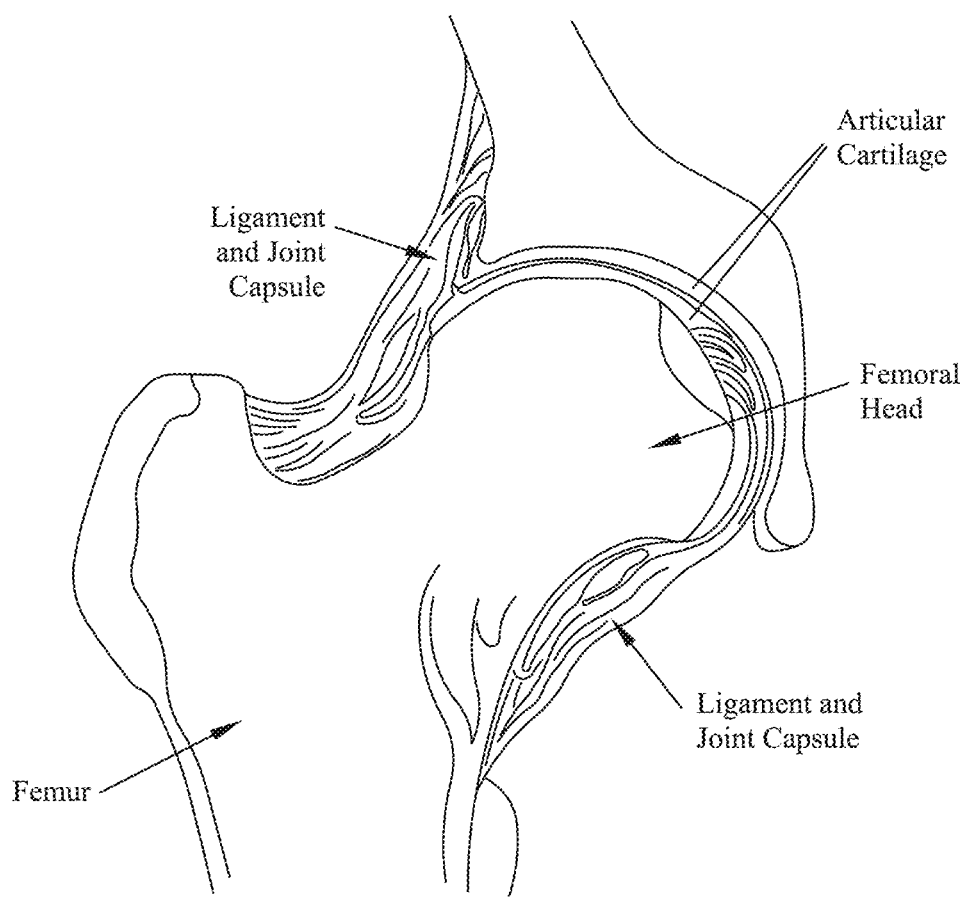
FIGS. 6-12 are schematic views showing bone and soft tissue structures in the region of the hip joint.
Figure 7:
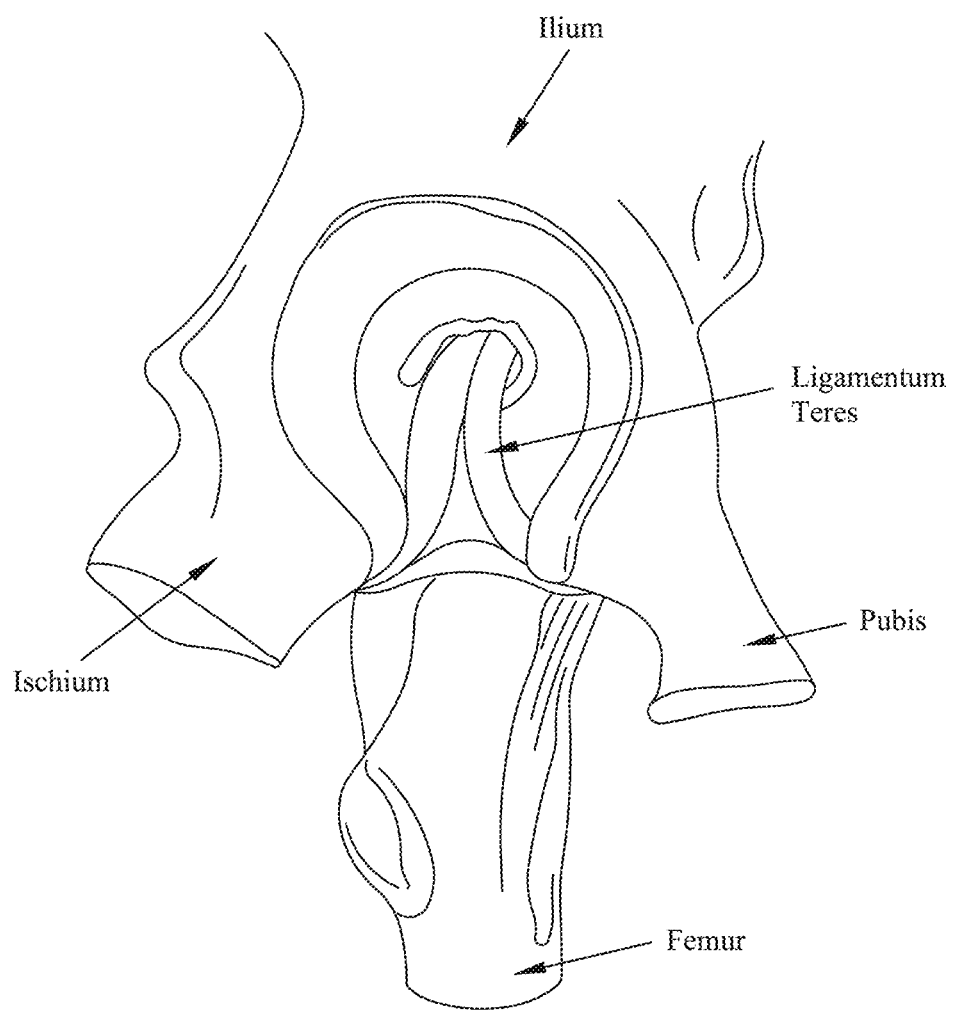
Figure 8:
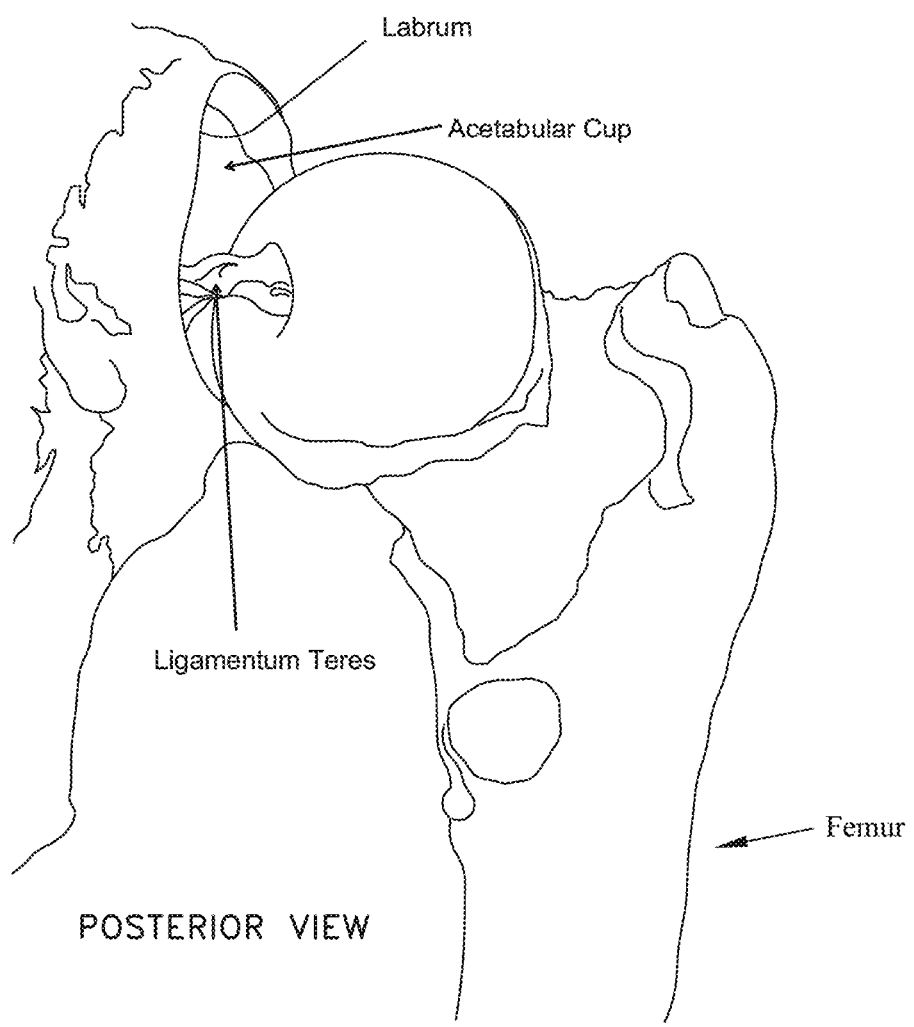
Figure 9:
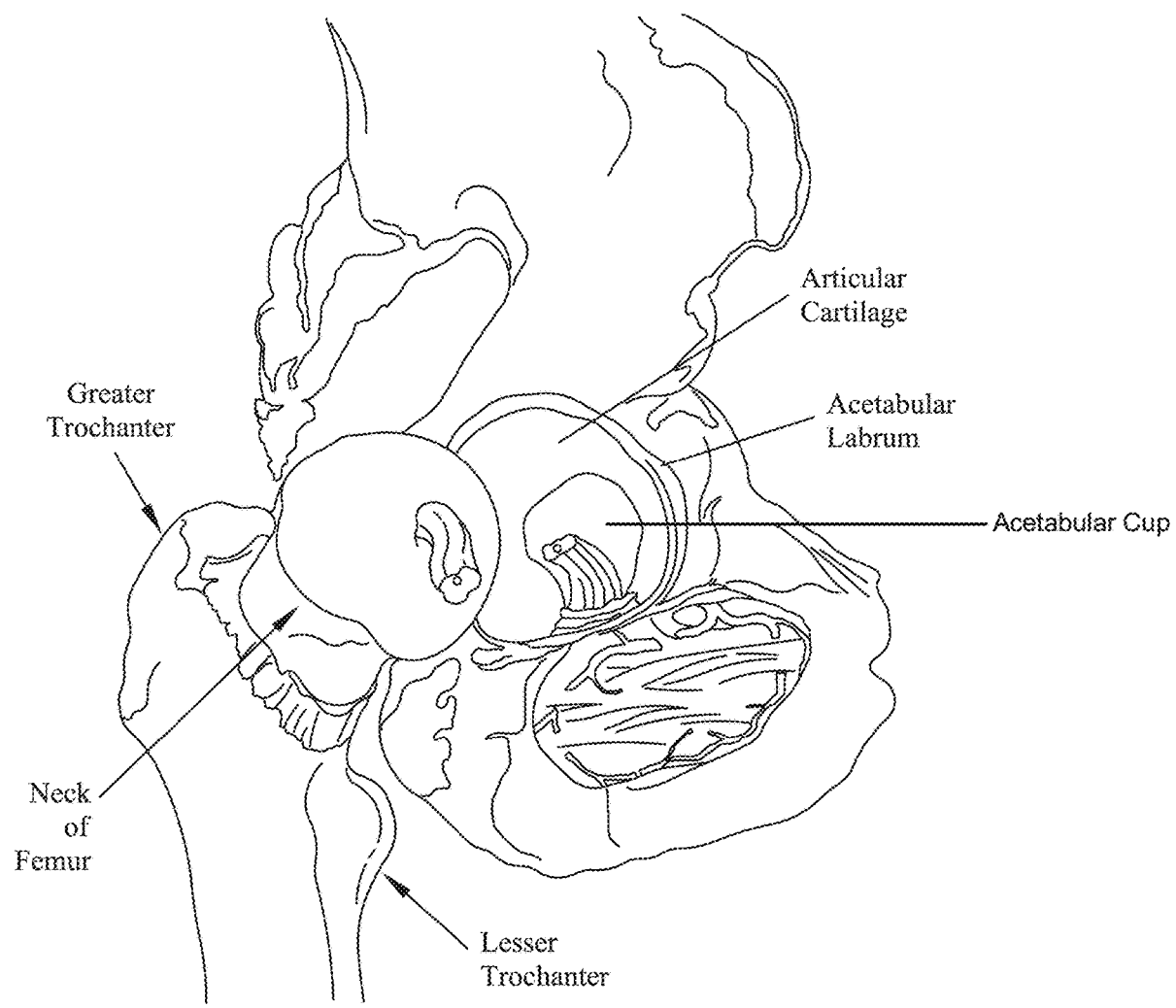
Figure 10:
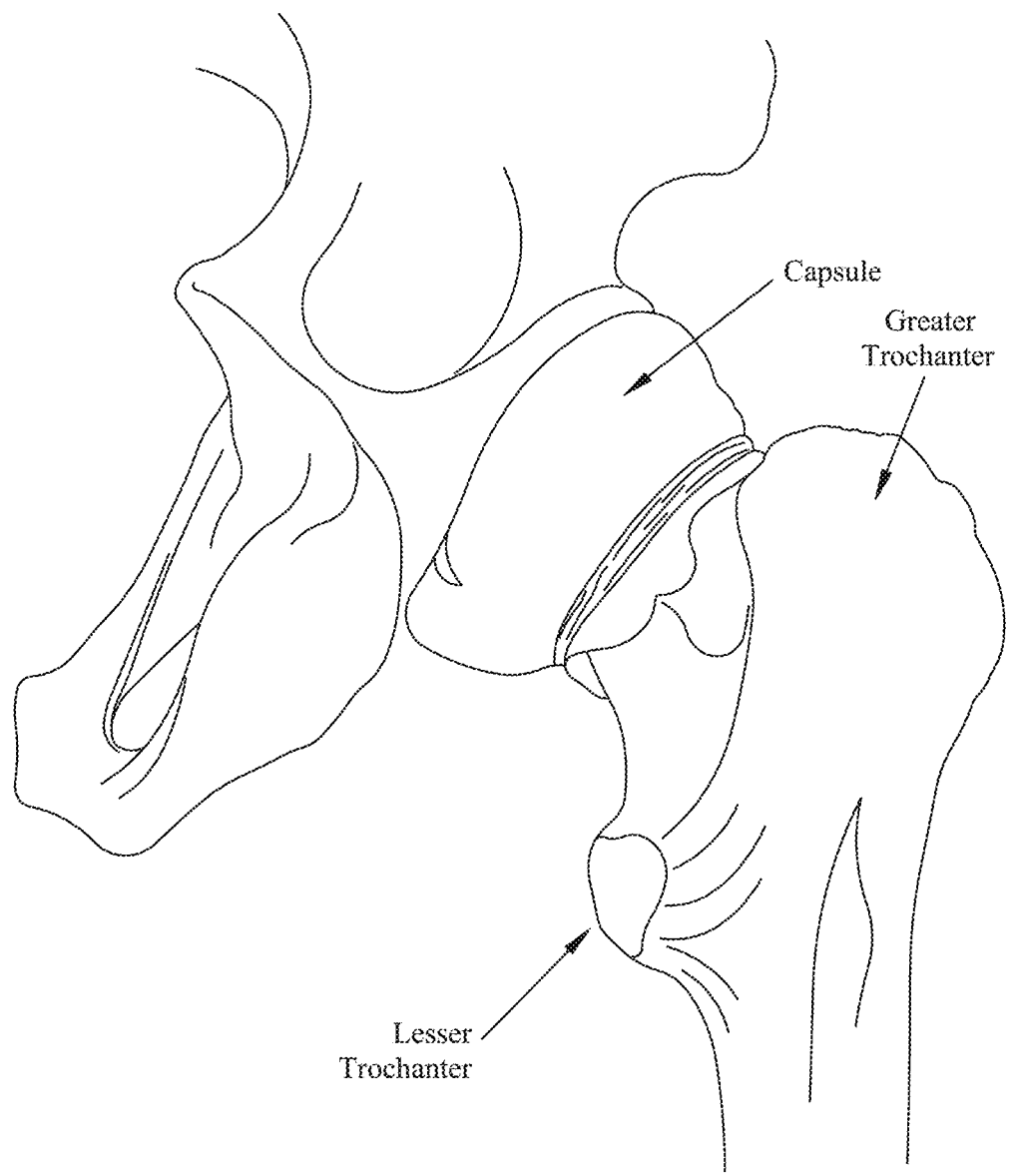
Figure 11:
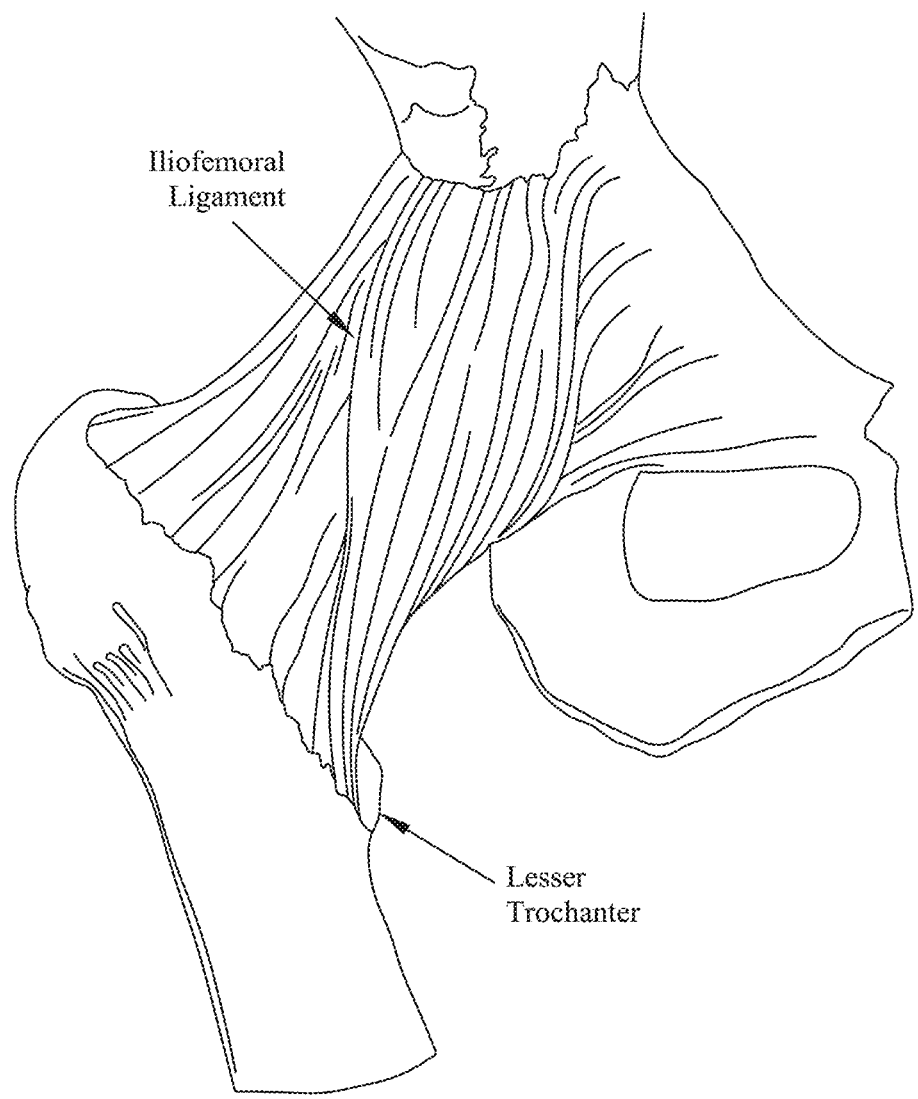
Figure 12:
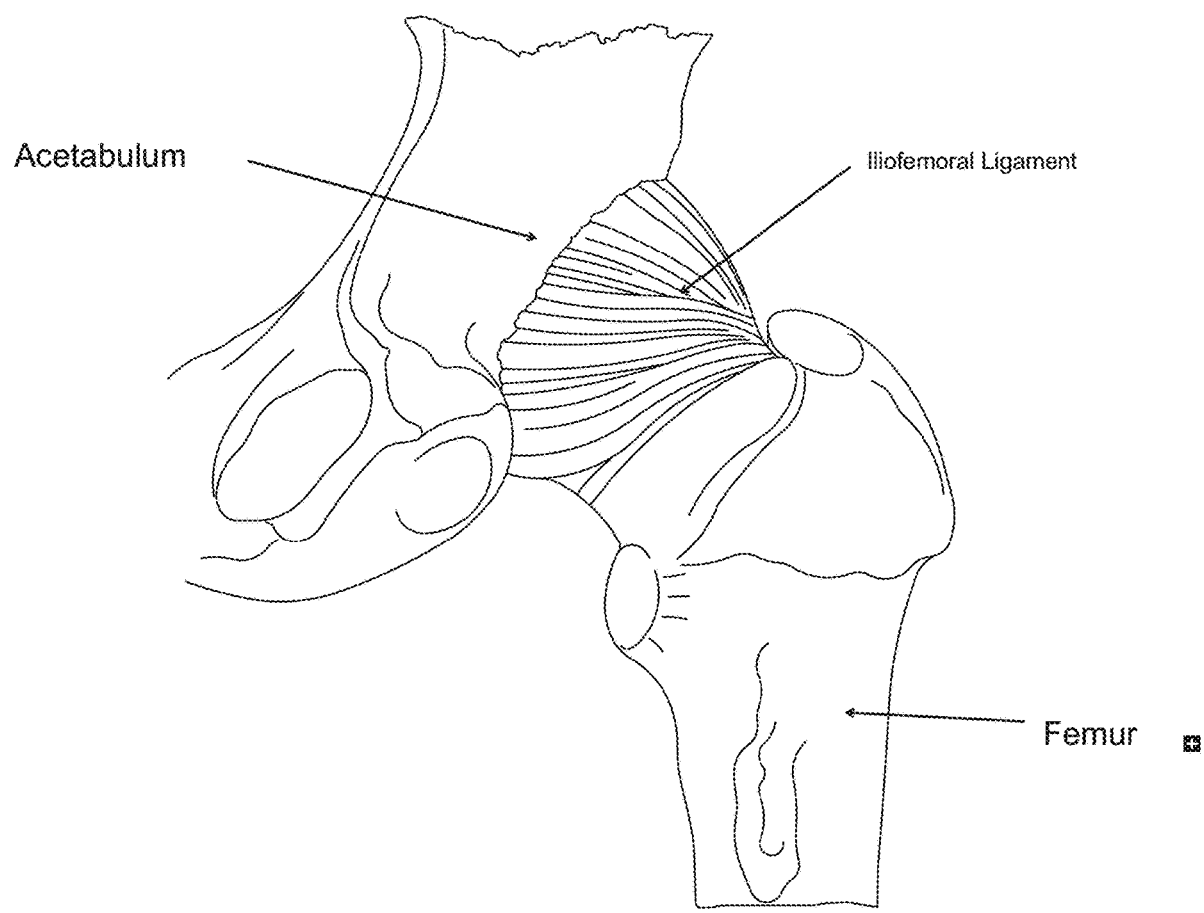
Figure 15:
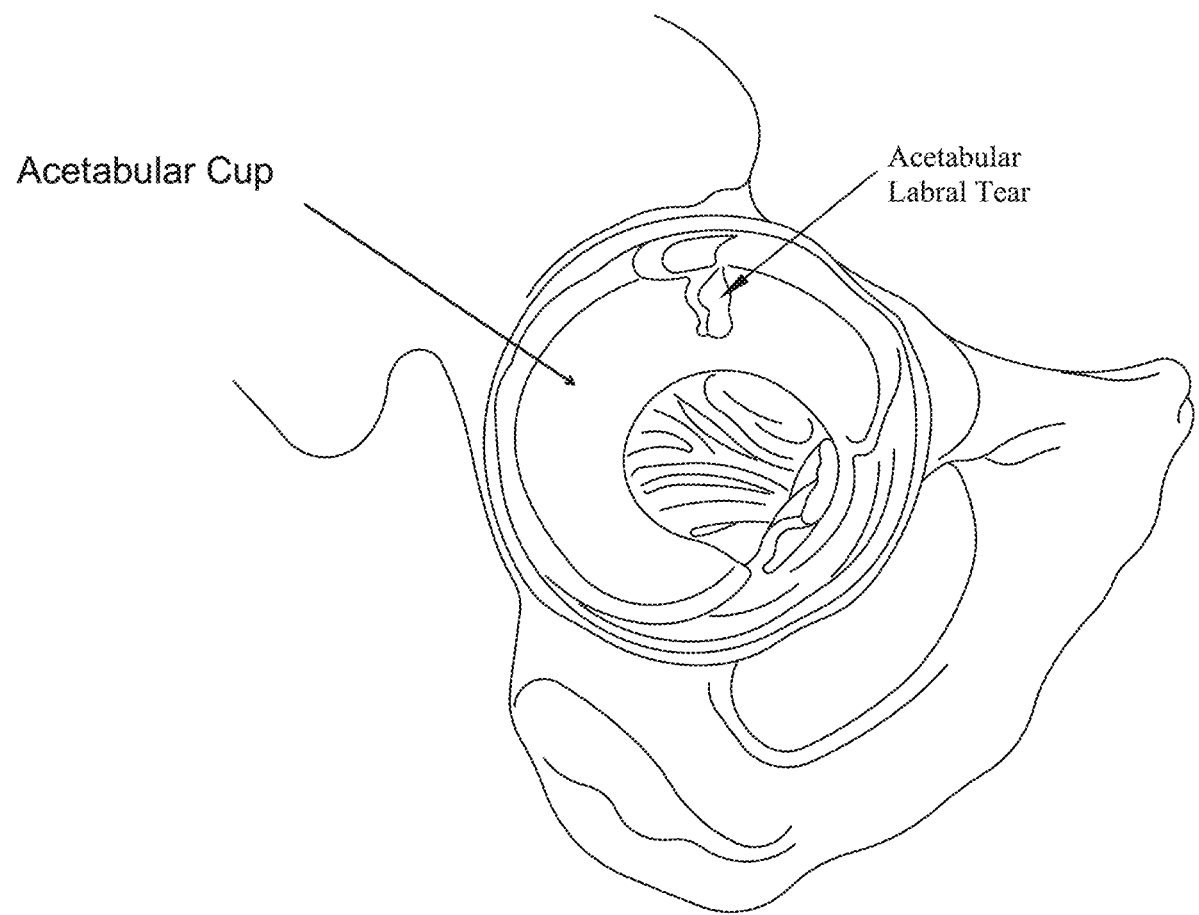
FIG. 15 is a schematic view showing a labral tear.
Figure 16:
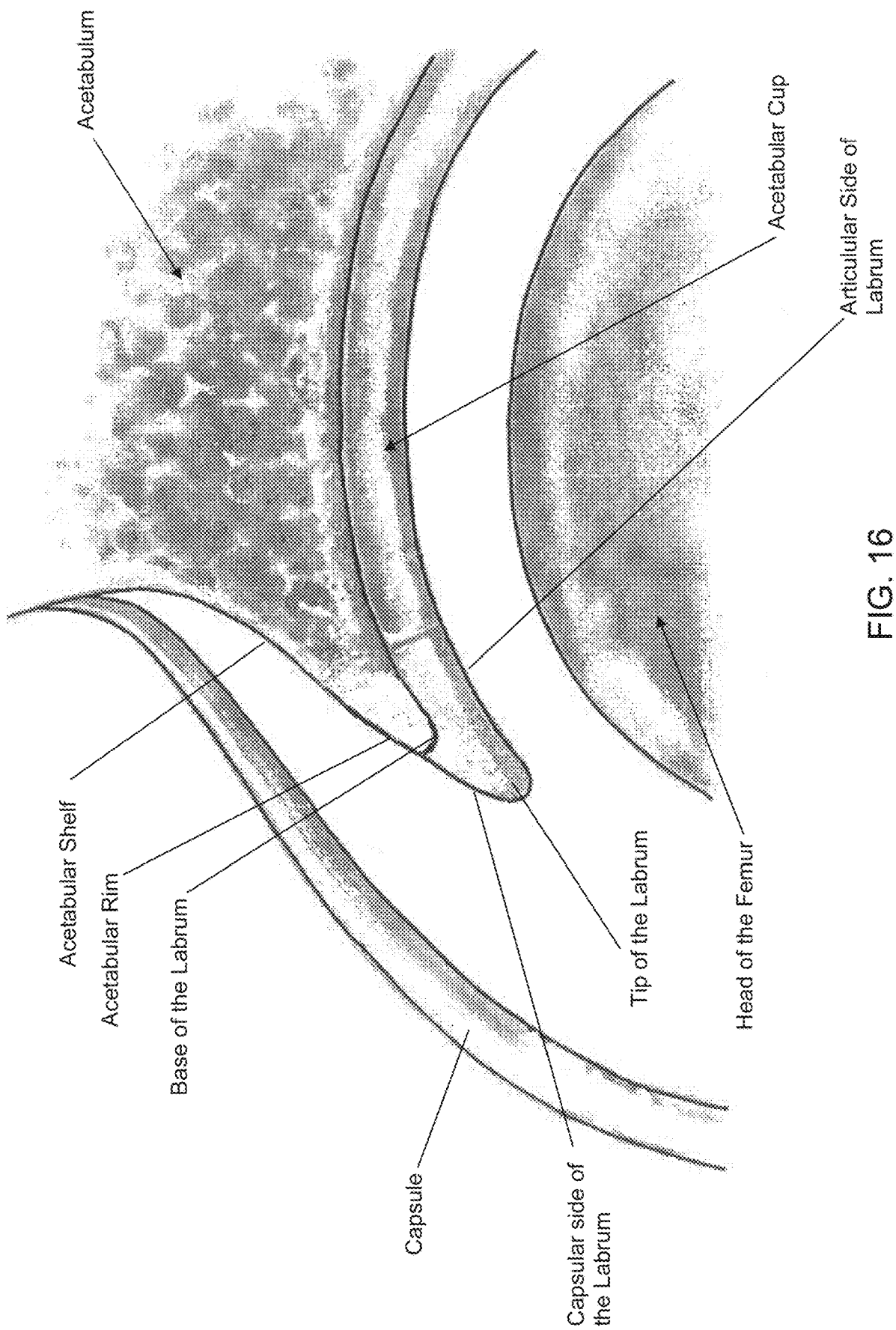
FIG. 16 is a schematic view showing a normal labrum which has its base securely attached to the acetabulum.
Figure 17:
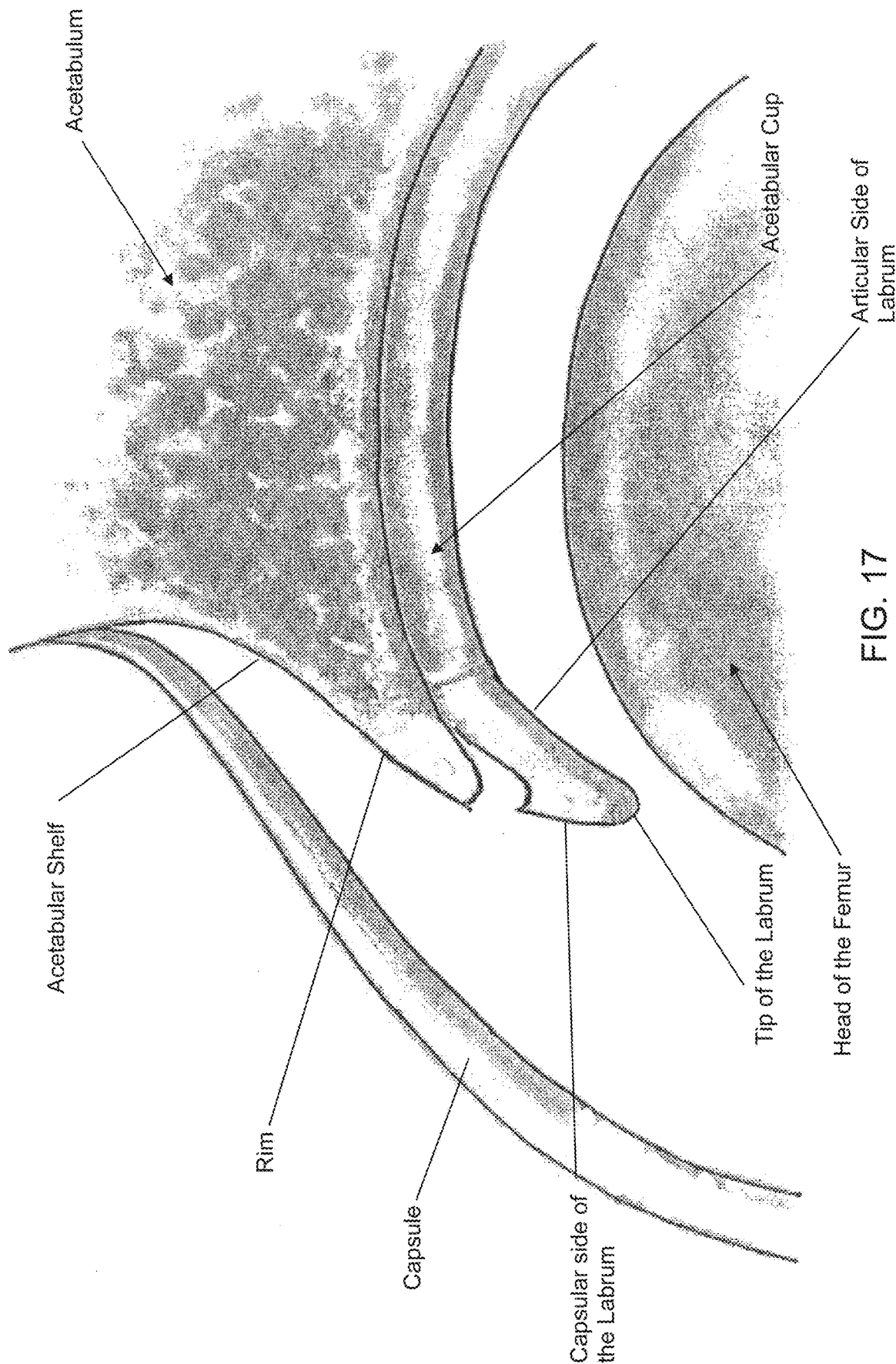
FIG. 17 is a schematic view showing a portion of the labrum detached from the acetabulum.
Figure 18:
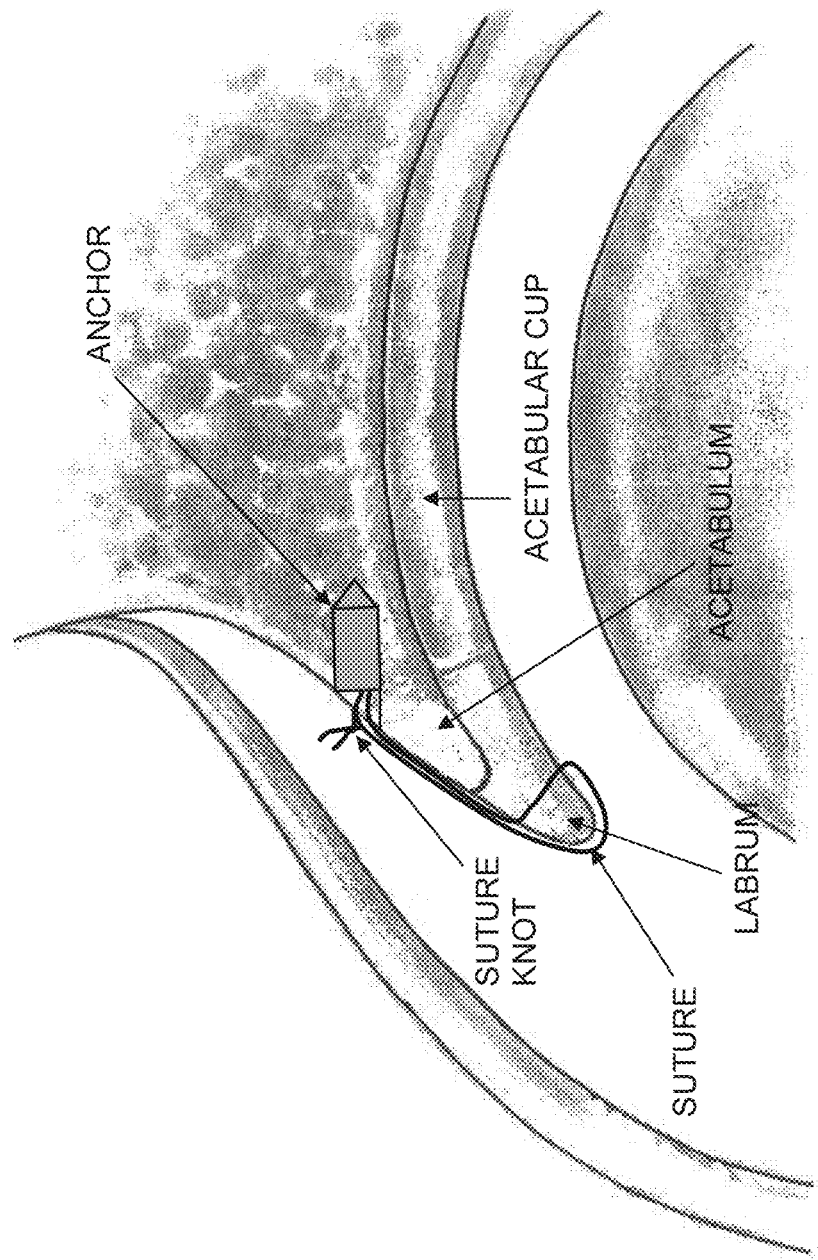
FIG. 18 is a schematic view showing a suture anchor being used to re-attach the labrum to the acetabulum.
Figure 19:
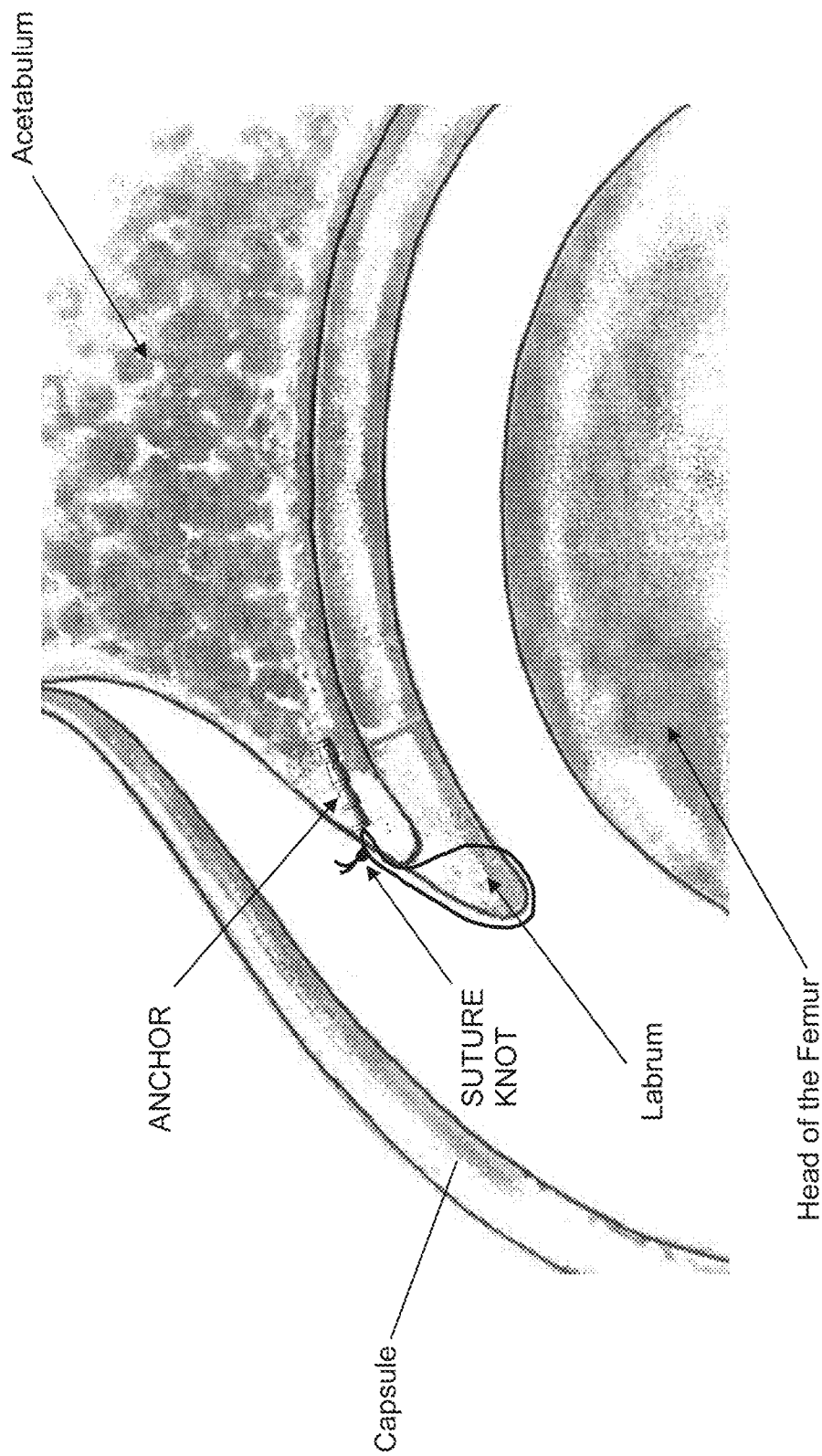
FIG. 19 is a schematic view showing another suture anchor being used to re-attach the labrum to the acetabulum.
Figure 20:
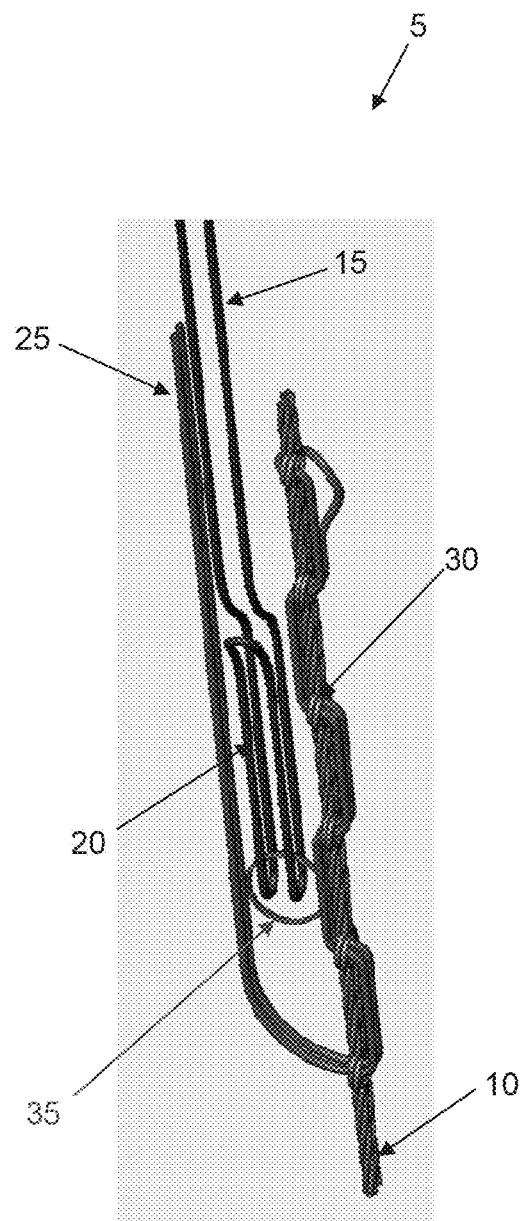

The present invention provides a novel method and apparatus for re-attaching the labrum to the acetabulum.

Among other things, the present invention provides a novel suture anchor system which may be used to re-attach the labrum to the acetabulum, and/or to attach other tissue to bone.

In one preferred form of the present invention, there is provided a suture anchor system wherein a loop of suture is passed through the labrum (or other tissue) and its two free ends are slidably connected (e.g., slidably threaded through) the body of the suture anchor. After the body of the suture anchor is advanced into the acetabulum (or other bone) and the loop of suture is tensioned so as to hold the labrum (or other tissue) in place against the acetabulum (or other bone), the body of the suture anchor is reconfigured so as to lock the body of the suture anchor to the bone and to lock the loop of suture to the body of the suture anchor and hence secure the labrum (or other tissue) to the acetabulum (or other bone). Significantly, the present invention allows the loop of suture to be locked to the body of the suture anchor without requiring a knot to be tied at the surgical site during the procedure.

The present invention also provides a new approach for attaching other tissue to bone, and/or for attaching another object to bone, and/or for attaching an object to tissue other than bone (e.g., cartilage, etc.).

Terminology

Within this document, the following terms are intended to generally have the following meanings:

"Deploy" is intended to mean to change the shape of the body of the suture anchor (the "anchor body") such that the anchor body is secured in a bone hole (whereby to secure the suture anchor to the bone);

"Lock" is intended to mean to affix the loop of suture passed through the labrum (i.e., the "repair suture") to the anchor body;

"Working Suture" is intended to mean the suture(s) used to deploy the anchor body and to lock the repair suture to the anchor body;

"Deployment Strand" is intended to mean the side of the working suture that deploys the anchor body;

"Locking Strand" is intended to mean the side of the working suture that locks the repair suture to the anchor body;

"Repair Suture" is intended to mean the suture passed through the labrum (or other target tissue) and used to affix the target tissue to bone;

"Repair Loop" is intended to mean the portion of the repair suture that passes through the target tissue;

"Decoupled Construction" is intended to mean a design wherein deployment of the anchor body and locking of the repair suture to the anchor body are divided into two separate steps (i.e., where lateral anchor body expansion, and locking the repair suture to the anchor body, occur in two separate steps); and "Coupled Construction" is intended to mean a design wherein deployment of the anchor body and locking of the repair suture to the anchor body occur in the same step (i.e., where lateral anchor body expansion, and locking the repair suture to the anchor body, occur in a single step).

Labral Re-attachment Procedure And Categories Of Designs

To re-attach the labrum to the acetabulum in the hip joint, a single strand of suture (i.e., the repair suture) is first passed through the labrum, and then the two free ends of the repair suture are passed through the anchor body to create a repair loop. The two free ends of the repair suture may be passed through the anchor body in several ways, and the different approaches for doing this can be used to differentiate the various designs of the present invention.

The designs in which the repair suture is passed through a locking knot (e.g., a constrictor knot, a double constrictor knot, a boa knot, etc.) may be categorized as "active suture locking designs" (see, for example, FIGS. 20-32 and 39-47), since the constrictor knot may be actively closed down on the repair suture.

The designs in which the repair suture is bound to the anchor body by friction and/or compression may be categorized as "passive suture locking designs" (see, for example, FIGS. 33-38).

Once the repair suture is passed through the anchor body, the anchor body is inserted into a pre-drilled bone hole using an inserter tool (e.g., an inserter tool I). Then the anchor body is laterally expanded (i.e., deployed in the bone), and the repair suture is locked to the anchor body. The specific manner in which the anchor body is laterally expanded and the repair suture is locked to the anchor body can be accomplished in several ways, and the different approaches can also be used to differentiate the various designs of the present invention.

For designs utilizing a "coupled construction" (see, for example, FIGS. 27-38), the repair suture (and hence the repair loop passing through the target tissue) is tensioned so as to position the target tissue at the desired location, and then the working suture(s) is/are pulled so as to simultaneously deploy the anchor body in the bone hole and lock the repair suture to the anchor body.

For designs utilizing a "decoupled construction" (see, for example, FIGS. 20-26 and 39-47), the deployment strand of the working suture is tensioned first so as to deploy the anchor body in the bone hole, then the repair suture (and hence the repair loop passing through the target tissue) is tensioned so as to position the target tissue at the desired location, and finally the locking strand of the working suture is tensioned so as to lock the repair suture to the anchor body. This latter approach (i.e., the decoupled construction) allows the user to tighten the repair loop so as to position the target tissue at the desired location after the anchor body has been positioned in the bone hole and deployed.

Active Suture Locking Design With Decoupled Construction

FIGS. 20-26 illustrate a suture anchor system 5 which comprises three elements: an anchor body 10 which is longitudinally and laterally deformable, and which is preferably in the form of a braided suture, a repair suture 15 which is connected to the target tissue with a repair loop 20, and a working suture 25 which deploys anchor body 10 and locks repair suture 15 to anchor body 10. Working suture 25 is threaded through loops (or eyelets) 30 in anchor body 10 so as to create an intertwined configuration. A portion of working suture 25 is tied into a knot 35 (e.g., a constrictor knot).

Figure 21:
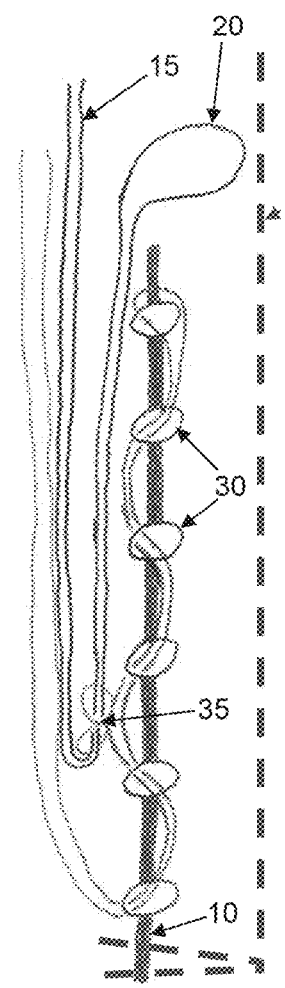

More particularly, and looking now at FIGS. 21 and 24, anchor body 10 is preferably formed out of braided suture and bifurcated so as to create the aforementioned loops 30 which working suture 25 is slidably threaded through. The limb 40 of working suture 25 which is used to create knot 35 (e.g., a constrictor knot) is sometimes referred to herein as the locking strand. The limb 45 of working suture 25 which is used to deploy anchor body 10 (see below) is sometimes referred to herein as the deployment strand. Knot 35 (e.g., a constrictor knot) protrudes from anchor body 10 and is initially in an open, "unlocked" state. Repair suture 15 is passed through the target tissue and then through unlocked knot 35 (e.g., a constrictor knot) prior to anchor body 10 being inserted into the bone hole. Anchor body 10 is then inserted into the bone hole in the state shown in FIGS. 21 and 24 using an inserter (e.g., such as the inserter tool I).

More particularly, and looking now at FIGS. 21 and 24, anchor body 10 is preferably formed out of braided suture and bifurcated so as to create the aforementioned loops 30 which working suture 25 is slidably threaded through. The limb 40 of working suture 25 which is used to create knot 35 (e.g., a constrictor knot) is sometimes referred to herein as the locking strand. The limb 45 of working suture 25 which is used to deploy anchor body 10 (see below) is sometimes referred to herein as the deployment strand. Knot 35 (e.g., a constrictor knot) protrudes from anchor body 10 and is initially in an open, "unlocked" state. Repair suture 15 is passed through the target tissue and then through unlocked knot 35 (e.g., a constrictor knot) prior to anchor body 10 being inserted into the bone hole. Anchor body 10 is then inserted into the bone hole in the state shown in FIGS. 21 and 24 using an inserter (e.g., such as the inserter tool I).

Figure 22:
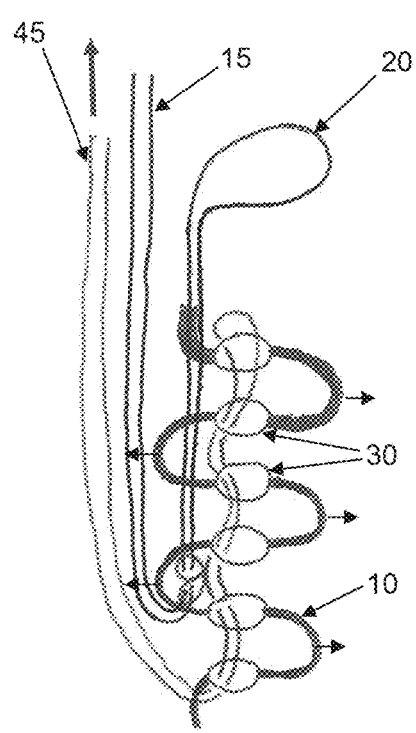

As shown in FIGS. 22 and 25, after anchor body 10 is placed into the bone hole, anchor body 10 is deployed by applying tension to deployment strand 45 of working suture 25. Deployment strand 45 of working suture 25 is distinguished by being the suture limb which first threads through substantially the length of anchor body 10 and then forms knot 35 (e.g., a constrictor knot); locking strand 40 of working suture 25 is distinguished by being the suture limb which first threads through only a portion of the length of anchor body 10 and then forms knot 35 (e.g., a constrictor knot). By applying tension to deployment strand 45 of working suture 25, loops 30 in anchor body 10 are pulled together, which forces the distance between loops 30 to decrease and thereby creates the "S" formation for anchor body 10 shown in FIGS. 22 and 25. This "S" formation for anchor body 10 is wider, in a lateral sense, than the original pre-deployment state for anchor body 10 and engages the side wall of the bone hole so as to secure anchor body 10 in the bone hole. In other words, by applying tension to deployment strand 45 of working suture 25, anchor body 10 is longitudinally shortened and laterally expanded so as to bind anchor body 10 in the bone hole. Note that even after deployment of anchor body 10 in the bone hole, repair suture 15 can still slide within anchor body 10, i.e., within knot 35 (e.g., a constrictor knot) of working suture 25, so that the surgeon can still adjust the tension of repair loop 20, whereby to reposition the target tissue.

Figure 23:
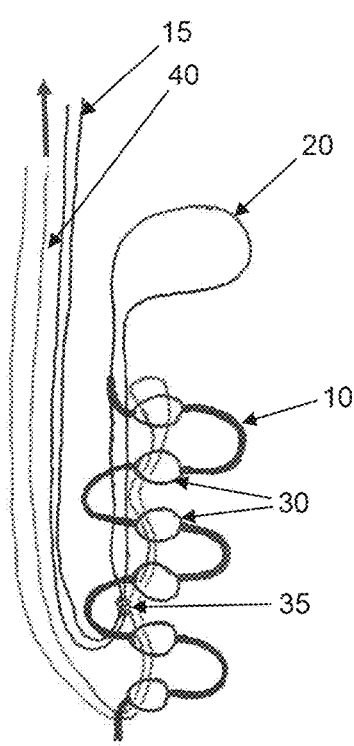

As shown in FIGS. 23 and 26, locking strand 40 of working suture 25 is then pulled so as to tighten knot 35 (e.g., a constrictor knot) around repair suture 15, thereby securing repair loop 20 to anchor body 10. In other words, when locking strand 40 of working suture 25 is pulled tight, knot 35 (e.g., a constrictor knot) goes from an "unlocked" state to a "locked" state. Locked knot 35 (e.g., a constrictor knot) prevents repair suture 15 from moving relative to anchor body 10, and hence locks the target tissue to the bone. The inserter tool (e.g., the inserter tool I) can be removed at this point in the procedure (inserter tool I is not shown in FIGS. 22-26 for clarity).

Although anchor body 10 is shown as a braided suture with bifurcations, it can also be a woven construction. The anchor body 10 may take the form of a rope or tube (in case of a braided structure) or a tape (in the case of a woven structure). If desired, anchor body 10 can comprise bioactive materials so as to give it desired properties, e.g., it can be formed out of bioabsorbable or bioresorbable materials, it can include hydroxyapatite or tricalcium phosphate, etc.

It should be appreciated that knot 35 can be a locking or binding knot of the sort known in the art; for example, knot 35 can be a constrictor knot, a double constrictor knot, a boa knot, etc. If desired, knot 35 (e.g., a constrictor knot) can include a treatment to provide it with a shape-retaining tendency, such that it will tend to retain its unlocked state to facilitate easier threading of the ends of repair suture 15 through anchor body 10. For example, heat or wax can be applied to knot 35 (e.g., a constrictor knot) to increase its rigidity.

It will be appreciated that with the design shown in FIGS. 20-26, suture anchor system 5 uses a so-called decoupled construction since deployment and locking are divided into two separate steps (i.e., lateral anchor body expansion when deployment strand 45 of working suture 25 is tensioned, and locking of repair suture 15 to anchor body 10 when locking strand 45 of working suture 25 is tensioned).

Active Suture Locking Design With Coupled Construction

FIGS. 27-32 show a suture anchor system 5 which also comprises three elements: anchor body 10 which is longitudinally and laterally deformable, and which is preferably in the form of a braided suture tube, repair suture 15 which is connected to the target tissue via repair loop 20, and working suture 25 which deploys anchor body 10 and secures repair suture 15 to anchor body 10. The two proximal ends 50A, 50B of anchor body 10 preferably comprise bone-engagement features 55A, 55B which are hardened and/or shaped in such a way as to enhance bone engagement and thereby resist slippage when a force in the proximal direction is applied to anchor body 10. Working suture 25 may comprise a single strand that is threaded through anchor body 10 twice such that both ends 60A, 60B of working suture 25 terminate in locking, sliding knots 65A, 65B (e.g., Weston knots). The portion of working suture 25 which is disposed outside of anchor body 10 may be a continuous loop 70 extending outside of the body of the patient. Sliding knots 65A, 65B (e.g., Weston knots) are tied in such a way as to allow the suture strand which is passing through the sliding knot to slide in one direction only and prevent (i.e., lock) the suture from sliding in the other direction. The purpose of sliding knots 65A, 65B is to assist in compressing and expanding anchor body 10. Working suture 25 comprises a knot 35 (e.g., a constrictor knot) near the middle of anchor body 10. Knot 35 (e.g., a constrictor knot) protrudes from anchor body 10 through a window 75 located at the distal end of anchor body 10 and is initially in an open, "unlocked" state, with repair suture 15 extending through knot 35 (e.g., a constrictor knot) of working suture 25. Anchor body 10 is inserted into the bone hole in the state shown in FIG. 27 using an inserter (e.g., the inserter tool I, shown in FIG. 27 but not shown in FIG. 28 for clarity).

Figure 27:
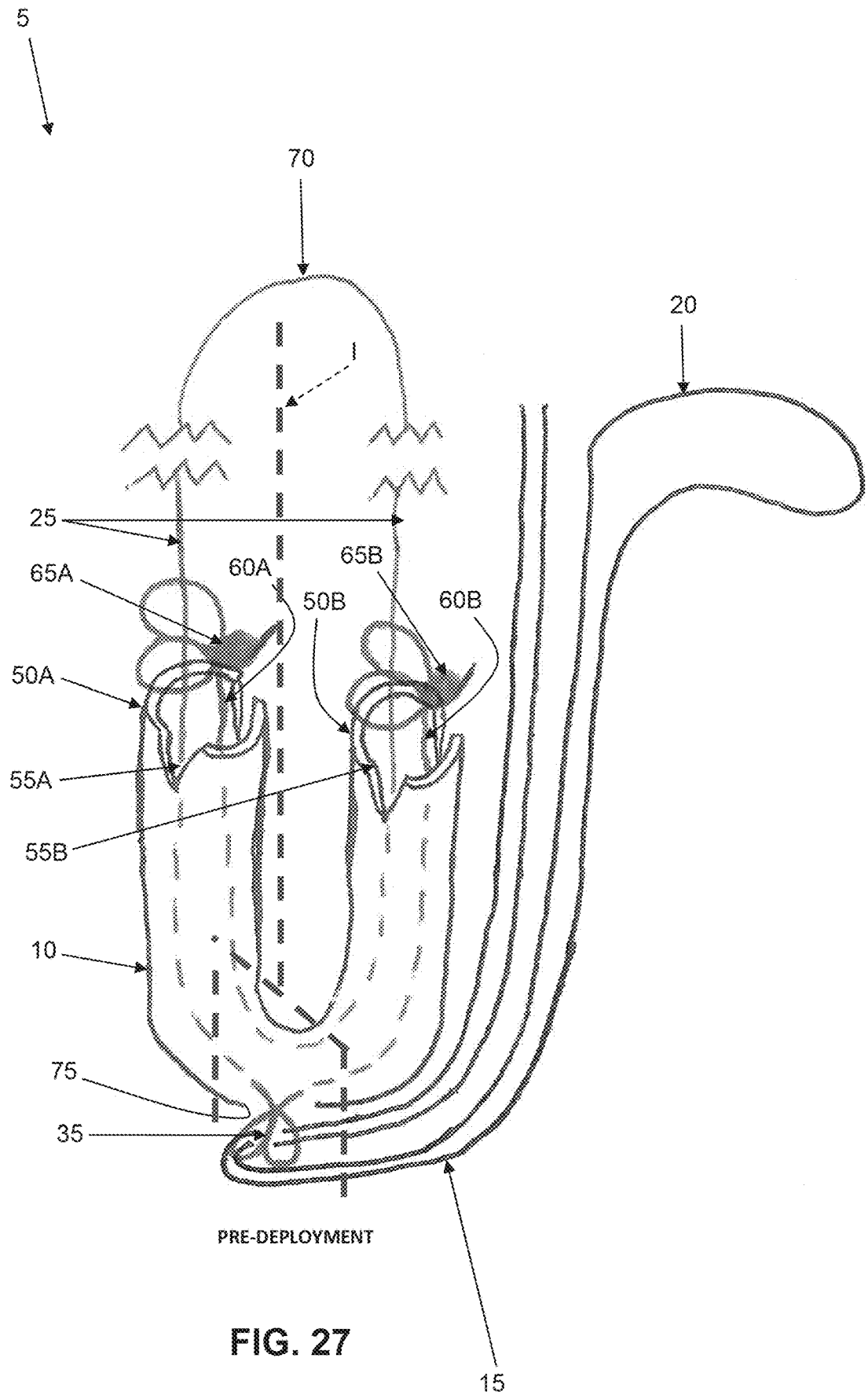
FIGS. 27 and 28 show another preferred suture anchor system formed in accordance with the present invention.
Figure 28:
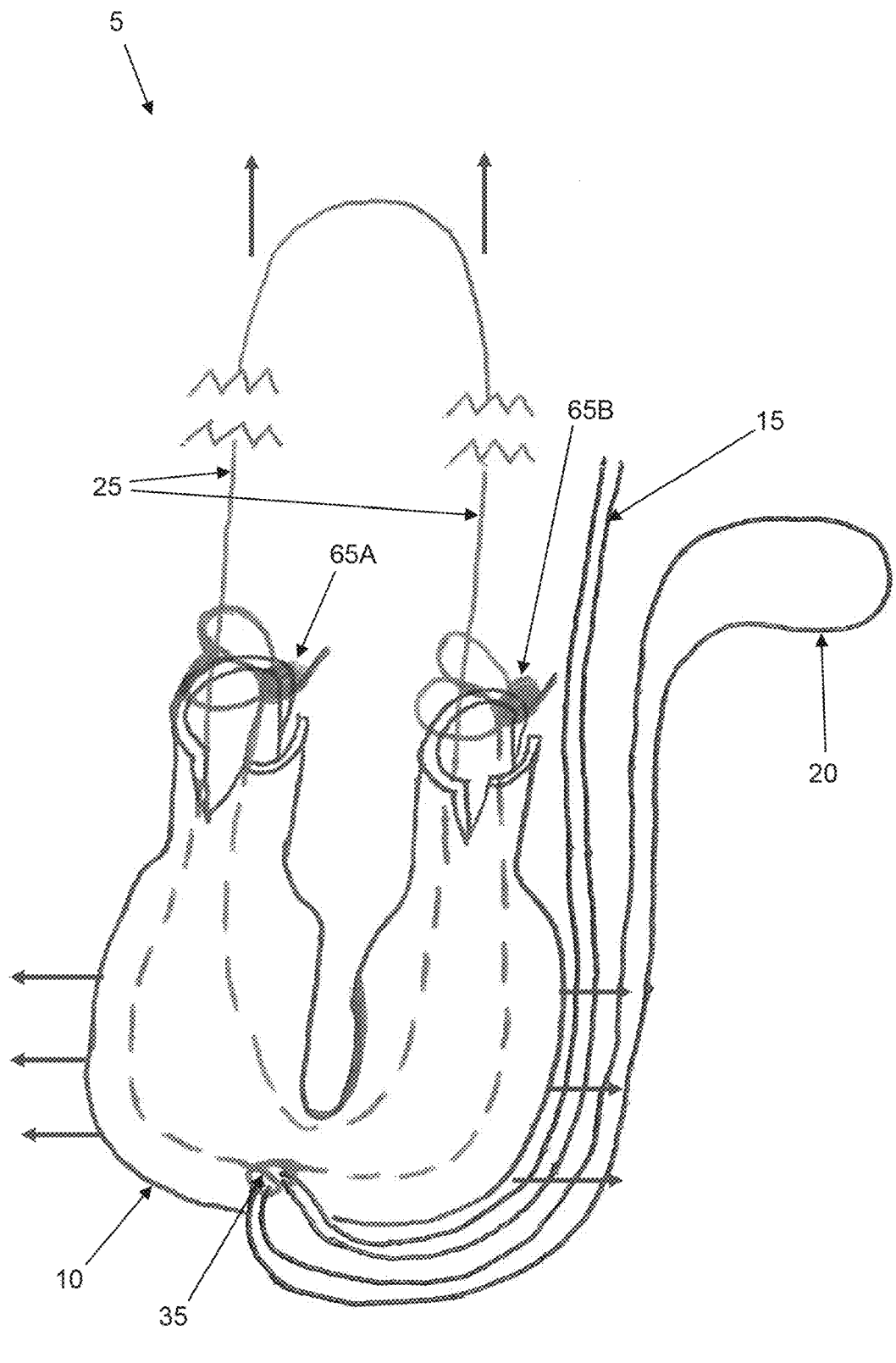

FIG. 28 shows the suture anchor system 5 of FIG. 27 in a deployed and locked state. After repair loop 20 is appropriately tensioned, anchor body 10 is deployed (i.e., laterally expanded) in the bone hole and locked by applying a proximal force to loop 70 of working suture 25. More particularly, the bone-engagement features 55A, 55B of the two proximal ends 50A, 50B of anchor body 10 interact with the side wall of the bone hole and prevent anchor body 10 from moving proximally out of the bone hole. Thereafter applying a proximal force to loop 70 of working suture 25 causes two actions to occur:

(i) knot 35 (e.g., a constrictor knot) of working suture 25 goes from an "unlocked" state to a "locked" state, tightening around repair suture 15 and thereby securing repair suture 15 to anchor body 10; and (ii) locking, sliding knots 65A, 65B (e.g., the Weston knots) in working suture 25 slide along the limbs of working suture 25, causing anchor body 10 to longitudinally compress and laterally expand—the lateral expansion of anchor body 10 provides additional securement of anchor body 10 in the bone hole, and the locking nature of sliding knots 65A, 65B (e.g., the Weston knots) prevents them from sliding in the opposite direction along working suture 25 once locked, thereby preventing anchor body 10 from reverting to its initial unexpanded state.

Figure 29:
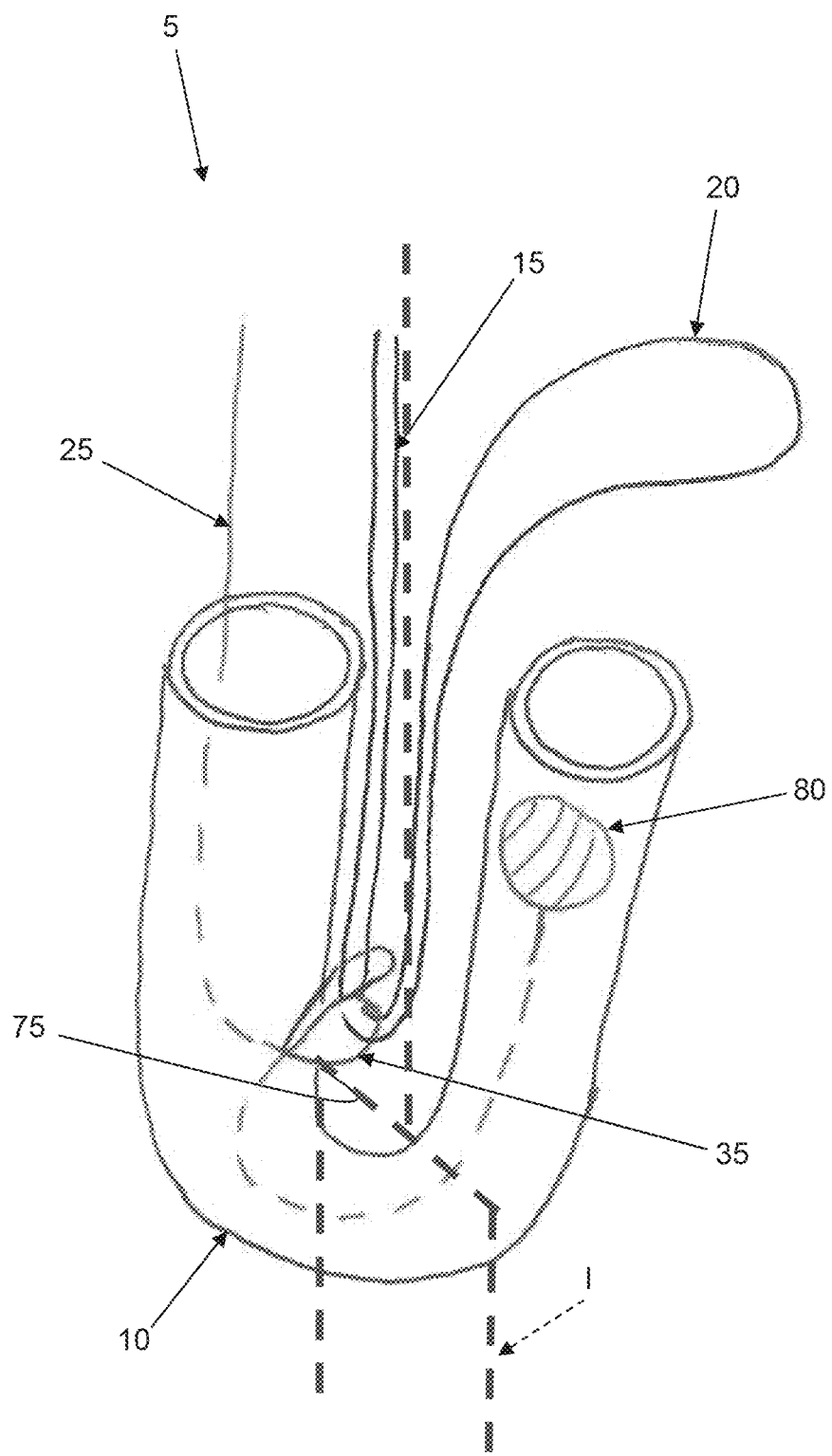
FIGS. 29 and 30 show another preferred suture anchor system formed in accordance with the present invention.
Figure 30:
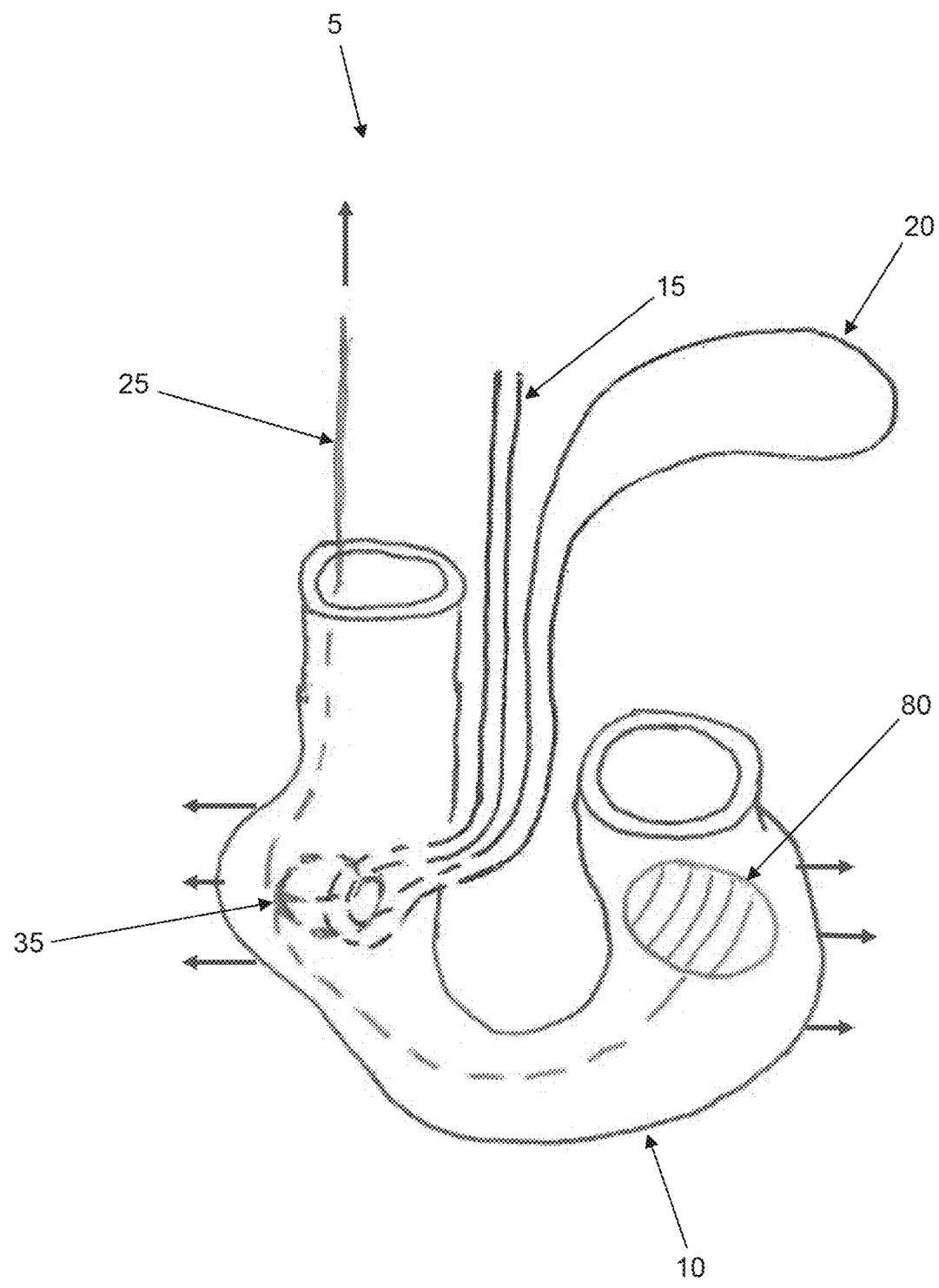

FIGS. 29 and 30 show another suture anchor system 5 which also utilizes three elements, i.e., anchor body 10 which is longitudinally and laterally deformable, and which is preferably in the form of a braided suture tube, repair suture 15 which is connected to the target tissue via repair loop 20, and working suture 25 which deploys anchor body 10 and secures repair loop 20 to anchor body 10. As seen in FIG. 29, working suture 25 is threaded through anchor body 10 once and terminates in a bulky stopper knot 80 (e.g., an Ashley-Stopper knot). Knot 35 (e.g., a constrictor knot) is tied along the portion of working suture 25 that passes through anchor body 10. Knot 35 (e.g., a constrictor knot) protrudes from anchor body 10 through window 75 located in anchor body 10, and is initially in an open, "unlocked" state. Anchor body 10 is inserted into the bone hole using an inserter (e.g., such as the inserter tool I, shown in FIG. 29 but not shown in FIG. 30 for clarity) with knot 35 (e.g., a constrictor knot) of working suture 25 and stopper knot 80 of working suture 25 being longitudinally spaced from one another in the manner shown in FIG. 29.

FIG. 30 shows the suture anchor system of FIG. 29 in a deployed and locked state. After anchor body 10 is placed into a bone hole, and repair suture 15 is tensioned to the desired position (i.e., by pulling on the free ends of repair suture 15), anchor body 10 is deployed (i.e., expanded laterally to engage the side wall of the bone hole) and locked (i.e., repair loop 20 is locked to anchor body 10) by applying a proximal force to working suture 25. More particularly, bone-engagement features 55A, 55B of anchor body 10 interact with the side wall of the bone hole and prevent anchor body 10 from moving proximally out of the bone hole. Thereafter applying a proximal force to working suture 25 causes two actions to occur:

(i) knot 35 (e.g., a constrictor knot) of working suture 25 goes from an "unlocked" state to a "locked" state, tightening around repair suture 15, and thereby securing repair suture 15 to anchor body 10; and (ii) knot 35 (e.g., a constrictor knot) of working suture 25 moves proximally due to the deployment force, but is impeded by engagement of stopper knot 80 of working suture 25 with the surrounding anchor body 10. This action causes anchor body 10 to expand laterally, thereby securing the suture anchor 5 to the bone.

Figure 31:
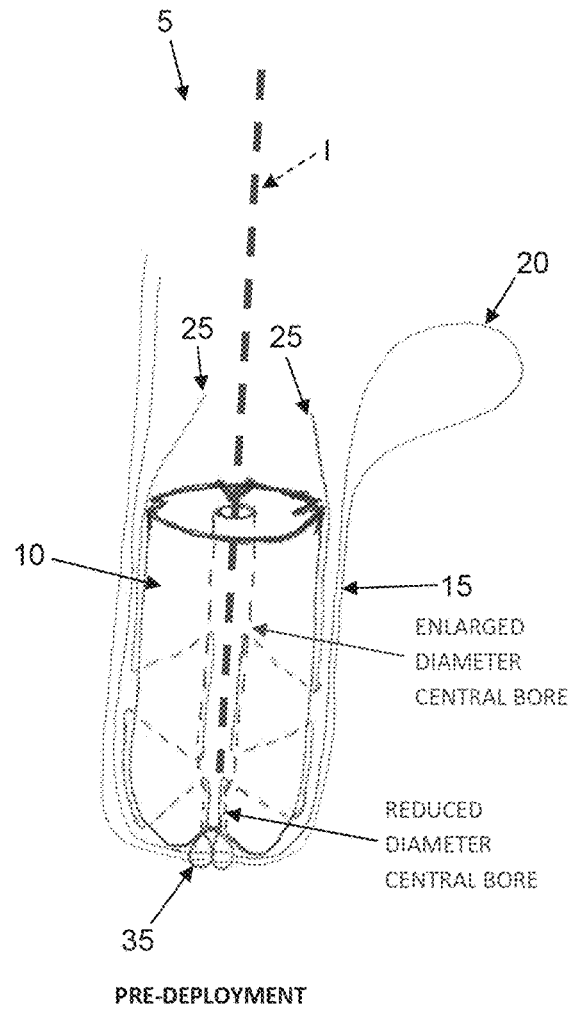
FIGS. 31 and 32 show another preferred suture anchor system formed in accordance with the present invention.
Figure 32:
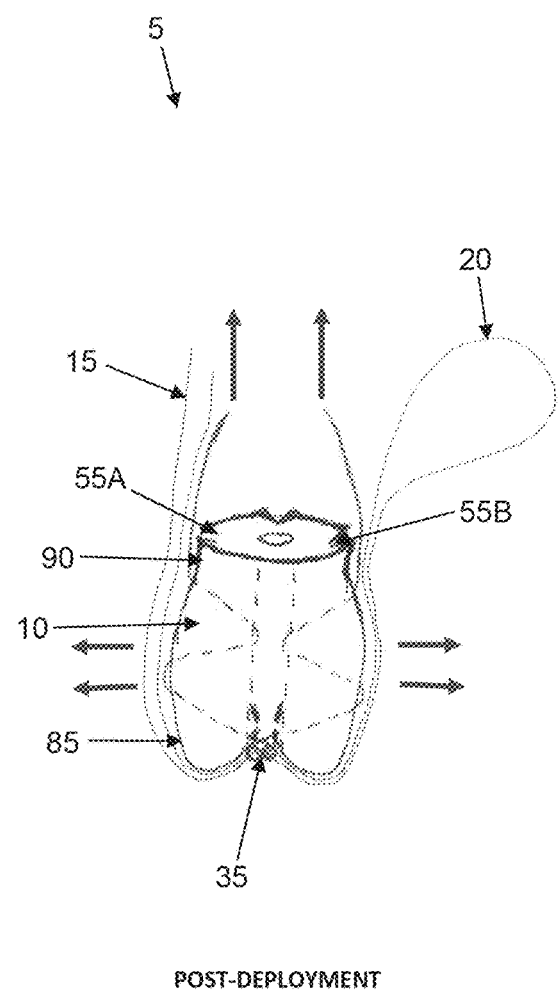

FIGS. 31 and 32 show another suture anchor system 5 which also utilizes three elements, i.e., anchor body 10 which is longitudinally and laterally deformable, and which is preferably in the form of a braided suture tube, repair suture 15 which is connected to the target tissue via repair loop 20, and working suture 25 which deploys anchor body 10 and secures repair suture 15 to anchor body 10. Again, a knot 35 (e.g., a constrictor knot) in working suture 25 actively deploys (i.e., laterally expands) anchor body 10 and locks repair suture 15 to anchor body 10. However, as seen in FIG. 31, in this form of the invention, anchor body 10 is not folded so as to become U-shaped upon insertion into the bone hole, but instead remains substantially straight within the bone hole (and is axially compressed so as to be laterally expanded, as will hereinafter be discussed in further detail). Additionally, the distal portion 85 of anchor body 10 has a reduced diameter which allows anchor body 10 to be inserted into a bone hole with an inserter tool (e.g., such as the inserter tool I, shown in FIG. 31 but not shown in FIG. 32 for clarity) positioned within the inner diameter of anchor body 10. Working suture 25 is threaded or woven through the walls of anchor body 10, and knot 35 (e.g., a constrictor knot) is tied in working suture 25 at the distal tip of anchor body 10. In the pre-deployed state, repair suture 15 is able to slide through knot 35 (e.g., a constrictor knot) in working suture 25 inasmuch as knot 35 (e.g., a constrictor knot) is initially in an open, "unlocked" state.

FIG. 32 shows the suture anchor system of FIG. 31 in a deployed (i.e., laterally expanded) and locked (i.e., repair suture 15 is locked to anchor body 10) state. Anchor body 10 is expanded and locked by applying a proximal force to working suture 25. More particularly, bone-engagement features 55A, 55B of suture anchor 10 interact with the side wall of the bone hole and prevent anchor body 10 from moving proximally out of the bone hole during the initial anchor body insertion. Thereafter applying a proximal force to working suture 25 causes two actions to occur:

(i) the interwoven working suture 25 causes anchor body 10 to longitudinally compress and laterally expand—this lateral expansion secures anchor body 10 in the bone hole; and (ii) knot 35 (e.g., a constrictor knot) in working suture 25 is tightened around repair suture 15, such that knot 35 (e.g., a constrictor knot) goes from an "unlocked" state to a "locked" state, thereby securing repair suture 15 to anchor body 10.

If desired, the anchor body 10 of the suture anchor system 5 of FIGS. 31 and 32 can be constructed so as to have different properties along its length. By way of example but not limitation, the proximal section 90 of anchor body 10 may be a tight, high density braid that does not change size/shape as anchor body 10 is deployed, and the distal section 85 of anchor body 10 can be designed to compress and expand. This construction has the effect of causing distal section 85 of anchor body 10 to expand laterally while proximal section 90 of suture anchor 5 remains substantially constant in diameter. The inserter tool I is then removed.

Passive Suture Locking Design With Coupled Construction

Figure 33:
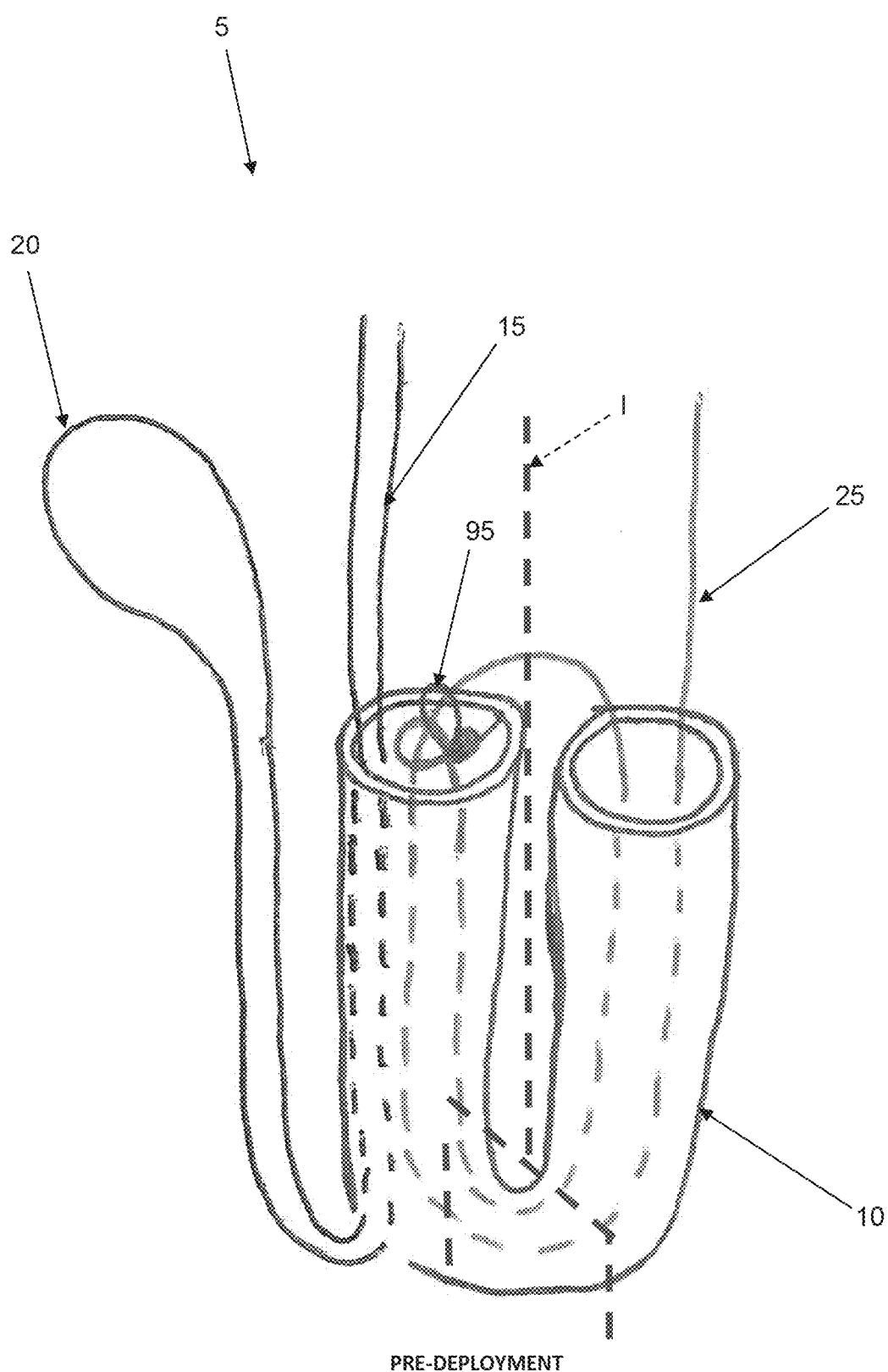
FIGS. 33 and 34 show another preferred suture anchor system formed in accordance with the present invention.
Figure 34:
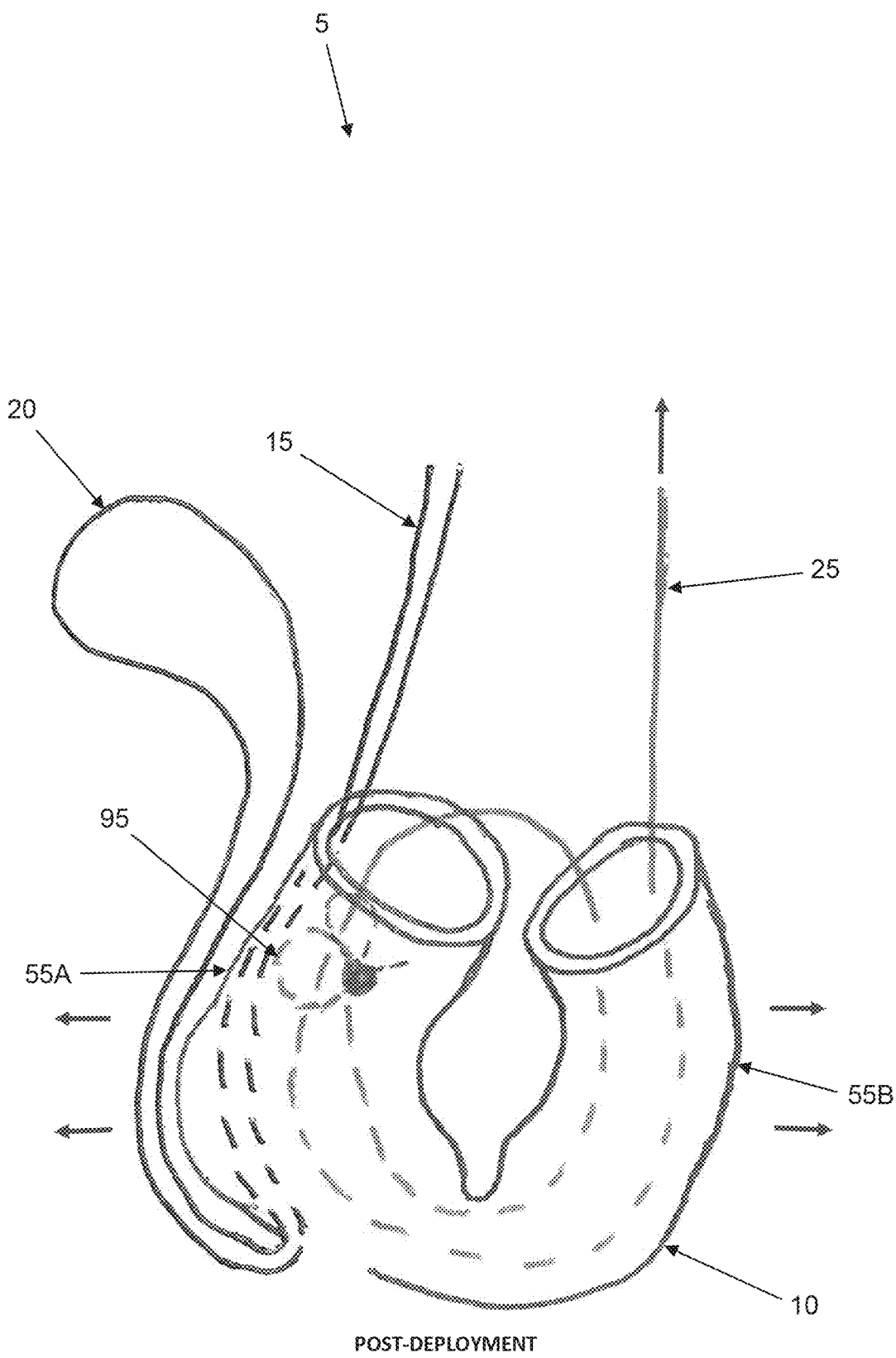

FIGS. 33 and 34 show another suture anchor system 5 which also utilizes three elements, i.e., anchor body 10 which is longitudinally and laterally deformable, and which is preferably in the form of a braided suture tube, repair suture 15 which is connected to the target tissue via repair loop 20, and working suture 25 which deploys anchor body 10 and secures repair suture 15 to anchor body 10. However, in this form of the invention, both limbs of repair suture 15 are loaded through the side of anchor body 10, and working suture 25 has a one-way locking, sliding knot 95 (e.g., a Weston knot) instead of a knot 35 (e.g., a constrictor knot or double constrictor knot or boa knot, etc.). In the pre-deployed state (FIG. 33), repair suture 15 is able to slide through anchor body 10. Working suture 25 passes through anchor body 10 twice and terminates at one end with the one-way locking, sliding knot 95, while the other end of the working suture 25 extends proximally outside anchor body 10 and serves as both the locking strand and deployment strand of working suture 25. Anchor body 10 is inserted into the bone hole in the state shown in FIG. 33 using an inserter (e.g., such as the inserter tool I, shown in FIG. 33 but not shown in FIG. 34 for clarity).

FIG. 34 shows the suture anchor system 5 of FIG. 33 in a deployed (i.e., laterally expanded) and locked (i.e., repair suture 15 is locked to anchor body 10) state. Anchor body 10 is expanded and locked by applying a proximal force to deployment strand 45 of working suture 25. More particularly, bone-engagement features 55A, 55B of anchor body 10 interact with the side wall of the bone hole and prevent suture anchor 5 from moving proximally out of the bone hole during initial anchor body insertion. Thereafter applying a proximal force to deployment strand 45 of working suture 25 causes two actions to occur:

(i) the one-way, locking sliding knot 95 of working suture 25 slides along the limb of working suture 25, causing anchor body 10 to longitudinally compress and laterally expand—the lateral expansion of anchor body 10 secures anchor body 10 in the bone hole, and the locking nature of one-way locking, sliding knot 95 of working suture 25 prevents working suture 25 from sliding in the opposite direction once locked, thus preventing anchor body 10 from reverting to its initial unexpanded state; and (ii) the lateral expansion of anchor body 10 compresses repair suture 15 against the side wall of the bone hole—the friction between repair suture 15, one-way locking, sliding knot 95 in working suture 25 and anchor body 10 secures the repair suture 15 to anchor body 10.

Figure 35:
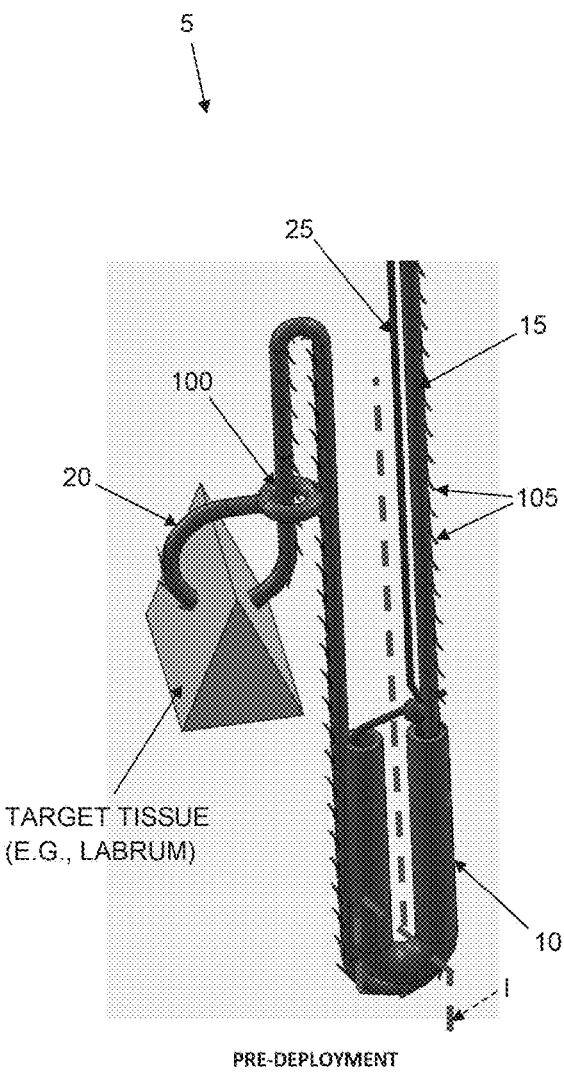
FIGS. 35 and 36 show another preferred suture anchor system formed in accordance with the present invention.
Figure 36:
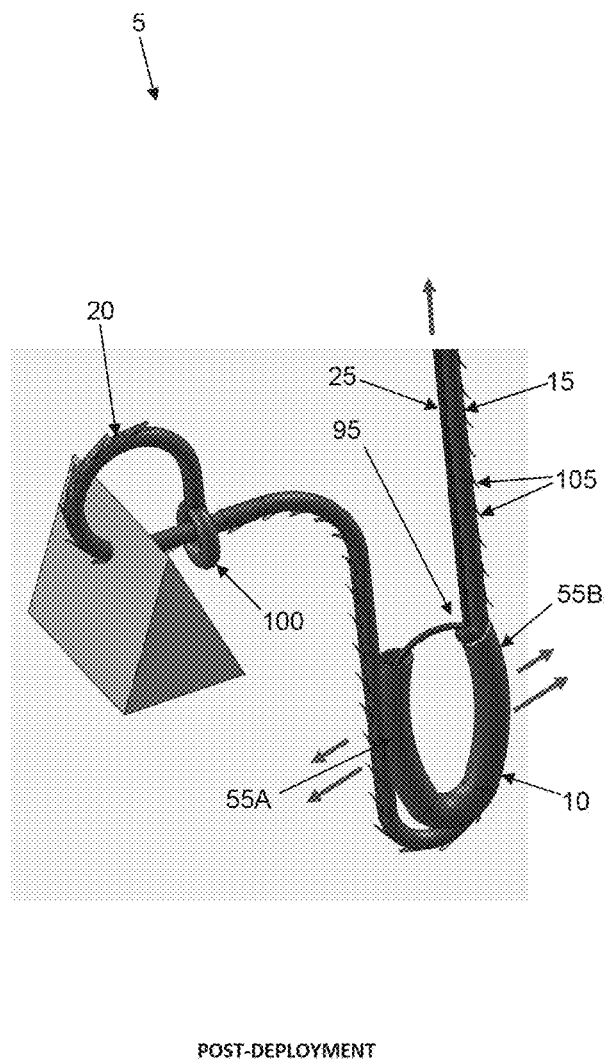

FIGS. 35 and 36 show another suture anchor system 5 which also utilizes three elements, i.e., anchor body 10 which is longitudinally and laterally deformable, and which is preferably in the form of a braided suture tube, repair suture 15 which is connected to the target tissue via repair loop 20, and working suture 25 which deploys anchor body 10 and secures repair suture 15 to anchor body 10. Anchor body 10 is inserted into the bone hole in the state shown in FIG. 35 using an inserter (such as the inserter I shown in FIG. 35 but not shown in FIG. 36 for clarity). However, in this form of the present invention, repair suture 15 is a barbed suture having an eyelet 100 disposed at one end of repair suture 15. Eyelet 100 is used to create the repair loop 20 through the target tissue and barbs 105 allow the repair suture 15 to be tensioned and held in place. In this design, only a single strand of barbed repair suture 15 passes through anchor body 10. Alternatively a bi-directional barbed repair suture in which the barb direction is reversed along one half of the length relative to the other (not shown) may be used. In embodiments that utilize the bi-directional barbed suture, repair loop 20 is formed by the segment of the suture where the barbs change direction, and both ends of the bi-directional barbed suture (not shown) pass through anchor body 10. Working suture 25 includes a one-way locking, sliding knot 95.

FIG. 36 shows the suture anchor system 5 of FIG. 35 in the deployed (i.e., laterally expanded) and locked (i.e., repair suture 15 is locked to anchor body 10) state. The barbed repair suture 15 is constructed in such a way that it can slide through anchor body 10 in one direction, but not in the other direction. This characteristic causes repair suture 15 to be held in position even before anchor body 10 is deployed (i.e., laterally expanded) in the bone hole. Anchor body 10 is deployed (i.e., laterally expanded) in the bone hole by applying a proximal force to working suture 25. More particularly bone-engagement features 55A, 55B of anchor body 10 interact with the side wall of the bone hole and prevent suture anchor 5 from moving proximally out of the bone hole during the initial insertion of anchor body 10 into the bone hole. Thereafter applying a proximal force to working suture 25 causes two actions to occur:

(i) one-way locking, sliding knot 95 formed in working suture 25 slides along the limb of working suture 25, causing anchor body 10 to longitudinally compress and laterally expand—this lateral expansion secures anchor body 10 in the bone hole, and the locking nature of one-way locking, sliding knot 95 in working suture 25 prevents working suture 25 from sliding in the opposite direction once locked, thus preventing anchor body 10 from reverting to its initial, unexpanded state; and (ii) the expansion of anchor body 10 compresses repair suture 15 against the side wall of the bone hole, barbs 105 engage with anchor body 10 and secure repair suture 15 to anchor body 10.

FIGS. 37 and 38 show another suture anchor system 5 which also utilizes three elements, i.e., anchor body 10 which is longitudinally and laterally deformable, and which is preferably in the form of a braided suture tube, repair suture 15 which is connected to the target tissue via repair loop 20, and working suture 25 which deploys anchor body 10 and secures repair suture 15 to anchor body 10. Each end of working suture 25 is passed through one end of anchor body 10. A stopper knot 80 is tied at the end of each limb of working suture 25 so that both stopper knots 80 are disposed within anchor body 10. As shown in FIG. 37, stopper knots 80 are initially disposed distal of repair loop 20 and are preferably longitudinally staggered so that anchor body 10 can have a minimal diameter profile.

Both limbs of repair suture 15 are loaded through one end of anchor body 10, passed through internal windows 75 in anchor body 10, and exit through the other end of anchor body 10. In the pre-deployed state (FIG. 37), repair suture 15 is able to slide through anchor body 10 of suture anchor 5. Anchor body 10 is inserted into the bone hole in the state shown in FIG. 37 using an inserter (such as the inserter I shown in FIG. 37 but not shown in FIG. 38 for clarity).

FIG. 38 shows the suture anchor system 5 of FIG. 37 in a deployed (i.e., laterally expanded) and locked (i.e., repair suture 15 is locked to anchor body 10) state. Suture anchor 5 is expanded and locked by applying a proximal force to working suture 25. More particularly, bone-engagement features 55A, 55B of anchor body 10 interact with the wall of the bone hole and prevent anchor body 10 from moving proximally out of the bone hole during initial insertion of anchor body 10 into the bone hole. Thereafter applying a proximal force to working suture 25 causes two actions to occur:

(i) stopper knots 80 of working suture 25 move proximally, and from a staggered configuration to a parallel or non-staggered configuration—as this occurs, the reduced diameter of the proximal ends of anchor body 10 keeps stopper knots 80 of working suture 25 from pulling all of the way out of anchor body 10, thereby causing anchor body 10 to longitudinally compress and laterally expand as stopper knots 80 wedge themselves together in the bone hole and secure anchor body 10 in the bone hole; and (ii) the wedging effect of stopper knots 80 of working suture 25 compress repair suture 15—the friction caused by this compression secures repair suture 15 to anchor body 10.

Additional Constructions

Figure 39:
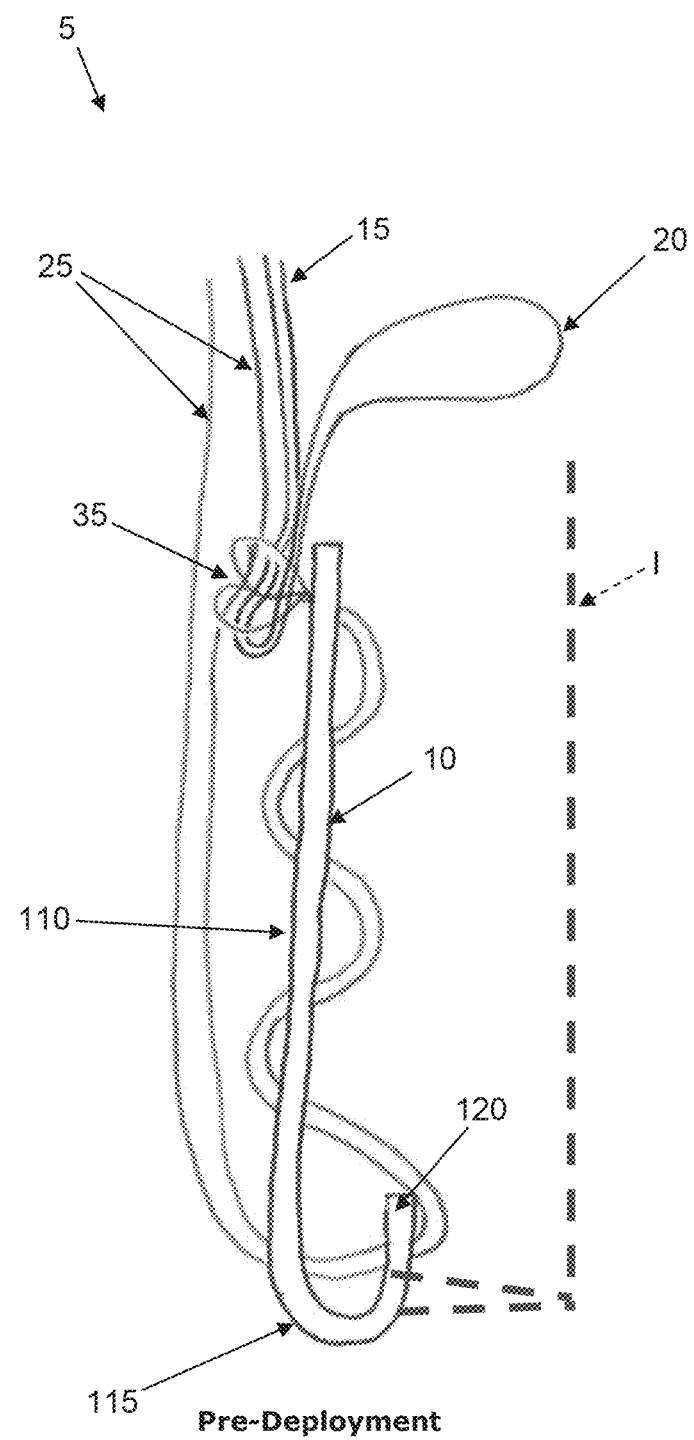
FIGS. 39-41 show another preferred suture anchor system formed in accordance with the present invention.
Figure 40:
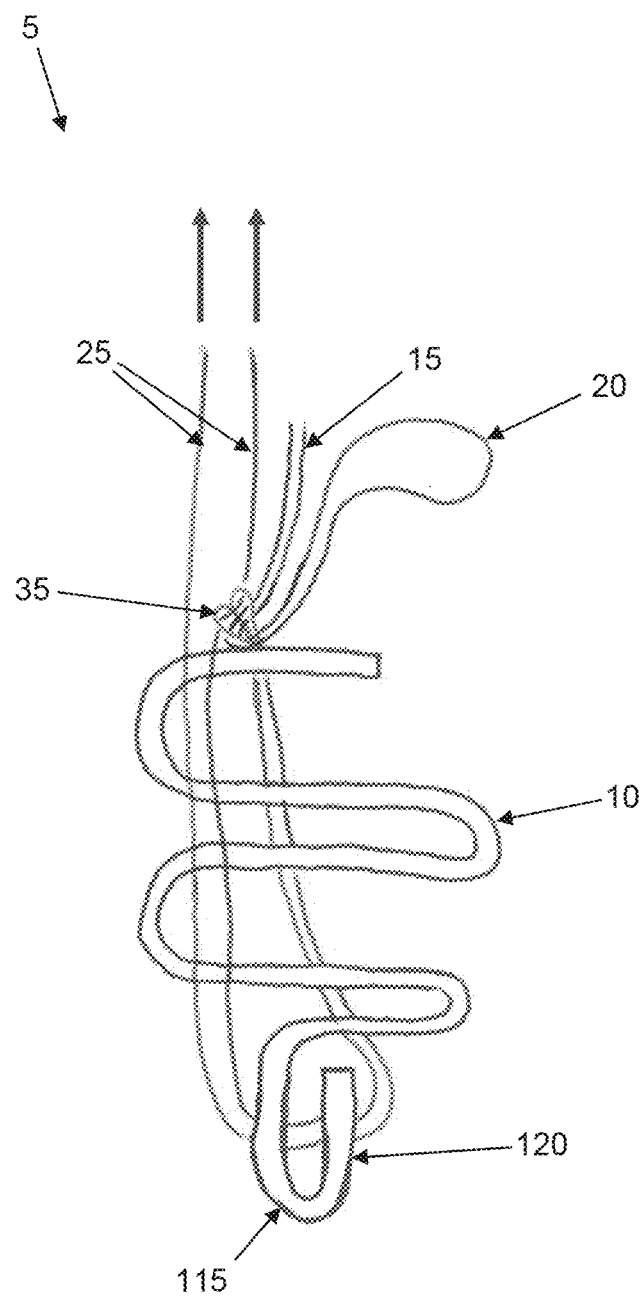
Figure 41:
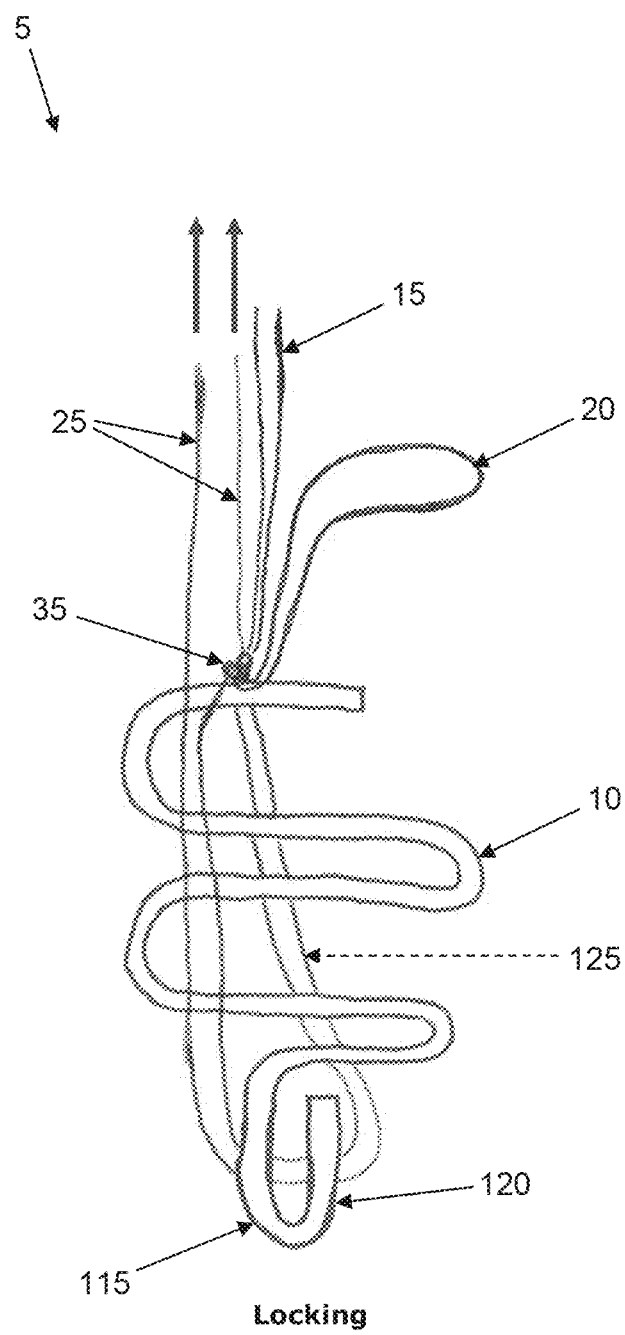

Looking next at FIGS. 39-41, there is shown another suture anchor system 5 which also utilizes three elements, i.e., anchor body 10 which is longitudinally and laterally deformable, and which is preferably in the form of a braided suture, repair suture 15 having repair loop 20, and working suture 25. In this form of the invention, anchor body 10 preferably comprises a woven tape (e.g., a relatively flat, elongated structure) that is made of woven fibers; alternatively, anchor body 10 can comprise a braided structure. In this form of the invention, anchor body 10 is also preferably formed in a "J" configuration, generally comprising a primary section 110, an arc 115 and a return section 120. Working suture 25 preferably passes alongside primary section 110 in the distal direction, then passes through primary section 110 near arc 115, then passes through return section 120, and then weaves in and out of primary section 110 in a proximal direction. After a final pass through primary section 110 near the proximal end of anchor body 10, working suture 25 forms a knot 35 (e.g., a constrictor knot). Both strands of repair suture 15, as well as one strand of working suture 25, pass through knot 35 (e.g., a constrictor knot). In this form of the invention, knot 35 (e.g., a constrictor knot) locks repair loop 20 to anchor body 10, as well as locks anchor body 10 in a collapsed state (i.e., in a laterally-expanded state).

Suture anchor 5 may be deployed in the following manner:

1. Repair suture 15 is passed through the target tissue which is to be attached to the bone, and then repair suture 15 is loaded (e.g., threaded) onto anchor body 10, i.e., by passing the two strands of repair suture 20 through knot 35 (e.g., a constrictor knot) of working suture 25.

2. Anchor body 10 is inserted into the bone hole with an inserter (e.g., such as the inserter tool I, shown in FIG. 39 but not shown in FIGS. 40 and 41 for clarity). The tip of the inserter preferably engages the inner surface of arc 115 of anchor body 10 so that a pushing action pushes anchor body 10 into the bone hole. See FIG. 39.

3. Tension is pulled on one or both strands of working suture 25 so as to at least partially deploy anchor body 10 within the bone hole. More particularly, pulling on one or both strands of working suture 25 causes anchor body 10 to be pulled into a folded shape which contracts longitudinally and expands laterally so as to engage the side walls of the bone hole. See FIG. 40.

4. The surgeon can now adjust the tension on the free ends of repair suture 15, whereby to pull the soft tissue into a desired position against the bone.

5. One or both strands of working suture 25 are then further tensioned so as to tighten knot 35 (e.g., a constrictor knot) and hence lock both strands of repair suture 20 to anchor body 10, as well to lock one strand of working suture 25, whereby to ensure that anchor body 10 remains in a collapsed state (i.e., laterally-expanded and engaging the bone). See FIG. 41. Note that only one strand of working suture 25 needs to be locked in order to hold anchor body 10 in a collapsed (i.e., laterally-expanded) state and keep knot 35 coupled to anchor body 10, because that strand of working suture 25 creates a locked loop 125 that holds anchor body 10 in its collapsed state.

6. The inserter (e.g., such as the inserter tool I) is then disengaged from anchor body 10 and removed from the implant location.

In an alternative embodiment, the surgeon can adjust the tension of repair suture 20 between Steps 2 and 3 (rather than at Step 4 as discussed above).

This form of the invention may include variations of the foregoing anchor construction. By way of example but not limitation, the strands of working suture 25 may be passed through anchor body 10 at more (or fewer) locations, and/or at different locations, than as shown in FIGS. 39-41. In addition, anchor body 10 may not collapse into the folded condition as shown in FIGS. 40 and 41, but may collapse into a different shape (but still expand laterally so as to create adequate anchor pull-out strength in the bone hole).

Figure 42:
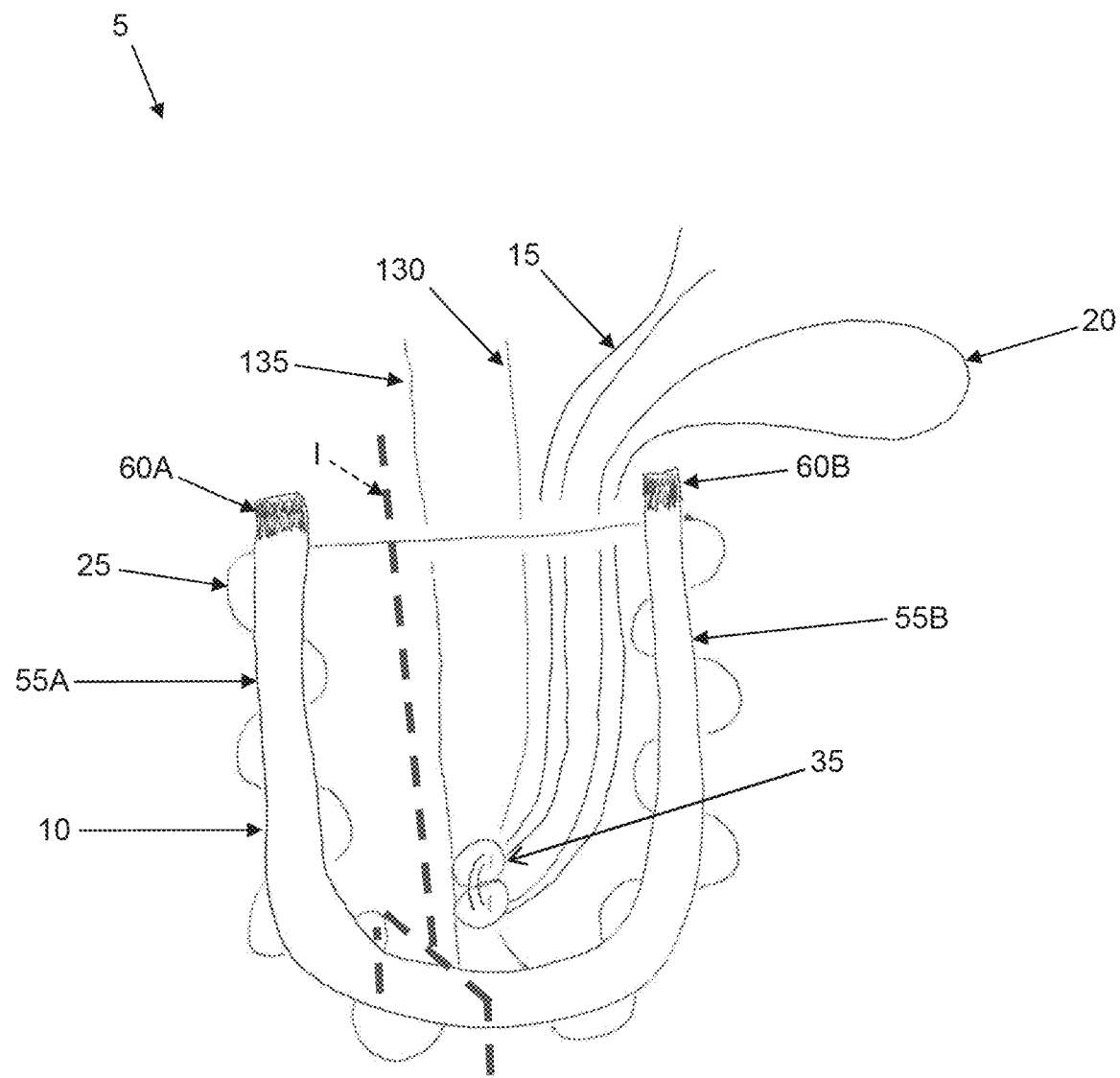
FIGS. 42 and 43 show another preferred suture anchor system formed in accordance with the present invention.
Figure 43:
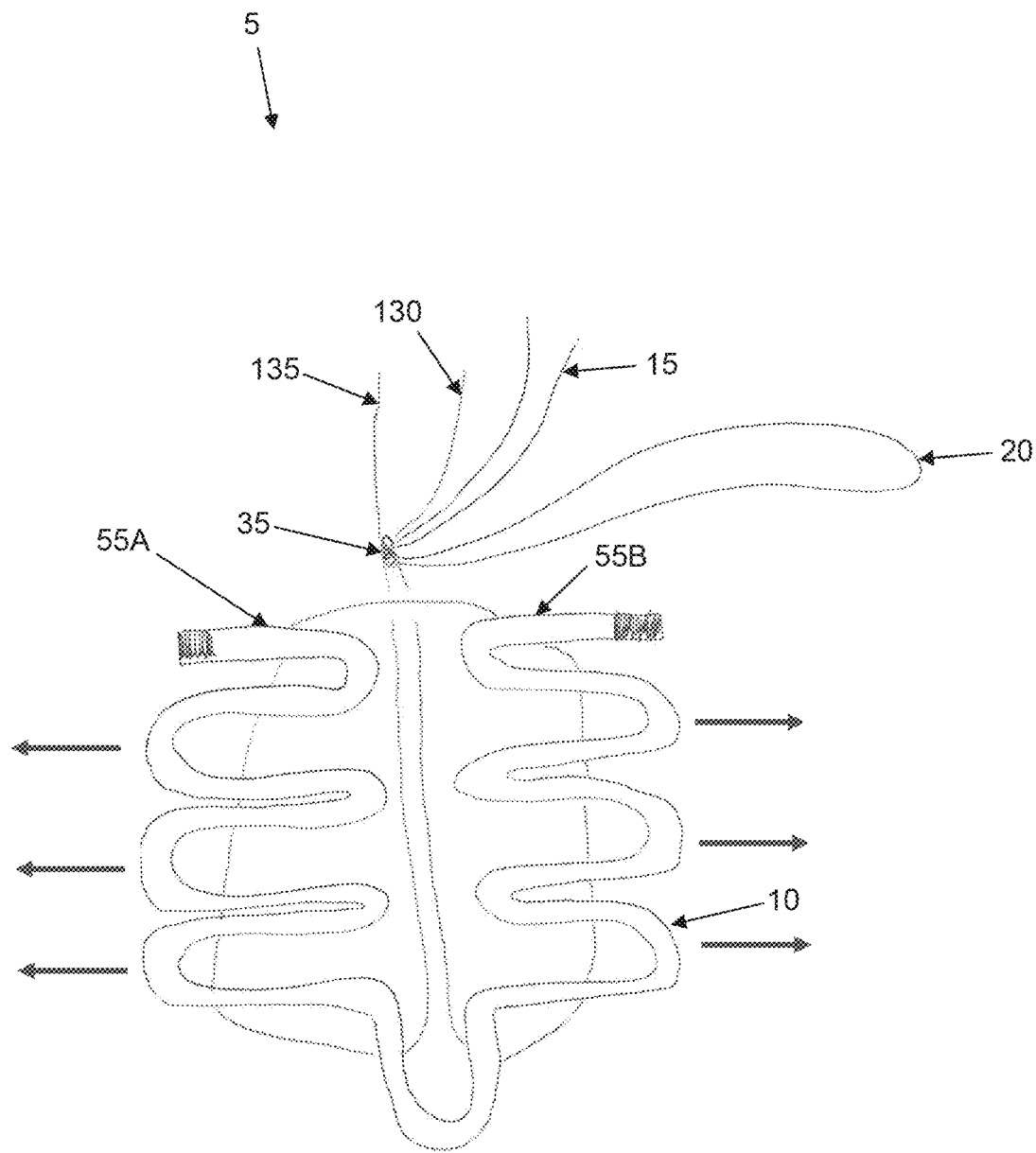

Looking next at FIGS. 42 and 43, there is shown another suture anchor system 5 which also utilizes three elements, i.e., anchor body 10 which is longitudinally and laterally deformable, and which is preferably in the form of a braided suture, repair suture 15 including repair loop 20, and working suture 25. In this form of the invention, anchor body 10 preferably comprises a woven tape or braided structure. The two free ends 60A, 60B of the tape may be fused (e.g., melted) or otherwise treated so as to form a stiffer end feature that increases engagement of anchor body 10 with the surrounding bone (i.e., so as to be less likely to slip against the side wall of a bone hole), thereby providing greater pull-out strength of anchor body 10 within the bone hole. The aforementioned fusing of the tape at the ends of anchor body 10 will also help to keep the woven fibers together and prevent unraveling and/or splaying of the woven fibers of the tape. Working suture 25 is passed through anchor body 10, preferably in the manner shown in FIGS. 42 and 43, so as to create a "horseshoe" shape for anchor body 10. One strand 130 of working suture 25 is sometimes referred to herein as Working Strand 1 (WS1) and the other strand 135 of working suture 25 is sometimes referred to herein as Working Strand 2 (WS2). A knot 35 (e.g., a constrictor knot or a Boa knot) is tied in WS2 135 in a position near the bottom of the horseshoe (see FIG. 42). Working suture 25 is passed in and out of anchor body 10, through the woven fibers of the tape. Working suture 25 connects the two free ends of the tape as shown in FIG. 42, preferably below bone-engagement features 55A, 55B (i.e., where the ends of the tape are fused so as to form a stiffer feature). WS1 130 is passed through knot 35 (e.g., a constrictor knot) that is tied in WS2 135. Repair suture 15 is passed through the tissue so as to create repair loop 20. The ends of repair loop 20 are then passed through knot 35 (e.g., a constrictor knot) formed in WS2 135.

The suture anchor system 5 of FIGS. 42 and 43 may be utilized in the following manner:

1. Repair suture 15 is passed through the soft tissue which is to be attached to the bone and then repair suture 15 is loaded (e.g., threaded) onto anchor body 10 (i.e., by passing the two strands of repair suture 15 through knot 35).

2. Anchor body 10 is inserted into the bone hole with an inserter (e.g., such as the inserter tool I, shown in FIG. 42 but not shown in FIG. 43 for clarity). The tip of the inserter preferably engages the inside arc of the horseshoe-shaped anchor body 10 so that a pushing action advances anchor body 10 into the bone hole.

3. The surgeon tensions the strands of repair suture 15 so as to pull the soft tissue into position against the bone.

4. Tension is applied to WS1 130 (but only to WS1 130) so as to deploy anchor body 10. By pulling tension on WS1 130, anchor body 10 changes shape from the horseshoe shape (FIG. 42) to an accordion shape (FIG. 43). This accordion shape further lodges anchor body 10 in the bone hole, as anchor body 10 contracts longitudinally and expands laterally, thereby creating an interference fit with the side wall of the bone hole.

5. Tension is then applied to WS2 135 (but only to WS2 135) so as to actuate knot 35 (e.g., a constrictor knot). The tension on WS2 135 causes knot 35 (e.g., a constrictor knot) to constrict, thereby reconfiguring knot 35 (e.g., a constrictor knot) from an unlocked state to a locked state. Knot 35 (e.g., a constrictor knot) locks repair suture 15 to anchor body 10. Knot 35 (e.g., a constrictor knot) also locks onto WS2 135 (and hence locks WS1 130 to WS2 135), effectively keeping anchor body 10 in a collapsed state (i.e., in a laterally-expanded condition) so as to ensure that anchor body 10 remains engaged in the bone hole.

6. Following the aforementioned steps, the inserter (e.g., such as the inserter tool I) is disengaged from anchor body 10 and removed from the implant location.

Variations may be made to the foregoing approach for utilizing the suture anchor system 5 of FIGS. 42 and 43. For example, the process to actuate the suture anchor system 5 may comprise the following additional step which would be effected between Steps 2 and 3 above:

2A. Tension is applied, simultaneously, to both WS1 130 and WS2 135 so as to seat anchor body 10 in the bone hole. Pulling tension on WS1 130 and WS2 135 allows the bone-engagement features 55A, 55B of body 10 to engage the side wall of the bone hole to prevent anchor body 10 from pulling out of the bone hole. Pulling tension on WS1 130 and WS2 135 also initiates the change in shape of anchor body 10 from the "horseshoe" shape (FIG. 42) to the "accordion" shape (FIG. 43). However, the tensioning force applied to WS1 130 and WS2 135 is not so great as to lock knot 35 (e.g., a constrictor knot), and hence still allows the tension on repair suture 15 to be adjusted prior to final locking.

This embodiment of the invention may also include variations to the anchor construction. For example, the strands of working suture 25 (i.e., WS1 130 and WS2 135) may pass through anchor body 10 at more (or less) locations, and/or at different locations, than those shown in FIGS. 42 and 43. In addition, the shape of anchor body 10 may not collapse into the folded condition as shown in FIG. 43, but may collapse into a different shape (and still expand laterally so as to create adequate pull-out strength in the bone hole).

Figure 44:
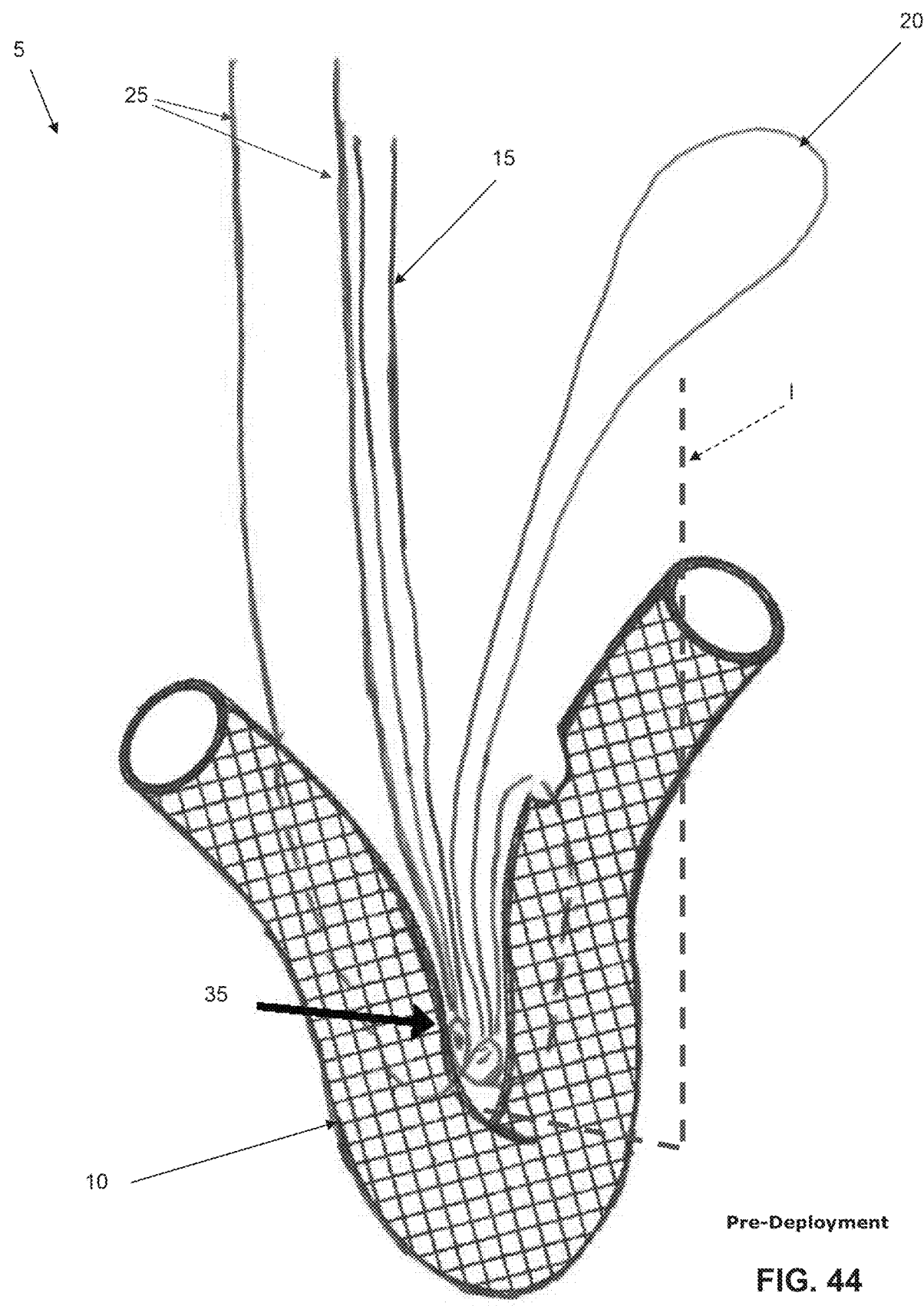
FIGS. 44 and 45 show another preferred suture anchor system formed in accordance with the present invention.
Figure 45:
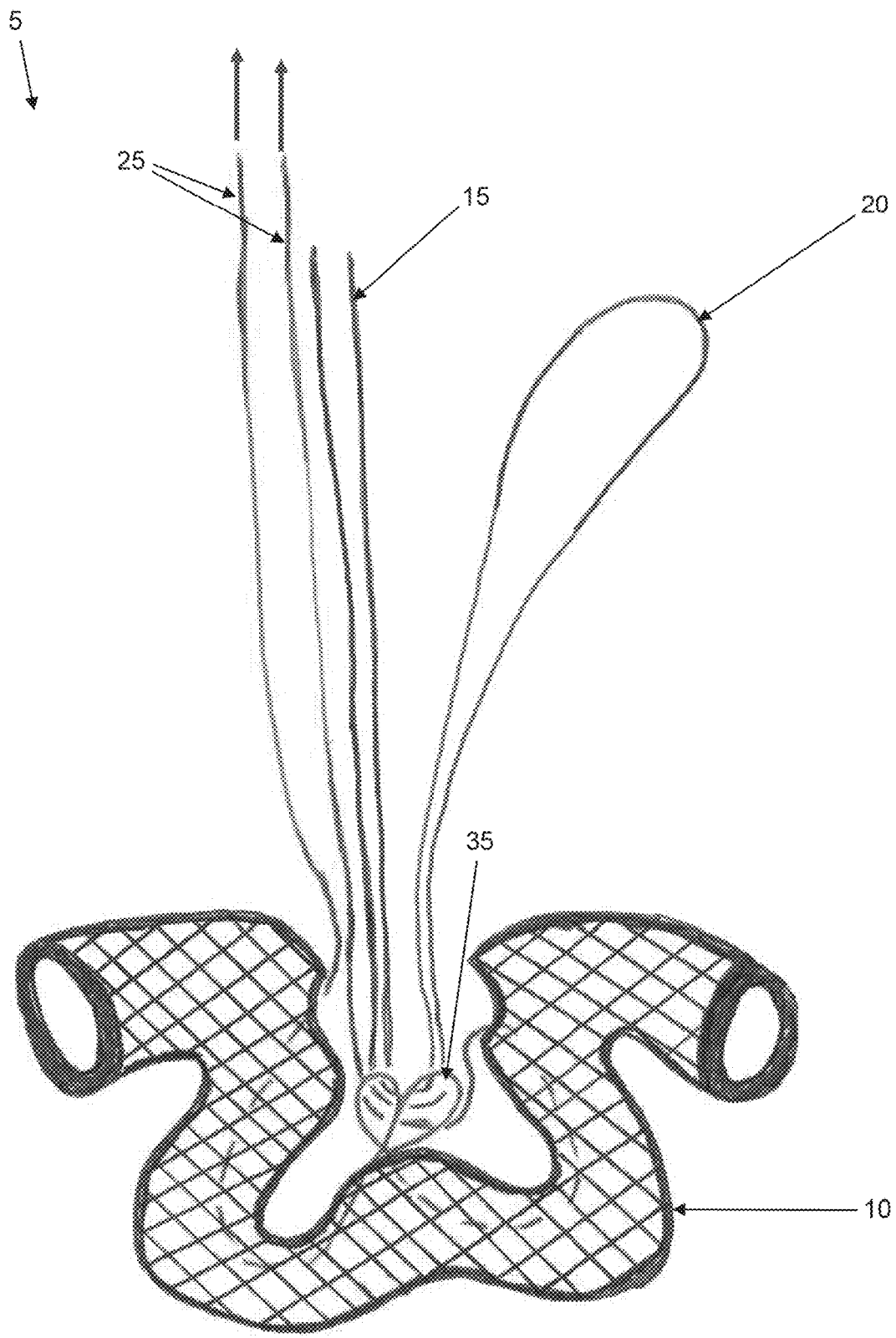

Looking next at FIGS. 44 and 45, there is shown another suture anchor system 5 which also utilizes three elements, i.e., anchor body 10 which is longitudinally and laterally deformable, and which is preferably in the form of a braided suture tube, repair suture 15 including repair loop 20, and working suture 25. By pushing on the center of anchor body 10 with the distal tip of an inserter (e.g., such as the inserter tool I, shown in FIG. 44 but not shown in FIG. 45 for clarity), the wings of anchor body 10 can fold inwardly so as to enter the bone hole and thereafter be laterally expanded within the bone hole so as to engage the side wall of the bone hole, whereby to secure anchor body 10 in the bone hole. Thereafter retracting the bridge of anchor body 10 will further longitudinally contract, and laterally expand, anchor body 10, thereby applying a larger lateral force within the bone hole, and hence further securing anchor body 10 to the side wall of the bone hole.

Thus, with this form of the invention, anchor body 10 is initially secured in place within the bone hole, repair suture 15 is tensioned so as to pull the soft tissue into place, and then working suture 25 is pulled proximally in order to deploy anchor body 10 and to lock repair suture 15 in place using knot 35 (e.g., a constrictor knot).

In FIG. 44, working suture 25 passes through a portion of anchor body 10 and comprises a knot 35 (e.g., a constrictor knot) located approximately at the bridge of the anchor body. Both strands of repair suture 15 pass through knot 35 (e.g., a constrictor knot), but not through the anchor body.

In this form of the invention, the inboard working suture 25 is used to laterally expand anchor body 10 and the outboard working suture 25 is used to tighten knot 35 (e.g., a constrictor knot) (thus locking repair suture 15 to anchor body 10). Lateral expansion of anchor body 10 may occur before or after cinching of repair suture 15. So the order of operation is preferably as follows once anchor body 10 has been placed in the bone hole: (i) adjust tension of repair suture 15 (i.e., cinching) to achieve desired position of soft tissue to bone; (ii) tension inboard working suture 25 to laterally expand anchor body 10; and (iii) tension outboard working suture 25 to lock knot 35 (e.g., a constrictor knot). It should be appreciated that, if desired, Steps (i) and (ii) could be reversed, inasmuch as compression/expansion of anchor body 10 does not affect the ability of repair suture 15 to be tensioned.

FIG. 45 shows the suture anchor system 5 of FIG. 44 in its deployed condition.

Figure 46:
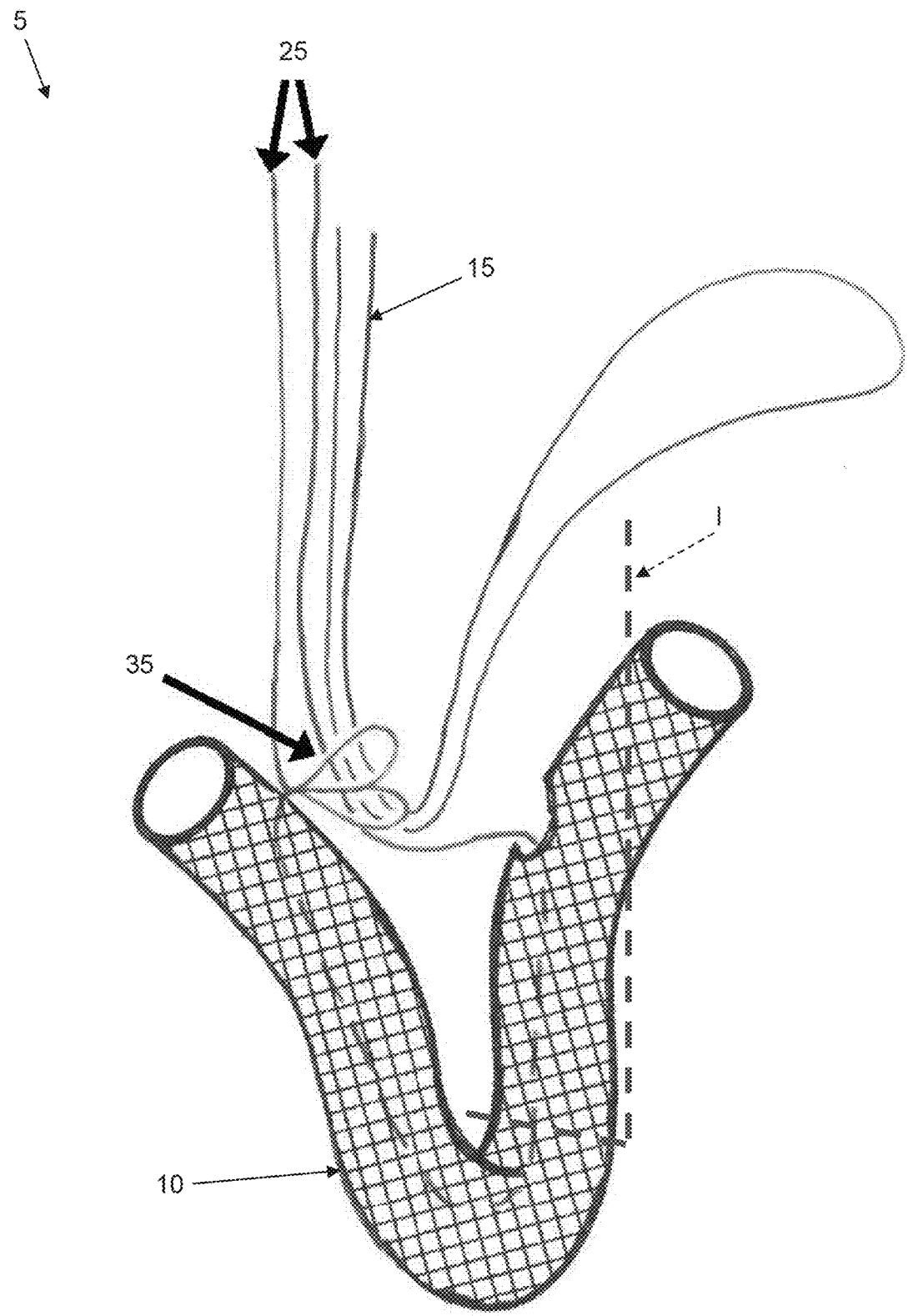
FIGS. 46 and 47 show another preferred suture anchor system formed in accordance with the present invention.
Figure 47:
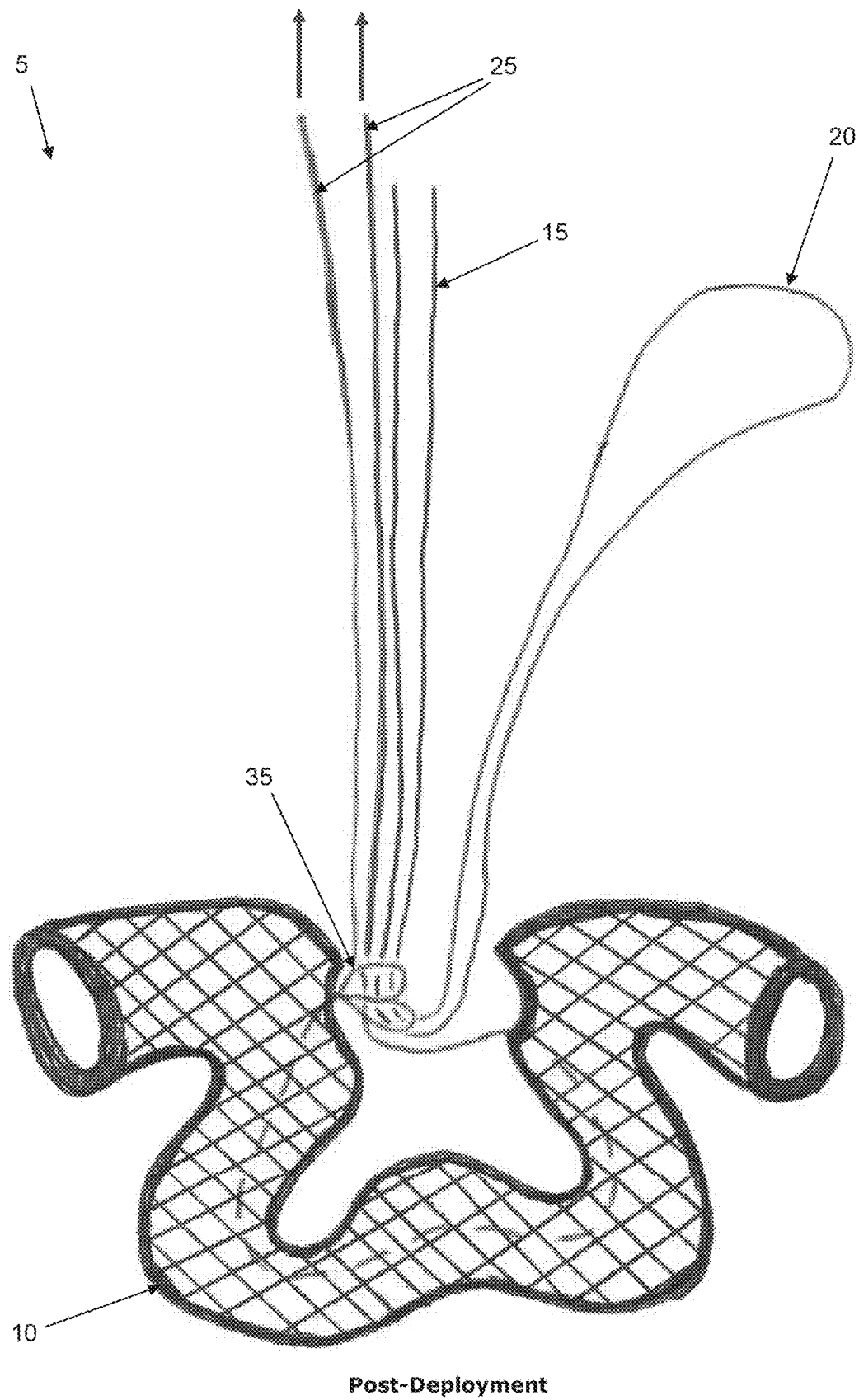

FIGS. 46 and 47 show a construction similar to that of FIGS. 44 and 45, except that knot 35 (e.g., a constrictor knot) is disposed adjacent to one leg of anchor body 10, rather than at the bridge of anchor body 10.

Use of the Novel Suture Anchor System For Other Attachments

It should be appreciated that suture anchor system 5 may also be used for attaching other soft tissue of the hip joint, or for attaching tissue of other joints, or for attaching tissue elsewhere in the body. In this respect it should be appreciated that suture anchor system 5 may be used to attach soft tissue to bone or soft tissue to other soft tissue, or to attach objects (e.g., prostheses) to bone or other tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. An apparatus for securing a first object to a second object, comprising a deformable anchor body, a working suture connected to the anchor body, and a repair suture connected to the first object, the working suture including a deployment strand forming a pre-formed knot to deform the anchor body to secure the anchor body within the second object, and a locking strand to secure the repair suture to the anchor body, wherein, with the anchor body connected to the second object and at least one of the anchor body and the working suture connected to the repair suture, the working suture is adapted to contact the anchor body to secure the anchor body within the second object and to secure the repair suture to the anchor body thereby securing the first object to the second object.

2. The apparatus of claim 1, wherein the deployment strand is adapted to be tensioned first to secure the anchor body within the second object, and the locking strand is adapted to be tensioned after the deployment strand is tensioned to subsequently secure the repair suture to the anchor body.

3. The apparatus of claim 1, wherein the deployment strand and the locking strand are adapted to be tensioned simultaneously to both secure the anchor body within the second object and secure the repair suture to the anchor body in a single step.

4. The apparatus of claim 1, wherein, the working suture and repair suture are adapted to be secured to the anchor body without requiring that a knot be tied after the anchor body is connected to the second object.

5. The apparatus of claim 1, wherein the anchor body is deformable in a longitudinal direction and a lateral direction.

6. The apparatus of claim 5, wherein deformation in theft longitudinal direction includes longitudinal contraction of the anchor body, and wherein deformation in the lateral direction includes lateral expansion of the anchor body.

7. The apparatus of claim 1, wherein the repair suture is adapted to be connected to the working suture by passing at least one end of the repair suture through the pre-formed knot when the pre-formed knot is in an unlocked configuration, and wherein the repair suture is secured to the anchor body upon altering the pre-formed knot from the unlocked configuration to a locked configuration.

8. The apparatus of claim 1, wherein the first object is soft tissue and the second object is bone.

9. The apparatus of claim 1, wherein the working suture extends through at least one opening in the anchor body, the pre-formed knot having an unlocked configuration and a locked configuration, wherein the repair suture is slidably received in said pre-formed knot when the knot is in its unlocked configuration and the repair suture is secured within said knot when said knot is in its locked configuration.

10. The apparatus of claim 9, wherein the pre-formed knot changes from its unlocked configuration to its locked configuration by tension applied to the working suture.

11. An apparatus for securing a first object to a second object, comprising:
   a deformable anchor body adapted to be positioned within the second object;
   a working suture positioned through at least a portion of the anchor body, the working suture including a pre-formed knot positioned at a location along the length of the working suture, the pre-formed knot having an unlocked configuration and a locked configuration; and
   a repair suture connected to the first object, the repair suture positioned through the pre-formed knot such that, in the unlocked configuration, the repair suture slides relative to the pre-formed knot, and in the locked configuration, the repair suture is secured by the pre-formed knot when the pre-formed knot is in contact with the anchor body.

12. The apparatus of claim 11, wherein the working suture includes a first suture strand and a second suture strand, the first strand being a deployment strand adapted to deform the anchor body to secure the anchor body within the second object, and the second strand being a locking strand adapted to change the pre-formed knot from its unlocked configuration to its locked configuration.

13. The apparatus of claim 12, wherein the deployment strand is adapted to be tensioned first to secure the anchor body within the second object, and the locking strand is adapted to be tensioned after the deployment strand is tensioned to subsequently change the pre-formed knot from its unlocked configuration to its locked configuration.

14. The apparatus of claim 12, wherein the deployment strand and the locking strand are adapted to be tensioned simultaneously to both secure the anchor body within the second object and change the pre-formed knot from its unlocked configuration to its locked configuration.

15. The apparatus of claim 11, wherein, the working suture and repair suture are adapted to be secured to the anchor body without requiring that a knot be tied after the anchor body is positioned within the second object.

16. The apparatus of claim 11, wherein the anchor body is deformable in a longitudinal direction, a lateral direction, or both.

17. The apparatus of claim 16, wherein deformation in the longitudinal direction includes longitudinal contraction of the anchor body, and wherein deformation in the lateral direction includes lateral expansion of the anchor body.

\* \* \* \* \*